(12) United States Patent
Coté et al.

(10) Patent No.: US 6,485,703 B1
(45) Date of Patent: Nov. 26, 2002

(54) COMPOSITIONS AND METHODS FOR ANALYTE DETECTION

(75) Inventors: Gerard L. Coté, College Station, TX (US); Michael V. Pishko, College Station, TX (US); Kaushik Sirkar, College Station, TX (US); Ryan Russell, College Station, TX (US); Richard Rox Anderson, Lexington, MA (US)

(73) Assignees: The Texas A&M University System, College Station, TX (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 09/354,914

(22) Filed: Jul. 9, 1999

Related U.S. Application Data
(60) Provisional application No. 60/094,980, filed on Jul. 31, 1998.

(51) Int. Cl.[7] ............................................... A61K 49/00
(52) U.S. Cl. ........................... 424/9.1; 424/9.6; 424/9.8
(58) Field of Search ........................... 424/9.1, 9.6, 9.8, 424/422, 423; 600/316, 317, 347, 365; 436/14; 524/916; 514/866

(56) References Cited

U.S. PATENT DOCUMENTS

| | | | |
|---|---|---|---|
| 5,342,789 A | | 8/1994 | Chick et al. ................ 436/501 |
| 5,786,439 A | * | 7/1998 | Van Antwerp et al. ....... 528/77 |
| 6,011,984 A | * | 1/2000 | Van Antwerp et al. ..... 600/317 |

OTHER PUBLICATIONS

Abruna et al., "Rectifying interfaces using two–layer films of electrochemically polymerized vinylupyridine and vinylbipyridine complexes of ruthenium and iron on electrodes", *J. Am. Chem. Soc.*, 103:1–5, 1981.

Armour et al., "Long–term intravascular glucose sensors with telemetry," *Artificial Organs*, 13:171, 1989.

Ballerstadt and Schultz, "Competitive–binding assay method based on fluorescence quenching of ligands held in close proximity by a multivalent receptor", *Analytica Chimica Acta*, 345:203–212, 1997.

Bretz and Abruna, "Adsorption–desorption processes of redox–active osmium thiol monolayers," *J. Electroanalyt. Chem.*, 408:199–211, 1996.

Britland et al., Micropatterning proteins and synthetic peptides on solid supports: a novel application for microelectronics *Biotechnol. Prog.*, 8:155–160, 1992.

Chen, "Fluorescent protein–dye conjugates II. gamma globulin conjugated with various dyes", *Archives of Biochemistry and Biophysics*, 133:263–276, 1969.

Clark et al., "Ionic effects of sodium chloride on the templated deposition of polyelectrolytes using layer–by–layer ionic assembly," *Macromolecules*, 30:7237–7244, 1997.

Csoregi et al., "Design, characterization, and one–point in vivo calibration of a subcutaneously implanted glucose electrode," *Anal. Chem.*, 66:3131–3138, 1994.

Damme et al., In: *Handbook of Plant Lectins: Properties and Biomedical Applications*, Wiley and Sons, West Sussex, 1998.

Degani and Heller, "Electrical Communication between Redox Centers of Glucose Oxidase and Electrodes via Electrostatically and Covalently Bound Redox Polymers," *J. Am. Chem. Soc.*, 111:2357–8, 1989.

Denisevich et al., "Electropolymerization of vinylpyridine and vinylbipyridine complexes of iron and ruthenium: homopolymers, copolymers, reactive polymers", *Inorg. Chem.*, 21:2153–2161, 1982.

Desai and Hubbell, "A solution technique to incorporate polyethylene oxide and other water soluble polymers into surfaces of biomaterials," *Biomater.*, 12:144–53, 1991.

Desai and Hubbell, "Biological responses to polyethylene oxide modified polyethylene terephthalate surfaces," *J. Biomed. Mater. Res.*, 25:829–843, 1991.

Dontha et al., "Generation of biotin/avidin/enzyme nanostructures with maskless photolithography," *Anal. Chem.*, 69:2619–2625, 1997.

Drumheller and Hubbell, "Densely crosslinked polymer metworks of poly(ethylene glycol) in trimethylolpropane triacrylate for cell resistant surfaces," *J. Biomed. Mater. Res.*, 29:207–215, 1995.

Fischer et al., "Assesment of subcutaneous glucose concentration: validation of the wick technique as a reference for implanted electrochemical sensors in normal and diabetic dogs," *Diabetol.*, 30:940–945, 1987.

Fischer et al., "Wick technique: reference method for implanted glucose sensors," *Art. Org.*, 13:453–457, 1989.

Glabe et al., "Preparation and properties of fluorescent polysaccharides", *Analytical Biochem.*, 130:287–294, 1983.

Gregg and Heller, "Redox polymer films containing enzymes. 1. A redox–conducting epoxy cement: synthesis, characterization, and electrocatalytic oxidation of hydroquinone," *J. Phys. Chem.*, 95:5970–5975, 1991.

Gregg and Heller, "Redox Polymper Films Containing Enzymes. 2. Glucose oxidase containing enzyme electrodes", *J. Phys. Chem.*, 95:5976–5980, 1991.

(List continued on next page.)

*Primary Examiner*—Michael G. Hartley
(74) *Attorney, Agent, or Firm*—Howrey Simon Arnold & White, LLP

(57) ABSTRACT

Provided are a variety of chemically sensitive, stable (insoluble over a specified period of time), nontoxic, and non-antigenic hydrogel particles which undergo a measurable change in at least one electrochemical or optical property as a function of interaction with one or more substance (s) to be detected. Also provided are methods of using these hydrogel particles to detect one or more selected analytes, and in certain aspects detect one or more analytes in vivo. Further provided are devices used to detect and measure the optical or electrochemical changes.

11 Claims, 16 Drawing Sheets

OTHER PUBLICATIONS

Gregoriou et al., "Infrared studies on novel optically responsive materials: orientation characteristics of sulfonated polystyrene/poly(diallyldimethylammonium chloride) ionic polymer multilayers on patterned self–assembled monolayers," *Applied Spectroscopy*, 51:470–476, 1997.

Hale et al., "Amperometric glucose biosensors based on redox polymer–mediated electron transfer," *Anal. Chem.*, 63:677–682, 1991.

Hammond and Whitesides, "Formation of polymer microstructures by selective deposition of polyion multilayers using patterned self–assembled monolayers as a template," *Macromolecules*, 28:7569–7571, 1995.

Hassan et al., "Dynamic behavior of glucose responsive methyacrylic acid–G–ethylene glycol hydrogels," *Macromolecule*, 30:6166–6173, 1997.

Healey et al., "Photodeposition of micrometer–scale polymer patterns on optical imaging fibers," *Science*, 269:1078–1080, 1995.

Henning and Cunningham, In: *Commercial Biosensors: Applications to Clinical, Bioprocess, and Environmental Samples;* Ramsay, G. (Ed.); John Wiley & Sons, Richmond, Virginia, vol. 148, pp 3–46, 1998.

Hodak et al., "Layer–by–layer self–assembly of glucose oxidase with a poly(allylamine)ferrocene redox mediator," *Langmuir*, 13:2708–2716, 1997.

Hou et al., "Amperometric enzyme electrode for glucose using immobilized glucose oxidase in a ferrocene attached poly(4–vinylpyridine) multilayer film," *Analytical Letters*, 30:1631–1641, 1997.

Hou et al., "Amperometric glucose enzyme electrode by immobilizing glucose oxidase in multilayers on self–assembled monolayers surface," *Talanta*, 47:561–567, 1998.

Jagemann, "Application of near–infrared spectroscopy for non–invasive determination of blood/tissue glucose using neural networks", *Zeitschrift fur Physikalische Chemie*, 191:179–190, 1995.

Katakis et al., "Electrostatic control of the electron transfer enabling binding of recombinant glucose oxidase and redox polyelectrolytes", *J. Am. Chem. Soc.*, 116:3617–3618, 1994.

Kerner et al., "Amperometric glucose sensor containing glucose oxidase, cross–linked with redox gels," In: *In Vivo Chemical Sensors: Recent Developments;* Turner, A. P. F., Alcock, S. J., Eds., 31–38, 1993.

Koudelka et al., "In vivo behavior of hypodermically implanted microfabricated glucose sensors," *Biosensors & Bioelectronics*, 6:31–36, 1991.

Lakowicz and Maliwal, "Optical sensing of glucose using phase–modulation fluorimetry," *Analytica Chimica Acta*, 271:155–164, 1993.

Linke et al., "Amperometric biosensor for in vivo glucose sensing based on glucose oxidase immobilized a redox hydrogel," *Biosensors and Bioelectronics*, 9:151–158, 1994.

Mattiasson and Ling, "partition affinity ligand assay (pala). A new approach to binding assays", *J. Immunol. Meth.*, 38:217–223, 1980.

McLean et al., "Engineering protein orientation at surfaces to control macromolecular recognition events," *Anal. Chem.*, 65:2676–2678, 1993.

Meadows et al., "Determining the extent of labeling for tetramethylrhodamine protein conjugates," *J. Immunol. Meth.*, 143:263–272, 1991.

Mooney et al., "Patterning of functional antibodies and other proteins by paotolithography of silane monolayers," *Proc. Natl. Acad. Sci. USA*, 93:12287–12291, 1996.

Nakayama et al., "Design and Properties of Photocurable Electrocunductive Polymers for Use in Biosensors", *ASAIO J.*, 41:M418–M421, 1995.

Nishihara et al., "Interdigitated array electrode diffusion measurements in donor/acceptor solutions in polyether electrolyte solvents", *Anal. Chem.*, 63:2955–2960, 1991.

Ohara et al., "Glucose electrodes based on cross–linked $[Os(bpy)_2Cl]^{+/2+}$ complexed poly(1–vinylimidazole) films", *Anal. Chem.*, 65:3512–3517, 1993.

Pathak et al., "In situ photopolymerization and gelation of water soluble monomers: a new approach for local administration of peptide drugs," *Polymer Preprints*, 33:65–66, 1992.

Pathak et al., "Rapid photopolymerization of immunoprotective gels in contact with cells and tissue", *J. Am. Chem. Soc.*, 114:8311–8312, 1992.

Pishko et al., "Electrical communication between graphite electrodes and glucose oxidase/redox polymer compounds," *Mol. Cryst. Liq. Cryst.*, 190:221–249, 1990.

Pishko et al., "Direct electrical communication between graphite electrodes and surface adsorbed glucose oxidase/redox polymer complexes," *Angewandte Chemie Intl. Ed.*, 29:82–84, 1990.

Pishko et al., "Amperometric glucose microelectrodes prepared through immobilization of glucose oxidase in redox hydrogels," *Anal. Chem.*, 63:2268–2272, 1991.

Pishko, M. V., "Macromolecular wiring of oxidoreductases and potential interesting applications" *Trends in Polymer Science*, 3(10):342, 1995.

Quinn et al., "Kinetics of glucose delivery to subcutaneous tissue in rats measured with 0.3–mm amperometric microsensors," *Am. J. Physiol.*, 269(32):E155–E161, 1995.

Quinn et al., "Photo–crosslinked copolymers of 2–hydroxyethyl methacrylate, poly(ethylene glycol) tetraacrylate and ethylene dimethacrylate for improving biocompatibility of biosensors," *Biomater.*, 16(5):389–396, 1995.

Sawhney et al., "Bioerodible hydrogels based on photopolymerized poly(ethylene glycol)–co–poly(alpha–hydroxy acid) diacrylate monomers," *Macromolecules*, 26:581–587, 1993.

Sawhney et al., "Optimization of photopolymerized bioerodible hydrogel properties for adhesion prevention," *J. Biomed. Mater. Res.*, 28:831–838, 1994.

Schmidt et al., "Glucose concentration in subcutaneous extracellular space," *Diabetes Care*, 16(5):695–700, 1993.

Sukhorukov et al., "Reversible swelling of polyanion/polycation multilayer films in solutions of different ionic strength," *Ber. Bunsenges. Phys. Chem.*, 100(6):948–953, 1996.

Sundberg et al., "Spatially–addressable immobilization of macromolecules on solid supports," *J. Am. Chem. Soc.*, 117:12050–12057, 1995.

Tanaka et al., "Diffusion characteristics of substrates in Ca–Alginate gel beads", *Biotechnol. Bioeng.*, 26:53–58, 1984.

Tatsuma et al., "Enzyme electrodes mediated by a thermoshrinking redox polymer," *Anal. Chem.*, 66:1002–1006, 1994.

West and Hubbell, "Photopolymerized hydrogel materials for drug delivery applications", *Reactive Polymers*, 25:139–147, 1995.

Whitesides et al., "Molecular self-assembly and nanochemistry: A chemical strategy for the synthesis of nanostructures," *Science*, 254:1312–1319, 1991.

Wilson and Reach, "Can continuous glucose monitoring be used for the treatment of diabetes?," *Anal. Chem.* 64:381A–386A, 1992.

Wilson et al., "Progress toward the development of an implantable sensor for glucose," *Clin. Chem.*, 38:1613–1617, 1992.

* cited by examiner

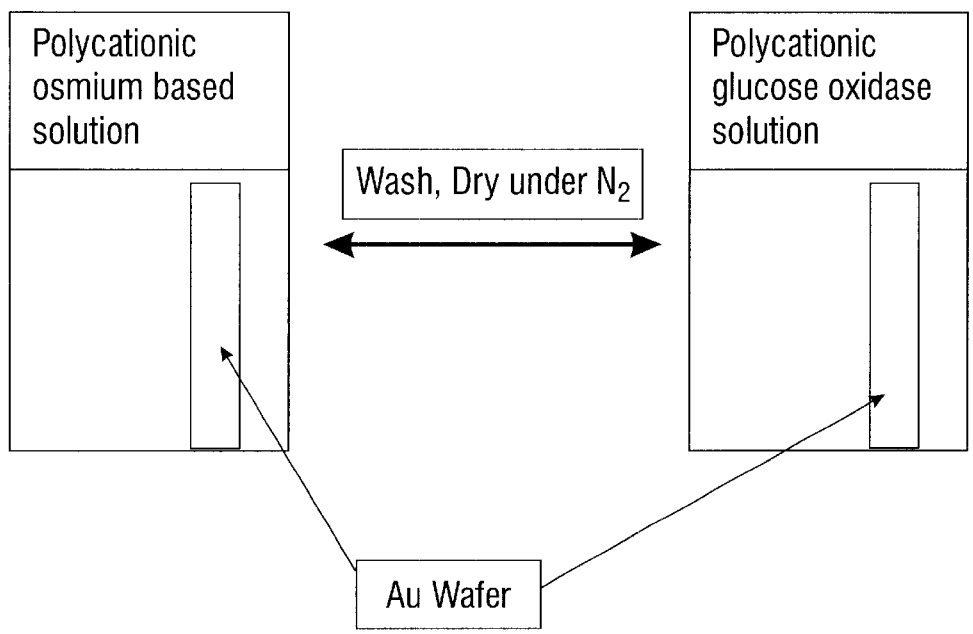
FIG. 15
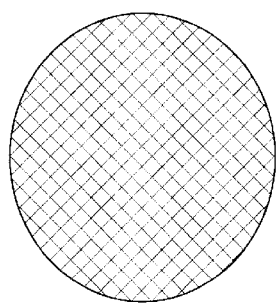
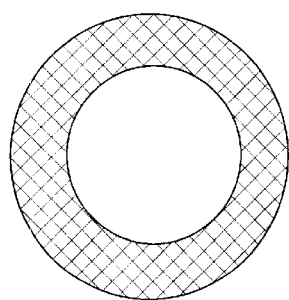
FIG. 16A                    FIG. 16B

COMPOSITIONS AND METHODS FOR ANALYTE DETECTION

This application claims priority to U.S. provisional patent application serial No. 60/094,980, filed Jul. 31, 1998, the entirety of which is incorporated herein by reference.

BACKGROUND OF THE INVENTION

1. Field of the Invention

The present invention relates generally to the fields of chemistry, biology, biochemistry, medical devices and chemical detection devices. More particularly, it concerns polymeric compositions, methods and devices for the detection of one or more selected analyte(s), preferably detection of one or more analyte(s) in vivo. The present invention also concerns polymeric constructs for analyte detection and concentration measurement using visualization or production of electrochemical signals from a construct after implantation in vivo. In particular, the invention concerns detection or measurement of blood glucose levels in vivo for the management of diabetes. Additionally, devices are provided to detect and measure the optical or electrochemical changes in polymeric constructs.

2. Description of Related Art

Diagnosis of various disease and injury conditions are often made on the basis of the detection and measurement of the concentration of one or more body chemicals or analytes. Currently, the levels of numerous selected body chemicals or analytes are measured manually and invasively by withdrawing a sample of blood. For most analytes the sample is usually sent to a centrally located lab where it is typically analyzed with large and expensive machines using wet chemistry, immunoassays, and/or enzyme electrode based biosensing. This mode of operation is expensive and time consuming, and therefore represents a significant hazard to critically ill patients in operating rooms, intensive care units and trauma/critical care units. In particular, for trauma/critical care cases it is known that survival rates decrease dramatically if treatment is delayed for more than one hour. For instance, the measurement of arterial blood gases is a primary indicator of respiratory function, and lactate values are used as an indicator of shock. Therefore, the frequent assessment of these and other analytes is essential to clinical diagnosis and management.

Exemplary of diseases that require frequent monitoring of analytes is diabetes mellitus. Diabetes mellitus is a chronic disease that, if unregulated, can give rise to large fluctuations in blood glucose levels. This disease currently afflicts over 100 million people worldwide and nearly 14 million in the United States (National Institute of Diabetes and Kidney Diseases, 1994). In the U.S. this disorder, along with its associated complications, is ranked as the seventh leading cause of death (Cotran et al., 1989). In order to maintain normal glucose levels, blood glucose must be monitored frequently throughout the day. Self-monitoring of blood glucose is recommended for diabetic patients as the current standard of care and, since the announcement of the Diabetes Control and Complications Trial results (National Institute of Diabetes & Digestive & Kidney Diseases, 1993), there is now no question that intensive management of blood sugars is an effective means to prevent or at least slow the progression of diabetic complications such as kidney failure, heart disease, gangrene, and blindness (National Institute of Diabetes & Digestive & Kidney Diseases, 1993; Wysocki, 1989; Speicher, 1991).

The goal of diabetes therapy is to approximate the 24-hour blood glucose profile of a normal individual. Without regulation, hypoglycemia, a condition in which the blood glucose level falls well below normal, can result, which can cause the patient to slip into a coma and eventual death. Alternatively, a condition known as hyperglycemia can develop, in which blood glucose levels can rise considerably above normal levels. If left untreated, these abnormally high blood glucose levels may result in long-term complications such as an increased risk of coronary artery disease, hypertension, retinopathy, neuropathy, and nephropathy (National Institute of Diabetes and Kidney Diseases, 1994; Cotran et al., 1989; National Institute of Diabetes & Digestive & Kidney Diseases, 1993; Hanssen, 1986).

Proper treatment includes maintaining blood glucose levels near normal levels. This can only be achieved with frequent blood glucose monitoring so that appropriate actions can be taken, such as insulin injections, proper diet, or exercise. Unfortunately, the currently preferred method of sensing is an invasive technique, requiring a finger stick to draw blood each time a reading is needed. This approach is both time-consuming and painful. Therefore, there is a lack of compliance among the diabetic population for even monitoring their levels once per day, not to mention the recommended five or more times daily (National Institute of Diabetes & Digestive & Kidney Diseases, 1993).

One potential method of achieving tighter metabolic control in diabetic patients is a closed-loop insulin delivery system, incorporating a microprocessor-controlled insulin pump and a glucose sensor. Various amperometric devices have been fabricated based upon the electrochemical oxidation of $H_2O_2$ generated during a reaction between glucose and oxygen catalyzed by glucose oxidase (Tatsuma et al., 1994). The focus of amperometric biosensors appears to have shifted towards the incorporation of charge mediators as electron "shuttles" between the redox center of the enzyme and the electrode surface (Hale et al., 1991; Pishko et al., 1991). These $H_2O_2$ and mediator based biosensors have taken on many forms, including covalent immobilization directly to the electrode surface, retention by a membrane, or entrapment in a polymer hydrogel (Henning, T. and Cunningham, D., 1998).

Glucose sensors, which use an enzyme (glucose oxidase) to achieve specificity, are currently not stable or sensitive enough to meet the demands of a closed-loop delivery system. As a result, the application of glucose biosensors has been primarily limited to home glucose test meter and blood-gas instruments containing sensors for glucose (Rouhi, 1997). There are a number of reasons for this lack of commercial progress, both technical and economic. Technically, many proposed biosensors for glucose simply do not have the accuracy and stability (operational or storage) to meet the desired need. Inaccuracy and imprecision in sensor performance are frequently due to imprecision in sensor manufacturing, e.g. immobilized biomolecules cannot be deposited on transducer surfaces at the same density and with the same mass transfer limitations. Instability is often a problem inherent in the biomolecule, the result of poor immobilization methods resulting in leaching, or inactivation of the biomolecule by species present in the sensing environment (Pishko, M. V., 1995).

Glucose detection devices have been reported that quantify glucose concentration in blood and body fluids. One such device uses fluorescence resonance energy transfer (FRET) between a labelled ligand and a labelled carbohydrate-containing receptor (U.S. Pat. No. 5,342,789). The binding of glucose to the receptor prevents energy transfer from the labelled receptor to the labelled ligand, and thus prevents the quenching of the flourescence of the labelled receptor.

Noninvasive methods to quantify blood chemicals, particularly glucose, have been attempted using various optical approaches. Four primary approaches being investigated, including near-infrared (NIR) absorption spectroscopy (Small et al., 1993; Marbach et al., 1993; Robinson et al., 1992; McShane et al., 1997), NIR scattering (Kohl and Cope, 1994; Maier et al., 1994), polarimetry (March et al., 1982; Gough, 1982; Cameron and Coté, 1997; King et al., 1994; Coté et al., 1992), and Raman spectroscopy (Goetz, Jr. et al., 1995; Berger et al., 1997).

Each of these approaches suffer primarily from a lack of specificity. The NIR scatter approach is confounded by changes in indices of refraction, since tissue scattering is also caused by a variety of substances and organelles which all have different refractive indices. The Raman approach is non-specific, lacks good sensitivity, requires high powers, and suffers from large background autofluorescence of the tissue in vivo (Coté, G. L., 1997).

Although reports have been given for in vivo near-infrared (NIR) absorption spectroscopy data, these results have been primarily based on bolus injections of intravenous glucose (Marbach, 1993; Robinson 1992). Since the multivariate statistics can produce strong temporal correlation due to independent factors these results are suspect and could likely be due to temporal variations other than glucose. Another drawback to the NIR approach is a lack of repeatability of the NIR signal in vivo both within and especially between patients (Day, 1996; Sabatini, 1996). Thus, the main drawback for the NIR technique is again the lack of specificity as well as of lack of sensitivity in the presence of these confounders.

For polarimetry to be used as a noninvasive technique for blood glucose monitoring, the signal must be able to pass from the source, through the body, and to a detector without total depolarization of the beam. Both the skin and eye have been used as detection sites for this technique. Overall, tissue birefringence and motion artifact are sources of error for this approach regardless of the sensing site. The change in rotation due to other chiral molecules such as proteins creates problems of specificity. Thus, as with all the previously described potentially noninvasive optically based approaches the primary drawback is not only the lack of sensitivity but the lack of specificity of these approaches.

The use of fluorescence was investigated for glucose monitoring in vivo using an indwelling fiber optic approach and a membrane (Mansouri and Schultz, 1984; Schultz et al., 1982), however, to date it has not been developed as a noninvasive technique. In this approach the fluorophore was bound on the inner surface of the membrane at the tip of the fiber. Glucose had a higher affinity for the membrane base molecule and displaced the fluorophore causing the fluorescent light to be returned through the fiber and thus had good specificity. However, the indwelling optical fiber-based approach has many of the same problems associated with previous electrochemical approaches, including membrane fouling, encapsulation, and decrease in response time, as well as opening the body to potential infection. In addition, the fiber was intravenously implanted and thus was small, yielding very low signal-to-noise-ratios (Mansouri and Schultz, 1984; Schultz et al., 1982).

Biosensor applications for the detection and identification of pathogens by DNA or RNA hybridization, or rapid DNA sequencing require a high-density pattern of individual sensing elements (Chee et al., 1996; Yershov et al., 1996). Thick film technology have been used for a number of years to fabricate single biosensors for the home glucose test market, but this technology is not amenable to the fabrication of micrometer scale arrays of sensors. Biotin/Avidin systems have been utilized to immobilize enzymes in an ordered fashion, albeit without charge mediators (Dontha et al., 1997). If biosensors are to see more wide spread application, sensor fabrication technologies must be developed that allow the development of stable, easily manufactured multisensor arrays (Madou and Tierney, 1993).

Recent research on patterning biomolecules on surfaces has focused primarily on self-assembled monolayers (SAMs; Mooney et al., 1996; Whitesides et al., 1991), and tethered biomolecules on surfaces that may potentially form addressable patterned arrays (Mooney et al., 1996; Britland et al., 1992; McLean et al., 1993). These patterned surfaces are formed, particularly using alkane thiols and their derivatives on gold-coated surfaces. SAMs also permit the site specific immobilization and orientation of biomolecules on a surface. However, two-dimensional approaches such as SAMs may limit the number of biomolecule recognition sites on the sensor surface, and thus may have low signal levels and require shielding or other measures to reduce noise. The structure of self-assembled molecules on a surface can also result in defects or "pinholes" in the monolayer and contribute to instability, particularly at applied potentials. The current adhesion chemistry used in the fabrication of SAMs also permits monolayer formation only on a limited number of surfaces, most commonly gold. In addition to monolayers, photolithography and other photoinduced patterning chemistries were highlighted in a few studies, demonstrating the formation of patterned biomolecule surfaces (Sundberg et al., 1995; Dontha et al., 1997) and micropatterned polymers for optical chemical sensing (Healey et al., 1995).

In prior research of biosensors based upon redox polymers coupled to biorecognition molecules such as oxidoreductases, the polymer served to immobilize the enzyme via formation of an insoluble protein/polymer complex (Pishko et al., 1990a; Pishko et al., 1990b; Tatsuma et al., 1994), through the physical entrapment of the enzyme in a polymer film (Hale et al., 1990; 1991), and/or through the covalent cross-linking of the enzyme and polymer (Gregg and Heller, 1991b; Ohara et al., 1993). Amperometric biosensors based on redox polymer/enzyme complexes were shown to be miniaturizable (Pishko et al., 1991) and could measure analytes either intravenously or subcutaneously when implanted in rats (Csoregi et al., 1994; Kerner et al., 1993; Linke et al., 1994; Quinn et al., 1995b; Schmidtke et al., 1996). In all of these studies, the redox polymers were synthesized by heat-induced free radical polymerization. Electropolymerization of vinyl-containing redox monomers was used to polymerize and deposit redox polymers on electrodes but was not demonstrated as an effective method of immobilizing enzymes or forming patterned films (Denisevich et al., 1982; Abruna et al., 1981). The photopolymerization of redox polymers was previously reported for vinylferrocene/acrylamide copolymers (Nakayama et al., 1995).

One technique in biosensor construction involves the building of individual monolayers on surfaces based upon the attraction between oppositely charged species. Issues involved in the development of patterned polyion multilayers that have been examined include solution ionic strength and number of multilayers (Hammond and Whitesides, 1995; Clark and Hammond, 1998; Gregoriou et al., 1997). Typically, these systems utilized Sulfonated Polystyrene as the polyanionic component and compounds such as Poly (allylamine hydrochloride) as the polycationic component.

These polyion multilayers were grown in distinct patterns through the use of micro-contact printing and blocking agents anchored to a gold substrate. The effect of solution ionic strength on these multilayers has been examined (Clark et al., 1997; Sukhorukov et al., 1996) as well as the attachment of redox-active osmium complexes via similar techniques (Bretz and Abruna, 1996). Alternating glucose oxidase (GOX) and charge mediator layers for the fabrication of a glucose enzyme electrode have been utilized (Chen et al., 1969; Hou et al., 1997; Hou et al., 1998). Other groups have also performed similar work utilizing a ferrocene derivative as their poly-cationic charge mediator (Hodak et al., 1997).

PEG-based coatings have been used to improve the biocompatibility of implanted glucose sensors and demonstrated that these hydrogels were not glucose mass transfer limiting (Quinn et al., 1995). PEG-based polymers have previously been evaluated for in vivo use as protein drug delivery devices, for postoperative adhesion prevention, and for biocompatible membranes over electrochemical sensors (West and Hubbell, 1995; Pathak et al., 1992; Sawhney et al., 1994). The stability and solubility of numerous proteins, including bovine serum albumin, catalase, and interleukin-2, is reportedly increased upon conjugation to PEG (Delgado et al., 1992). Monomethoxy poly(ethylene glycol)-5000 has been conjugated to Con A while retaining Con A's sugar binding abilities (Mattiasson and Ling, 1980). Lakowicz and co-workers (Lakowicz and Maliwal, 1993) have also developed fluorescent assays for glucose, based on phase-modulation fluorimetry and Con A/dextran moieties. These studies were conducted in an aqueous solution, and it was indicated that a polymeric acceptor may be used to shield the glucose sensor behind a glucose-permeable barrier (Lakowicz and Maliwal, 1993).

Work invoking PEG and glucose oxidase focused on pH-sensitive hydrogels which swelled and shrank as a result of glucose concentration. The large physical changes needed to measure glucose concentrations were slow to develop, and limited due to the swelling resulting in an influx of buffered solution, which reduced or eliminated the small change in pH (Hassen et al., 1997).

Despite these attempts at alternative methods of analyte detection, there is still a need to design and develop technology that would provide an either minimally invasive or noninvasive method to measure biological analytes or external chemicals. There is a need for devices and methods to easily allow an increase in the accuracy and frequency of measurement, identify potentially hazardous compounds, provide for tighter control of patient compliance, while fostering fewer secondary complications than current methods. Such devices and methods would thus represent a significant advance in the art.

SUMMARY OF THE INVENTION

The present invention overcomes these and other deficiencies present in the art by providing a variety of chemically sensitive, stable (insoluble over a specified period of time), nontoxic, and non-antigenic hydrogel structures, wherein the structure may be, for example, in the form of a particle or in the form of a hydrogel adherent to a substrate, such as an electrode substrate. In preferred embodiments, two or more electodes are used. However, electrodes that are not in contact with the hydrogel may also be used in certain embodiments. The hydrogel structure may undergo a measurable change in at least one electrochemical or optical property as a function of interaction with one or more substance(s) to be detected. Also provided are methods of using these hydrogel particles to detect one or more selected analytes, either in in vivo or external to a living organism. The present invention provides an implantable non-invasive monitoring approach, which may provide better compliance and reduce the risk of infection. Additionally provided are devices used to detect and measure the optical or electrochemical changes.

The present invention first provides a composition comprising an analyte sensitive compound comprised within a hydrogel, wherein the hydrogel comprises a polymerized material including but not limited to poly(ethylene glycol), poly(ethylene glycol)-co-anhydride, poly(ethylene glycol)-co-lactide, poly(ethylene glycol)-co-glycolide, poly (ethylene glycol)-co-orthoester, poly isopropylacrylamide, polyHEMA, polyacrylamide, sodium alginate or a combination thereof. In certain embodiments, the hydrogel is a macromer, or construct made of polymerized material or polymers that are themselves polymerized by covalent attachment at the ends of the individual polymers that comprise the macromer. Polymerized material or polymers that may be polymerized in the macromer, include but are not limited to, poly(ethylene glycol), poly(ethylene glycol)-co-anhydride, poly(ethylene glycol)-co-lactide, poly (ethylene glycol)-co-glycolide, poly(ethylene glycol)-co-orthoester, poly isopropylacrylamide, polyHEMA, polyacrylamide, sodium alginate or a combination thereof. As defined herein, a "hydrogel" refers to a polymeric material that allows a fluid or aqueous medium to diffuse throughout the material. This property of rapid diffusion allows rapid contact of the hydrogel and its components with substances dissolved or dispersed within the fluid or aqueous medium. The hydrogel may be polymerized by any technique known to those of ordinary skill in the art, such as for example, chemical induced polymerization or photopolymerization. The hydrogel may act as a support or framework for additional components, such as analyte sensitive compounds, monomers, comonomers, and other materials. The hydrogel support may covalently bind or non-convalently entrap the additional materials.

In various embodiments of the present invention, the composition may further comprise additional monomers to alter the properties of the hydrogel in advantageous ways. A monomer that is contemplated as being useful in the present invention include, but is not limited to, a vinyl-containing monomer, an acrylate-containing monomer, a methacrylate-containing monomer or a combination thereof. The hydrogel may be copolymerized with a monomer, including but not limited to, a vinyl-containing monomer, acrylate-containing monomer, ethacrylate-containing monomer or combination thereof. A monomer may function to cross-link the hydrogel, or foster contact and/or binding of multiple hydrogels. Such contact may be fostered by cross-linking the plurality of hydrogels with the monomers and/or enhancing the affinity of an at least first body of hydrogel material for an at least second body of hydrogel material by conferring opposite charges to each successive body or layer of hydrogel material. Additionally, a monomer may have specific affinity for, or be capable of chemically linking to, an analyte sensitive compound or additional material.

In certain aspects, a vinyl-containing monomer is acrylic acid, allyl amine, styrene, allyl alcohol, acrylamide, acrylate-PEG-hydroxysuccinimde ester, Os(vinyl pyridine) (bis-bipyridine)$_2$Cl, vinyl imidazole, vinyl bipyridine, vinyl ferrocene, styrene, pentadiene, methyl pentadiene or poly-acrylated monomer. In other aspects, one or more monomers comprise the composition. As used herein certain embodiments, a comonomer is two or more monomers used to comprise the composition. In certain embodiments, the hydrogel comprises a copolymer of two or more polymers. The copolymer may further comprise a monomer or comonomers. The monomer or comonomer may include, but is not limited to, a hydrophobic, a cationic, an anionic, a neutral but hydrophilic, a biomolecule reactive, a redox, or a multifunctional crosslinking monomer or comonomer, or a combination thereof. As used herein certain embodiments, a biomolecule reactive monomer or comonomer contains a reactive group such a vinyl, methylacrylate or acrylate moiety to covalently bond to the hydrogel composition, as well as being able to bind to a biomolecule, including but not limited to, proteins, nucleic acids or lipids. As used herein certain embodiments, a redox reactive monomer or comonomer contains a chemical group such a vinyl, methylacrylate or acrylate moiety to covalently bond to the hydrogel composition, as well as being able to bind to a redox reactive moiety, i.e. a compound selected for its ability to undergo oxidation or reduction, or oxidize or reduce other compounds. As used herein certain embodiments, a multifunctional monomer or comonomer contains more than one reactive groups such a vinyl, methylacrylate or acrylate moiety to covalently bond to one or more the hydrogel composition(s), as well as being able to bind to other agents, such as, for example, a analyte detection agent. In some embodiments, the hydrogel is copolymerized with one or more comonomers or monomers. A preferred hydrophobic comonomer includes styrene, acrylic acid, methacrylic acid, an alkene, or a combination thereof. A preferred alkene is pentene. A preferred cationic comonomer includes allyl amine or acrylamide. A preferred anionic comonomer is styrene sulphonate. A preferred neutral but hydrophilic comonomer is allyl alcohol. A preferred biomolecule reactive comonomer is acrylate-PEG-hydroxysuccinimide ester, wherein the acrylate moeity is preferred to bind to the hydrogel, and the hydroxysuccinimide is preferred as a biomolecule reactive or binding moiety. A preferred redox comonomer includes vinyl ferrocene, an Os derivative of vinyl pyridine, an Os derivative of vinylimidazole, a Ru derivative of vinyl pyridine or a Ru derivative of vinylimidazole. A preferred multifunctional crosslinking comonomer includes trimethylol propane triacrylate or pentaerythritol triacrylate.

In certain aspects, the hydrogel may further comprise a positively charged polyelectrolyte, a negatively charged polyelectrolyte or a combination thereof.

The analyte sensitive material may be attached to hydrogel or comprised within the hydrogel. In certain preferred aspects, the analyte sensitive compound is non-covalently entrapped in the hydrogel and/or covalently attached to the hydrogel. In a preferred aspect, analyte sensitive compound binds at least one selected analyte. An analyte that may be detected include, but is not limited to, a carbohydrate, a protein, a nucleic acid, a lipid, a chemical (in solid, or preferably, liquid or gas form), or a combination thereof.

The analyte sensitive material may be any compound or grouping of compounds that binds to or interacts with a substance to be detected. The analyte sensitive material may also detect the analyte indirectly by detecting a by-product of its presence, including but not limited to, a chemical degradation product of the analyte or a change in the pH of the medium in contact with the composition. As used herein "detect an analyte" or "detect a substance" will be understood to encompass direct detection of the analyte itself or indirect detection of the analyte by detecting its by-product (s). Detection of an analyte may be by contact of the analyte sensitive material with the analyte or its by-product. The analyte sensitive material may be a protein that binds an analyte or its by-product, including but not limited to an enzyme, an antibody, or a lectin. In a preferred aspect, the enzyme is a glucose oxidase or an organophosphate hydrolase enzyme.

In certain embodiments of the present invention, the analyte sensitive compound produces an electrochemical change upon contact with a selected analyte. In a preferred aspect, the composition may further comprise one or more electrodes in operational association with the hydrogel. In a particularly preferred aspect, the electrode detects an electochemical change upon contact of the analyte sensitive compound with a selected analyte.

In certain embodiments of the present invention, the analyte sensitive compound produces an optical change upon contact with a selected analyte. In a preferred aspect, the optical change is a fluorescence change upon contact with the selected analyte. In one aspect, the composition may further comprise an optical detection device in operational association with said hydrogel. In a particularly preferred aspect, the optical detection device comprises an one or more electrodes, transistors, diodes, or photoelectric cells that detects or communicates the detection of an optical change upon contact of said analyte sensitive compound with a selected analyte.

Various mechanisms may be used to produce an optical change upon contact of the analyte sensitive material with the analyte. The analyte may, for example, change the pH of the medium in contact with the analyte sensitive material. The analyte sensitive material may, for example, comprise a pH sensitive dye that undergoes a change in color, fluorescence or phosphorescence upon change of the medium's pH. In a preferred aspect, the analyte produces a change in pH upon contact with the analyte sensitive material or hydrogel.

In certain aspects, the analyte sensitive compound and/or the hydrogel is in operable association with at least a first fluorescent label. In a preferred aspect the analyte sensitive compound binds an analyte, and the binding of the analyte to the analyte sensitive compound alters, increases and/or reduces the fluorescence of the at least a first fluorescent label. In particularly preferred aspects, the first fluorescent label is HPTS or SNAFL-1.

In certain embodiments, the composition comprises a component that binds to the analyte sensitive compound, wherein binding of the analyte to the analyte sensitive compound decreases the binding of the analyte sensitive compound and the component. In one aspect, the analyte competes with the component for binding to the analyte sensitive compound.

In a preferred aspect, the analyte sensitive compound or construct comprises a first conjugate that produces an optical change or electrochemical change. In another aspect, the analyte sensitive compound or construct comprises a second conjugate that produces an optical change or electrochemical change. The first or second conjugate may comprise a component that binds to the analyte sensitive compound or construct. The component may bind the first or second conjugate. In a preferred aspect, the first and/or second conjugate is a fluorophore conjugate. In another preferred aspect, the fluorescence of the first fluorophore conjugate is quenched by the second fluorophore conjugate. In a particularly preferred aspect, the first conjugate comprises dextran and the second conjugate is concanavalin A. Preferred fluorophores include, but are not limited to, FITC or TRITC. In a particularly preferred aspect, the first fluorophore conjugate comprises FITC and the second fluorophore conjugate comprises TRITC.

An analyte sensitive compound or construct of analyte sensitive compounds for use in the present invention include, but are not limited to, a nucleic acid, a protein, Con A, a Os(vinyl bipyridine)(bis pyridine)$_2$ derivative or Os(vinyl bipyridine)(bis-phenathroline)2. The analyte sensitive protein may bind to a particular analyte, including but not limited to, a lectin that binds to glucose, or an enzyme that binds to a specific analyte, including but not limited to, glucose oxidase, galactose oxidase, cholesterol oxidase, cholesterase, lactate oxidase, glucose dehydrogenase, pyruvate oxidase, lactate dehydrogenase or bilirubin oxidase. In certain preferred aspects, the analyte sensitive compound is an oxidoreductase or a glucose oxidase. In additional aspects of the invention, the analyte sensitive protein is an antibody. In certain preferred aspects, the antibody is a monoclonal antibody. Monoclonal antibodies can be tailor made to preferentially or specifically bind a particular epitope or compound, and thus may be used to grant the same specificity in the detection of a particular analyte in the present invention. The amino acid and nucleotide sequences for various proteins, enzymes and antibodies are well known to those of ordinary skill in the art, and may be found at computerized databases known to those of ordinary skill in the art. One such database is the National Center for Biotechnology Information's Genbank and GenPept databases (http://www.ncbi.nlm.nih.gov/). The coding regions for these known genes may be amplified and/or expressed using the techniques disclosed herein or as would be know to those of ordinary skill in the art. The expression of proteins, including enzymes, is generally known to those of skill in the art of molecular biology, for example, see Sambrook et al. (1989), incorporated herein by reference. The technique for preparing new monoclonal antibodies to a particular epitope to be detected as an analyte is quite straightforward, and may be readily carried out using techniques well known to those of skill in the art, as exemplified by the technique of Kohler & Milstein (1975), incorporated herein by reference.

In a preferred embodiment, the hydrogel is further defined as a hydrogel microsphere. In particularly preferred aspects of this embodiment, the hydrogel is fabricated from poly (ethylene glycol) diacrylate, sodium alginate (a.k.a. alginic acid) or a combination thereof. In other preferred aspects the hydrogel further comprises acrylic acid, allyl amine, styrene, allyl alcohol, acrylamide or a combination thereof. In a particularly preferred aspect, the hydrogel microsphere surrounds a liquid core. In certain aspects, the liquid core comprises water, alginic acid, or a co-polymer of poly ethylene glycol and poly isopropyl acrylamide, or a combination thereof. In certain aspects, it is preferred that the analyte sensitive compound or construct is contained or entrapped within said liquid core.

In other embodiments, the hydrogel undergoes a phase change to a solid state at a temperature from about 22° C. to about 37° C. This embodiment allows the hydrogel to remain in a fluid state until placed within a living organism, or other environment at or about 22° C. or greater in temperature. This embodiment allows the creation of particularly shaped hydrogel structures in living organisms or environments at or about 22° C. or greater in temperature. This embodiment is particularly useful to prepare the hydrogel materials at low temperatures for storage until use, or for molding the hydrogel into a desired shape.

In other embodiments, the composition is further defined or shaped as an at least one layer of hydrogel material. The hydrogel may further comprise a plurality of layers. In a preferred aspect, at least one layer contacts at least one successive layer to form a plurality of layers. A layer may be a net positively charged layer, a net negatively charged layer or an essentially neutrally charged layer. In a preferred aspect, the positively charged layer comprises an osmium derivative, a ruthenium derivative, a ferrocene derivative, a positively charged protein or a combination thereof. In another preferred aspect, the negatively charged layer comprises a negatively charged protein, such as for example, glucose oxidase. The positively or negatively charged protein or agent may provide the net positive or negative charge to the layer, respectively. Thus, for example, a layer that comprises a negatively charged protein may have a net negative charge because of its negatively charged protein content.

In certain aspects, the composition is shaped into a pattern, particularly to aid in the conveyance of information upon binding of an analyte to the composition, or to enhance sensitivity of analyte detection. The layer may be any shape, but recognizable symbols such as numbers, letters, geometric shapes, such as circles, squares, stars, and the like are preferred. In another aspect, the composition comprises a central body of hydrogel material. In another aspect, the composition comprises more than one body of hydrogel material. The more than one body of hydrogel material may be placed in multiple locations to form a pattern. In a particularly preferred aspect, the hydrogel is patterned as an array. The hydrogel matterial may be placed on a substrate or mold to aid its retention of shape or pattern. In certain preferred aspects, at least one arm of hydrogel material extends from central body of material. In a particularly preferred aspect, the least one arm comprises the analyte sensitive material. Such a configuration of projecting hydrogel material may enhance the speed and sensitivity of the analyte sensitive compound in detection of an analyte by aiding the ability of the material to contact the analyte.

The invention also provides a composition comprising an analyte sensitive detection system comprised within a hydrogel, wherein the hydrogel material includes but is not limited to, poly(ethylene glycol), poly(ethylene glycol)-co-anhydride, poly(ethylene glycol)-co-lactide, poly(ethylene glycol)-co-glycolide, poly(ethylene glycol)-co-orthoester, poly isopropylacrylamide, polyHEMA, polyacrylamide, sodium alginate or a combination thereof. The analyte sensitive detection system produces an optical or an electrochemical change upon contact with a selected analyte. In a preferred aspect, the hydrogel comprises polymerized poly isopropylacrylamide, polymerized poly(ethylene glycol) or sodium alginate.

In certain embodiments, the analyte sensitive detection system comprises an enzyme, such as glucose oxidase, galactose oxidase, cholesterol oxidase, cholesterase, lactate oxidase, lactate dehydrogenase or bilirubin oxidase, with glucose oxidase being preferred in certain aspects. Organophosphatase(s) are preferred enzymes to detect chemicals associated with chemical weapons. Paraxaon, sarin, tabun and samon are preferred organophosphate analytes, associated with chemical weapons, to be detected.

In preferred aspects of the invention, the analyte sensitive detection system produces a fluorescence change upon contact with the selected analyte. In these aspects, the analyte sensitive detection system or the hydrogel is in operable association with at least a first fluorescent label.

In certain aspects of the invention, the analyte sensitive detection system comprises at least a first component, the at least a first component described as an analyte binding component, wherein binding of an analyte to the analyte binding component alters the fluorescence of the analyte sensitive detection system. Depending on the particular system utilized, binding of the analyte to the analyte binding component can either increase or decrease the fluorescence of the analyte sensitive detection system.

In additional embodiments, the analyte sensitive detection system further comprises a second component that binds to the analyte binding component, wherein binding of the analyte to the analyte binding component decreases the binding of the analyte binding component and the second component. In certain aspects, the analyte competes with the second component for binding to the analyte binding component.

In particular embodiments, the analyte binding component comprises a first fluorophore conjugate and the second component comprises a second fluorophore conjugate. In preferred aspects, the fluorescence of the first fluorophore conjugate is quenched by the second fluorophore conjugate, exemplified by systems wherein the first fluorophore conjugate is FITC-dextran and the second fluorophore conjugate is TRITC-concanavalin A.

In particularly preferred aspects of the present invention, the compositions are formulated for implantation into an animal. In certain embodiments, the animal is a human.

The present invention also provides methods of detecting an analyte, comprising contacting a sample suspected of containing the analyte with an analyte sensitive detection system comprised within a hydrogel, wherein the hydrogel includes but is not limited to poly(ethylene glycol), poly (ethylene glycol)-co-anhydride, poly(ethylene glycol)-co-lactide, poly(ethylene glycol)-co-glycolide, poly(ethylene glycol)-co-orthoester, poly isopropylacrylamide, polyHEMA, polyacrylamide, sodium alginate or a combination thereof. An analyte that is detectable by the methods of the present invention may include, but is not limited to, a carbohydrate, a protein, a nucleic acid, a lipid, a gas or a chemical. Among the preferred analytes detected in the methods of the present invention are glucose, galactose, cholesterol, lactate, bilirubin, a blood gas, urea, creatinine, phosphate, myoglobin or a hormone, such as estrogen or progesterone. In particularly preferred aspects of the invention, the analyte detected is glucose. In other particularly preferred aspects, the analyte is an organophosphate. Organophosphatase(s) are preferred enzymes to detect chemicals associated with chemical weapons. Paraxaon, sarin, tabun and samon are preferred analytes, associated with chemical weapons, to be detected.

In certain aspects, the analyte sensitive detection system produces an electrochemical or optical change upon contact with the analyte. In a preferred aspect, the analyte sensitive detection system produces a fluorescence change upon contact with the analyte. In some aspects, the analyte sensitive detection system comprises at least a first component, the first component further described as an analyte binding component. In other aspects, the analyte sensitive detection system further comprises at least a second component. In additional aspects, the analyte binding component comprises at least a first fluorophore conjugate. In further aspects, the second component comprises at least a second fluorophore conjugate. In a preferred aspect, the fluorescence of the first fluorophore conjugate is quenched by the second fluorophore conjugate. In a particularly preferred aspect, the analyte is glucose, the first fluorophore conjugate is FITC-dextran and the second fluorophore conjugate is TRITC-concanavalin A.

In certain aspects, the sample suspected of containing the analyte is comprised within an animal. In this aspect, the analyte sensitive detection system may be formulated for implantation into an animal.

The invention further provides a method of using a smart tattoo, comprising implanting below the surface of the epidermis of the animal a smart tattoo comprising a hydrogel and an analyte detection compound, wherein the hydrogel comprises a polymerized material including but not limited to poly(ethylene glycol), poly(ethylene glycol)-co-anhydride, poly(ethylene glycol)-co-lactide, poly(ethylene glycol)-co-glycolide, poly(ethylene glycol)-co-orthoester, poly isopropylacrylamide, polyHEMA, polyacrylamide, sodium alginate or a combination thereof, and wherein the smart tattoo is implanted between about 0.05 mm and about 4 mm below the surface of the epidermis of the animal. As used herein certain embodiments, a "smart tattoo" refers to a hydrogel and an analyte detection compound that may be implanted in the epidermis or dermis of an animal.

The epidermis may vary in thickness depending upon its location and the animal, but is generally up to about 1 mm thick in a human. When implanted in the epidermis, it is preferred that the tattoo is placed or implanted of from about 0.05 mm, about 0.06 mm, about 0.07 mm, about 0.08 mm, about 0.09 mm, about 0.1 mm, about 0.12 mm, about 0.14 mm, about 0.16 mm, about 0.18 mm, about 0.2 mm, about 0.22 mm, about 0.24 mm, about 0.26 mm, about 0.28 mm, about 0.3 mm, about 0.32 mm, about 0.34 mm, about 0.36 mm, about 0.38 mm, about 0.40 mm, about 0.42 mm, about 0.44 mm, about 0.46 mm, about 0.48 mm, about 0.50 mm, about 0.52 mm, about 0.54 mm, about 0.56 mm, about 0.58 mm, about 0.6 mm, about 0.62 mm, about 0.64 mm, about 0.66 mm, about 0.68 mm, about 0.7 mm, about 0.72 mm, about 0.74 mm, about 0.76 mm, about 0.78 mm, about 0.80 mm, about 0.82 mm, about 0.84 mm, about 0.86 mm, about 0.88 mm, about 0.90 mm, about 0.92 mm, about 0.94 mm, about 0.96 mm, about 0.98 mm, to about 1 mm below the outer surface of the epidermis of an animal. In another preferred aspect, the smart tattoo is implanted between about 0.1 mm and about 0.25 mm below the surface of the epidermis of the animal. In a particularly preferred aspect, the smart tattoo is implanted about 0.15 mm below the surface of the epidermis of the animal. Preferred animals include sheep, goats, cats, dogs, birds, cows, horses or pigs. A particularly preferred animal is a human.

When implanted in the epidermis of an animal, the smart tattoo may exist only days or weeks before the cells containing or surrounding the tattoo are shed from the animal. In this embodiment, the tattoo will exist up to about 2 weeks before removal through natural replacement of epidermal layers.

In another embodiment, the tattoo is implanted in the dermis or dermal layers of an animal. The dermis may vary in thickness depending upon its location and the animal, but is generally from about 1 mm to about 4 mm thick in a human. The dermis is located beneath the epidermis, often generally beginning about 1 mm beneath the outer surface of the epidermis. The dermis does not actively shed, so that a tattoo may exist semi-permanently or permanently in an animal, i.e. remain in the dermis for months or years. Depending on the thickness of the epidermis and dermis, in certain embodiments, the tattoo may be implanted or placed in the dermis of from about 1 mm, about 1.1 mm, about 1.2 mm, about 1.3 mm, about 1.4 mm, about 1.5 mm, about 1.6 mm, about 1.7 mm, about 1.8 mm, about 1.9 mm, about 2 mm, about 2.1 mm, about 2.2 mm, about 2.3 mm, about 2.4 mm, about 2.5 mm, about 2.6 mm, about 2.7 mm, about 2.8 mm, about 2.9 mm, about 3 mm, about 3.1 mm, about 3.2 mm, about 3.3 mm, about 3.4 mm, about 3.5 mm, about 3.6 mm, about 3.7 mm, about 3.8 mm, about 3.9 mm, about 4 mm, about 4.1 mm, about 4.2 mm, about 4.3 mm, about 4.4 mm, about 4.5 mm, about 4.6 mm, about 4.7 mm, about 4.8 mm, about 4.9 mm, to about 5 mm beneath the outer surface of the epidermis. In certain preferred embodiments the tattoo would be implanted of from about 1 mm to about 5 mm beneath the surface of the epidermis, with 2 mm to about 3 mm being particularly preferred.

When implanted in tissues, the composition may be taken into a cell or remain external to a cell. The particle size of the composition, and its size ratio to that of the size of an adjacent cell will determine whether the composition is taken into a cell or remains external to the cell. In certain embodiments wherein the composition is implanted adjacent to epidermal and dermal cells, compositions of an average particle size up to about 10 microns in diameter or so may be taken into cells. In certain other embodiments, a composition of an average particle size of from about 0.5 microns, about 1 microns, about 2 microns, about 3 microns, about 4 microns, about 5 microns, about 6 microns, about 7 microns, about 8 microns, about 9 microns, to about 10 microns or so may be taken into cells. In certain embodiments, it is preferred that the composition is taken into a cell to measure the intracellular concentration of an analyte. For example, intracellular glucose levels may vary more relative to plasma glucose concentrations in diabetics. Detection of low intracellular glucose levels may aid in monitoring changes in glucose in diabetes or the effectiveness of medications.

In certain other embodiments, it is preferred that the composition remains external to the cells of the tissue that the composition is implanted. A larger average particle size is preferred for the composition in this embodiment, to prevent the composition's uptake by cells. In certain embodiments for epidermal or dermal cells, a composition greater than about 10 microns in average particle size diameter is preferred. In certain embodiments, a composition of about 10 microns, about 11 microns, about 12 microns, about 13 microns, about 14 microns, about 15 microns, about 16 microns, about 17 microns, about 18 microns, about 19 microns, about 20 microns, about 22 microns, about 24 microns, about 26 microns, about 28 microns, about 30 microns, about 35 microns, about 40 microns, about 45 microns, about 50 microns, about 55 microns, about 60 microns, about 65 microns, about 70 microns, about 75 microns, about 80 microns, about 85 microns, about 90 microns, about 95 microns, about 100 microns, about 110 microns, about 120 microns, about 130 microns, about 140 microns, about 150 microns, about 160 microns, about 170 microns, about 180 microns, about 190 microns, about 200 microns, about 225 microns, about 250 microns, about 275 microns, about 300 microns, about 350 microns, about 400 microns, about 450 microns, about 500 microns, about 550 microns, about 600 microns, about 650 microns, about 700 microns, about 800 microns, about 850 microns, about 900 microns, about 950 microns, about 1 mm, about 1.1 mm, about 1.2 mm, about 1.3 mm, about 1.4 mm, about 1.5 mm, about 1.6 mm, about 1.7 mm, about 1.8 mm, about 1.9 mm, to about 2 mm or more average particle size is preferred.

Of course, different analyte detection compounds may be combined with different particle sizes in various combinations. In one embodiment, particles of one average sized diameter may detect a different analyte than another composition with a different average particle size diameter. Alternatively, detection compounds that detect the same analyte may comprise compositions of functionally similar size. In certain embodiments, a different optical and/or electrochemical detection agent comprises the analyte detection compound. Thus, by combining various particle sizes with different analyte detection compounds, composition with different detection properties may be created. For example, fluorescence at one wavelength in a composition with an average particle size less than about 10 microns may denote the presence of a certain concentration of an analyte in the intracellular spaces, while fluorescence at a different wavelength in a composition with an average particle size greater than about 10 microns may denote the concentration and the intercellular spaces of a tissue. In another example, the composition may comprise more than one analyte detection compounds to detect different concentrations of an analyte, and/or different analytes.

In certain aspects, the smart tattoo may detect an analyte that may include, but is not limited to a carbohydrate, a protein, a nucleic acid, a lipid or a gas. In preferred aspects, the analyte is glucose, cholesterol, lactate, bilirubin, a blood gas, urea, creatinine, phosphate, myoglobin or a hormone. In a particularly preferred aspect, the analyte is glucose. In a preferred aspect, the smart tattoo produces an electrochemical or an optical change upon contact with the analyte. A preferred optical change is a fluorescence change upon contact with the analyte.

In certain aspects, the smart tattoo comprises at least a first component, the first component further described as an analyte binding component In additional aspects, the smart tattoo further comprises at least a second component. In a preferred aspect, the analyte binding component comprises at least a first fluorophore conjugate. In another preferred aspect, the second component comprises at least a second fluorophore conjugate. In certain aspects, the fluorescence of the first fluorophore conjugate is quenched by the second fluorophore conjugate. In a particularly preferred aspect, the analyte is glucose, the first fluorophore conjugate is FITC-dextran and the second fluorophore conjugate is TRITC-concanavalin A.

The efficiency of detection of an optical change in an analyte is dependent upon the wavelength of light used to visualize the composition. Shorter wavelengths, such as the near UV to blue part of the spectrum, i.e. about 350 nm to about 450 nm, are preferred to detect optical changes in a composition implanted up to about 0.4 mm beneath the surface of the epidermis. Longer wavelengths may penetrate deeper into tissue, and wavelengths of the yellow-orange-red-near infrared part of the spectrum, i.e. greater than about 450 nm to about 2 mm or greater, are preferred to detect optical changes in a composition implanted up to about 2 or about 3 mm beneath the surface of the epidermis. In certain embodiments, compositions may be created that are normally be invisible to the naked eye without illumination with a light source, detection with one or more electrodes, or fluorescence or phosphorescence of the composition.

In certain embodiments, the analyte sensitive detection system produces an electrochemical change upon contact with the analyte, while in other embodiments, the analyte sensitive detection system produces an optical change, for example a fluorescence change, upon contact with the analyte. In a preferred embodiment, the hydrogel wherein the analyte sensitive detection system is contained or attached is in contact with a substrate, such as for example, an electrode.

In particular aspects, the analyte sensitive detection system comprises at least a first component, the first component further described as an analyte binding component, while in additional aspects, the analyte sensitive detection system further comprises at least a second component. In certain embodiments, the analyte binding component comprises at least a first fluorophore conjugate. In other aspects, the second component comprises at least a second fluorophore conjugate. In particularly preferred aspects of the invention, the fluorescence of the first fluorophore conjugate is quenched by the second fluorophore conjugate, exemplified by embodiments wherein the analyte is glucose, the first fluorophore conjugate is FITC-dextran and the second fluorophore conjugate is TRITC-concanavalin A.

In preferred embodiments of the present invention, the sample suspected of containing the analyte is comprised within an animal. In further preferred embodiments, the analyte sensitive detection system is formulated for implantation into an animal. In certain embodiments, the animal is a human.

Following long-standing patent law convention, the word "a" and "an" mean "one or more" in this specification, including the claims.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 9A. Schematic of exemplary bench-top fluorescent system including a xenon source, collimating optics, excitation wavelength filter, the tissue, collection optics (optical grating and CCD array may be substituted with wavelength filters and PMT's or photodetectors)) for collection. In addition, input and output polarizers can be added to provide a better correlation. FIG. 9B. Schematic of the chemical structure of a PEG-co-allyl amine gel comprising ConA. In the schematic shown in FIG. 9A, these particles are shown in contact with the interstitial fluid of the dermis.

FIG. 15. Schematic for buildup of multilayer films.

FIGS. 16A and B. Sectional view of hydrogel microspheres. FIG. 16A depicts a cross section of a hydrogel microsphere that contains hydrogel material throughout the body of the sphere. FIG. 16B depicts a cross section of a hollow microgel sphere. The core of the hollow microsphere may be filled with liquid or a gas. Hydrogel material is represented by shaded regions.

FIG. 17A depicts a layer of hydrogel material. FIG. 17B depicts hydrogel material as plurality of layers in contact with each other. Each layer may be charged or uncharged, and may be covalently attached to a successive layer, or physically placed adjacent to a succeeding layer. FIG. 17C depicts a multiple layers of hydrogel material (shaded), wherein one layer is in contact with a non hydrogel substrate (solid). FIG. 17D depicts multiple hydrogel coated electrodes (10). A counter electrode (20) and a reference electrode (30) are in the medium adjacent to the hydrogel coated electrodes. The electrodes detect a current produced upon detection of an analyte by the hydrogel construct. FIG. 17E depicts a hydrogel layer (shaded region) with an optical detection device, such as a photoelectric cell, embedded in the body of hydrogel material. The photoelectric cell (hatched region) produces an electric current upon stimulation with light produced when the hydrogel composition fluoresces upon detection of an analyte.

DESCRIPTION OF ILLUSTRATIVE EMBODIMENTS

Figure 1:
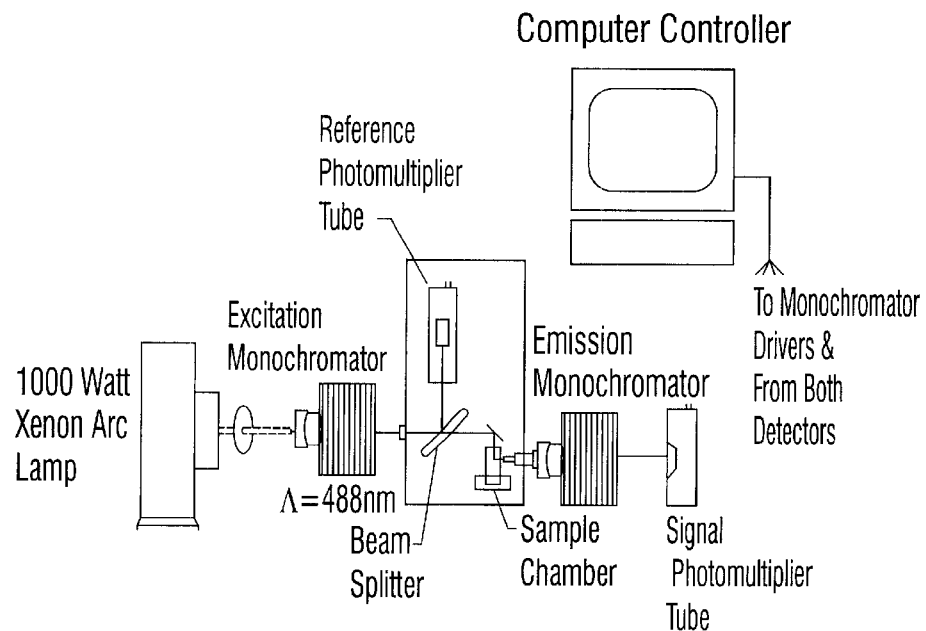
FIG. 1. Exemplary optical system for fluorescence measurements.

The present invention provides novel compositions, methods and devices comprising chemically sensitive particles for measuring analytes including, but not limited to, glucose, cholesterol, lactate, bilirubin, blood gases ($pO_2$, $pCO_2$, pH), urea, creatinine, phosphate, myoglobin, and hormones such as lutenizing hormone. Sensors based upon biorecognition molecules (e.g., enzymes, antibodies, receptors, oligonucleotides) coupled to microelectronic or optical transducers, otherwise known as biosensors, can be applied to needs in medicine, environmental and defense related monitoring, and in the biotechnology industry.

In preferred aspects of the present invention, the compositions or devices are implanted in, through, on or under the skin in order to measure these and other analytes in vivo. In addition, the compositions and methods can be used for therapeutic drug monitoring. The present invention also provides novel compositions that are responsive to one or more particular analyte or drug of interest.

The present invention provides compositions for use in analyte detection by a variety of electrochemical methods, or optical methods such as fluorescence. The instant compositions render these techniques more suitable as detection methods because changes in these optical properties in the material result from specific molecular recognition events. Examples include a PEG gel containing immobilized dextran and concanavalin A. When glucose is present, it will displace dextran and result in an expansion of the gel.

The present invention also provides implantable, fluorescent-doped, intradermal polymer transducers that are combined with an optical probe to quantify one or more selected analytes, for example blood glucose levels. The fluorescence-tagged polymer microspheres are injected in, on or below the epidermis, for example about 0.15 mm below the epidermis in a manner equivalent to a tattoo. After implantation, the glucose specific fluorescently tagged polymer, when illuminated, acts as a "smart tattoo" by providing a noninvasive measurement of the fluorescence peaks that are proportional to the glucose concentration. Fluorescein can be probed in living skin, as reported in the setting of intravenous fluorescein injections followed by fluorescence measurements to delineate skin bums.

The polymers used are made from cross-linked hydrogels of poly(ethylene glycol) (PEG) that are stable (insoluble over a specified period of time), nontoxic, and non-antigenic in vivo. Unlike other noninvasive optical approaches, this technique is highly specific to the concentration of one or more particular, selected analyte(s), for example glucose, since in this fluorescence technique the analyte (i.e., glucose) displaces the fluorophore.

The instant "smart tattoo", based on a dermal injection of a glucose-specific fluorescently tagged polymer, combined with an external optical probe, is sensitive and robust enough to repeatably monitor glucose in vivo. The instant non-toxic, longlasting, polymer implants are tagged with the appropriate amount of fluorophore to yield strong signals at physiologic glucose concentrations. The fluorescence returned from the implant through 0.15 mm of a highly turbid medium such as skin tissue can be quantifiably measured.

In the instant fluorescence sensing approach there is a much higher signal-to-noise ratio since the present methods and devices are not throughput limited by small diameter implantable optical fibers. Overall, in the present invention, the lack of specificity of the non-fluorescent approaches is eliminated, as well as the inherent problems of an indwelling fiber probe, thus allowing for repeatable, quantifiable, highly specific, blood glucose measurements both within and between subjects.

The present invention thus overcomes the deficiencies present in the art by providing a variety of chemically sensitive, stable (insoluble over a specified period of time), nontoxic, and non-antigenic hydrogel particles which undergo a measurable change in at least one electrochemical or optical property as a function of interaction with one or more substance(s) to be detected. In preferred aspects of the invention, the hydrogel particles are used as intradermal transducers.

I. Hydrogel Polymers

A. PEG Monomers

The choice of biomaterial to use in the instant hydrogel polymers is very important. This material should be easily processed, for example into microspheres, an array or a coating, must preserve the activity of biomolecules immobilized within the material, must be readily permeable to the analyte or substrate (i.e., glucose), and must not promote any adverse biological responses such as acute inflammation and fibrosis. The preferred materials chosen for the instant hydrogel polymers are based on poly(ethylene glycol) or PEG, a material with demonstrated biocompatibility (Desai and Hubbell, 1991a; Desai and Hubbell, 1991b; Drumheller and Hubbell, 1995).

The primary mechanism of this biocompatibility appears to be the prevention of protein adsorption onto the surface of the material by steric exclusion. PEG-based materials have been studied for a number of years as coatings to improve the biocompatibility of devices such as implanted sensors (Quinn et al., 1995a) and as implantable materials for applications such as prevention of post-surgical wound adhesion (Sawhney et al., 1994). More importantly, however, was the development of PEG-based hydrogels that are highly swollen by water and permeable to hydrophilic compounds such as glucose. PEG hydrogels formed through the photopolymerization of poly(ethylene glycol) diacrylate have been used in applications such as the prevention of restenosis and post-surgical wound adhesions (Sawhney et al., 1994; Pathak et al., 1992; Pathak et al., 1993; Hill-West et al., 1994; Chowdhury and Hubbell, 1996). These materials do not cause thrombosis, emboli formation, acute or chronic inflammation, or an immunological response.

PEG-based coatings have also been used to improve the biocompatibility of implanted glucose sensors, wherein it was demonstrated that these hydrogels were not glucose mass transfer limiting (Quinn et al., 1995b). PEG-based materials have also been used to encapsulate and stabilize biomolecules for both chemical sensing and drug delivery. Encapsulating a protein-based drug in a PEG-hydrogel was shown to control the delivery of the biomolecule for the prevention of restenosis (Chowdhury and Hubbell, 1996). At ambient temperatures, PEG was also shown to stabilize proteins via preferential exclusion of the polymer from the protein surface.

The hydrogel polymers of the present invention can be made from a number of different components or combinations of components, and using a variety of different techniques. The hydrogel polymers of the present invention comprise crosslinked hydrogels of polyethylene glycol (PEG). The PEG modified hydrogels are readily permeable to analytes such as glucose. Lag times for these sensors in vivo (between blood and ISF) are found to be approximately a couple of minutes, as the PEG portion of the sensor is not mass transfer limiting. By copolymerizing PEG macromers with vinyl-containing monomers such as allyl amine or acrylic acid, chemical functionalities can be introduced into the gel that permit the covalent attachment of biorecognition molecules to the polymer network. The gels can thus be covalently tethered with proteins (glucose oxidase, ConA) and/or other biomolecules to allow for fluorescent or other optical sensing. Micro- and nanospheres of these copolymers can be formed by polymerization in combination with emulsification or spray drying. In the spray drying/polymerization process, the gel precursor solution is dispersed in air or nitrogen and the resulting droplets polymerized using UV light. In the emulsion polymerization process, the precursor solution is emulsified in an immiscible solvent and the emulsion polymerized photochemically or chemically.

In certain aspects, the hydrogel material slowly degrades, and new hydrogel material is injected once every year or two, thus reducing the host response to the implant. For degradable materials PEG-co-anhydride hydrogels can be used as well as degradable polyesters such as polylactide, and polyanhydrides such as polysebacic acid. Biorecognition molecules within this polymer are physically entrapped. Micro- and nanoparticles of this material can be formed through a double emulsion technique or through spray drying.

B. Vinyl-Containing Monomers

As described above, PEG-based hydrogels that are highly swollen by water and permeable to hydrophilic compounds are preferred for use in the present invention. One technique to regulate the degree to which the PEG-based hydrogels are swollen by water is through the use of vinyl-containing monomers in conjunction with the PEG monomers. As used herein any monomer containing a reactive any monomer containing a reactive carbon-carbon double bond qualifies as a vinyl containing compound. These comonomers can affect water content by making the gel more or less hydrophilic, or by increasing the crosslinking density in the gel. Additionally, by copolymerizing PEG macromers with vinyl, acrylate- or methacrylate-containing monomers, chemical functionalities can be introduced into the gel that permit the covalent attachment of biorecognition molecules, such as reporter or detection molecules, to the polymer network.

Vinyl-, acrylate- or methacrylate-containing monomers contemplated for use in the present invention include, but are not limited to, acrylic acid, allyl amine, styrene, allyl alcohol, acrylamide, acrylate-PEG-hydroxysuccinimde ester (that can be used, for example, for attaching biomolecules to the gel), Os(vinyl pyridine)(bis-bipyridine)$_2$Cl, and derivatives based on vinyl imidazole, vinyl bipyridine, dimethylbipyridine, dimethoxybipyridine or Ru, vinyl ferrocene, and derivatives based on Os, Ru or methyl pentadiene, and polyacrylated monomers (crosslinking agents), such as trimethyl propane triacrylate and pentaerythritol tetraacrylate, or any combination of these monomers. Preferred derivatives of Os(vinyl pyridine)(bis-bipyridine)$_2$Cl include derivatives that substitute vinyl pyridine with vinyl imidazole or vinyl bipyridine, and/or substitute bis-bipyridine with dimethylbipyridine or dimethoxybipyridine, or substitute Os with Ru. Such derivatives are described in U.S. Pat. Nos. 5,264,104 and 5,264,105, incorporated herein by reference. In certain aspects, hydrophobic comonomers are contemplated for use, and include but are not limited to, styrene, acrylic acid, methacrylic acid, or any alkene, such as, for example, pentene. In other aspects, cationic comonomers are contemplated for use in the present invention, and include but are not limited to, allyl amine or acrylamide. Anionic comonomers are also contemplated for use in certain embodiments, and include but are not limited to, styrene sulphonate. Neutral but hydrophilic comonomers, including but not limited to allyl alcohol are contemplated for use in some embodiments. Comonomers reactive with biomolecules are also contemplated for use in some embodiments, and include but is not limited to, acrylate-PEG-hydroxysuccinimide ester. In some aspects, redox comonomers, including but not limited to, vinyl ferrocene, Os and Ru derivatives of vinyl pyridine and vinylimidazole are contemplated for use in the present invention. Multifunctional crosslinking comonomers, including but not limited to, trimethylol propane triacrylate or pentaerythritol triacrylate are also contemplated for use in certain aspects of the present invention. Of course, combinations of hydrophobic comonomers, cationic comonomers, anionic comonomers, neutral but hydrophilic comonomers, comonomers reactive with biomolecules, redox comonomers or multifunctional crosslinking comonomers are also contemplated in certain embodiments of the present invention.

Copolymers containing n-isopropyl acrylamide also find utility in certain aspects of the invention. These polymers exhibit a lower critical solution temperature (LCST) between 27° C. and 37° C., i.e. they undergo a phase change and solidify at or above the LCST. Thus a biorecognition molecule/polymer solution at 15° C. may be injected where it will subsequently solidify to a solid in vivo. Microspheres can be formed in situ by injecting a solution or suspension of the polymer which will then solidify to micro or nanospheres in vivo. Additionally, isopropyl acrylamide (IPA) can be used alone in a homopolymer. If a copolymer contains IPA, it will exhibit an LCST.

The hydrogel may undergo a phase change when exposed to the analyte, such as glucose, so that the polymer may collapse or change in size. Thus, the free volume of the gel changes as a function of the analyte.

C. Sodium Alginate Copolymers

Sodium alginate is a negatively charged polyelectrolyte copolymer of mannuronic and guluronic acids. The polymer forms an ionicly cross-linked gel in the presence of multivalent cations (frequently calcium ions). Since substances containing phosphates or citrates can destabilize the matrix by chelating the ionic cross-linker, the gel is often stabilized by coating with a positively charged polyelectrolyte like poly(ethylene imine) or poly(lysine). Alginate immobilization has been reported as a mild encapsulation process suitable for fragile components (Seifert and Phillips, 1997). It is contemplated that encapsulation would have no detrimental effect (e.g., denaturing) on binding and detection moeities, such as, but not limited to, Con A lectin.

D. Reporter or Detection Compounds

As described above, through the incorporation of vinyl-containing monomers into the hydrogel particles, chemical functionalities can be introduced into the gel that permit the covalent attachment of biorecognition molecules, such as proteins or other biomolecules, to the polymer network.

In preferred aspects of the present invention, proteins are used as the biorecognition molecules. The proteins can be enzymes, for example oxidoreductases such as glucose oxidase, glucose dehydrogenase, galactose oxidase, lactate oxidase or pyruvate oxidase, that react with one or more analytes or chemical compounds, thereby leading directly or indirectly to detection of the analyte or compound. Detection of analyte is through the electron transfer from the substrate to the enzyme to the polymer to the electrode where a current is generated that is proportional to the analyte concentration. For example, PEG copolymers containing oxidoreductases and immobilized on electrode surfaces to form amperometric sensors is detailed in Example 2 below.

In other aspects of the invention, structural proteins or nucleic acid molecules are incorporated into the hydrogel polymer network. For example, lectins, such as isolectin I or additional glucose-binding lectins such as lentin lectin, pea lectin, goat peripheral blood lymphocyte lectin, and various seed and peanut lectins, or antibodies can be incorporated into the polymer network.

Glucose assays based on fluorescent quenching of fluorophores due to Fluorescent Resonance Energy Transfer (FRET) has previously been successfully developed in an aqueous medium. TRITC-succinyl-Con A and FITC-Dextran have been used to determine physiological glucose concentrations, based upon competitive binding between Con A, dextran, and glucose. In the absence of glucose, TRITC-succinyl-Con A binds with FITC-Dextran, and the FITC fluorescence is quenched. As glucose binds to TRITC-succinyl-Con A, FITC-Dextran is liberated. The resulting increase in FITC fluorescence is proportional to the concentration of glucose. In preferred aspects of the invention concanavalin A (ConA) is incorporated into the polymer. The ConA can be linked to a variety of reporter compounds, including, but not limited to, FITC or TRITC, rhodamine, Texas red, BODIPY dyes, or any dye pair that results in FRET. Established protocols exist for conjugating FITC and TRITC with polysaccharides and Con A lysine residues under benign conditions (Meadows et al., 1991; Glabe et al., 1983), and may be employed by those of ordinary skill in the art in the practice of the present invention.

Additionally, combinations of fluorescent and/or non-fluorescent reporter compounds may be used in combination for FRET fluorescence. These compounds may be combined with an analyte sensitive compound, and used to detect the presence of an analyte upon contact with the analyte sensitive compound by increases, decreases, and/or other changes in the fluorescence of one or more reporter compounds. In one aspect, a second reporter compound is combined with a binding agent that binds to the analyte sensitive compound and/or to the analyte. Binding of the analyte to the analyte sensitive compound may change the amount of binding of the binding agent to the analyte sensitive compound or to the analyte. The change in relative distances of the one or more reporter compound(s) due to changes in the binding configuration of the analyte sensitive compound or analyte to the binding agent may change the amount of FRET between the reporter compound(s). This change is then detected, thereby detecting the presence of the analyte. Such reporter compounds have been described in U.S. Pat. No. 5,342,789 (incorporated by reference), and include fluorescein, rhodamine, NBD N-(7-mitrobenz-2-oxa-1,3-diazol-4-yl), eosin, erythrosis, dansyl, acridine orange. Pairs of fluorescence compounds have also been described, and include fluorescein and rhodamine, NBD N-(7-mitrobenz-2-oxa-1,3-diazol-4-yl) and rhodamine, NBD N-(7-mitrobenz-2-oxa-1,3-diazol-4-yl) and eosin, NBD N-(7-mitrobenz-2-oxa-1,3-diazol-4-yl) and erythosis, fluorescein and eosin, fluorescein and erythrosis, dansyl and rhodamine, or acridine orange and rhodamine.

In one aspect of the present invention, the detection would occur via a change in the optical signal due to a fluorescence shift and/or an increase or decrease in intensity resulting from a pH change in the presence of glucose or other analyte. These approaches include, polarimetry, Raman spectroscopy, absorption spectroscopy and/or optical scattering may be used to sense indirectly the gel collapse due to the increased presence of an analyte, such as glucose and/or the reduction of water in the hydrogel construct. Raman spectroscopy, Surfaced Enhanced Detection (SERS), Resonance Raman, and/or absorption spectospcopy may also be used to directly sense an analyte or analyte derivative (i.e. gluconic acid for glucose).

E. Biodegradable Polymers

As discussed above, in aspects of the present invention involving biodegradable polymers, including but not limited to, PEG-co-anhydride, PEG-co-lactide, PEG-co-glycolide and PEG-co-orthoester hydrogels as well as degradable polyesters such as polylactide, and polyanhydrides such as polysebacic acid. The invention may also include biodegradable polymer linkages including but not limited to, ester or anhydride bonds.

F. Synthesis of Hydrogel Polymers

1. Redox Monomers

In preferred aspects of the invention, photopolymerized redox polymer networks containing both Fe and Os-based redox couples are produced by first synthesizing a polymerizable organometallic complex followed by UV-initiated photopolymerization with PEG-DA. An advantage of this redox polymer synthesis method is that the ratio of co-monomers can be controlled more precisely, a significant advantage over previous methods used to produce redox polymers for biosensors (Gregg and Heller, 1991a; Degani and Heller, 1989).

The redox monomers described below differ in size, hydrophobicity, and electrochemical potential, and subsequently change the electrochemistry of the resulting films and its ability to engage in charge transfer with the enzymes. The present invention provides redox hydrogels with high specificity for enzymes such as glucose oxidase, thus minimizing noise resulting from the oxidation of compounds such as ascorbate and urate. To minimize the electrooxidation of these interfering molecules, the standard potential of the redox monomer is shifted cathodically to potentials where these molecules are no longer oxidized. For example, using dimethoxybipyridine as an osmium ligand was demonstrated to shift the standard potential of Os-based redox polymers to near zero volts (SCE) and thus minimized ascorbate and urate electrooxidation (Taylor et al., 1995).

Photopolymerizable complexes of $[Os(N-N)_2(vL)Cl]^+$ are prepared from $Os(N-N)_2Cl_2$ and isolated as $PF_6^-$ salts, where N—N is 2,2'-bipyridine or 1,10-phenathroline (or their derivatives), and vL is either vinyl pyridine or vinyl imidazole using methods described previously (Kober et al., 1988). Vinyl ferrocene is commercially available and is used without further modification.

2. Synthesis of Polyethylene Glycol Diacrylates

Poly(ethylene glycol) diacrylate (PEG-DA) of molecular weight 500 was used in the initial photochemical fabrication of redox polymer films. By increasing the chain length of PEG-DA, the resulting films will possess more conformational freedom and thus hydrate more rapidly and induce less conformational strain on entrapped biomolecules, minimizing loss in activity. Increased conformational flexibility should also decrease mechanical contractions experienced during photopolymerization and subsequently minimize film distortion. Increased water content in the gels will also serve to increase substrate permeability and decrease sensor response times if mass transfer proves limiting.

Methods used for the synthesis of PEG-DA of differing chain lengths will follow established protocols developed for PEG-based biomaterials (Sawhney et al., 1993; Pathak et al., 1992; Pathak et al., 1993). In brief, polyethylene glycol is reacted at 0° C. with acryloyl chloride in benzene with triethanol amine added. Triethanol amine hydrochloride is removed by filtration and PEG-DA is removed from benzene by precipitation in diethyl ether. PEG-DA macromers of molecular weight 1000, 8000, and 18,500 are synthesized and used in redox hydrogel photopolymerization and sensor fabrication.

3. Acrylate-Modified Enzymes

Glucose oxidase and galactose oxidase can be entrapped in photopolymerized redox polymer films and retain its activity. However, as PEG chain length is increased or cross-linking density lowered to improve biomolecule stability, enzyme leakage from the redox polymer network may occur, resulting in sensor instability. To tether enzyme directly to the polymer network, acrylate-modified enzymes are produced by modifying lysine residues on the enzymes (glucose oxidase has 19) with NHS-PEG-acrylate (alpha-acryloyl, omega-N-hydroxysuccinimidyl ester of polyethylene glycol-propionic base acid molecular wt 3400) (Shearwater Polymers). During the photopolymerization reaction, the acrylate group participates in the radical polymerization, resulting in the tethering of the enzyme to the polymer backbone.

4. Polyanhydrides

Polyanhydrides are synthesized, in a preferred aspect of the present invention, by melt-polycondensation of mixed anhydrides of diacids and acetic acid. A standard protocol for making polyanhydrides is used (Domb and Langer, 1987). Exemplary of a polyanhydride for use in the present invention is a polyanhydride synthesized from a 1,3-bis-(p-carboxyphenoxy)-propane (CPP) mixed anhydride and a sebacic acid mixed anhydride.

CPP is synthesized (Conix, 1966) and purified by extraction with acetone and ether before use. Briefly, a solution of p-hydroxybenzoic acid and sodium hydroxide in water is placed in a three-necked flask which has a stirrer, condenser, and dropping funnel. 1,3-dibromopropane is added, making sure that the contents in the flask are stirred and kept at reflux temperature. After reflux, solid sodium hydroxide is added to the mixture, and reflux is continued. Heating is stopped, and the mixture is left to stand. The white precipitate of the disodium salt is filtered and washed with methanol. The still wet precipitate is dissolved in distilled water. The solution is warmed and acidified with sulfuric acid. The dibasic acid is isolated by filtration from the warm solution, and dried in a vacuum oven.

Next, an aromatic monomers prepolymer, i.e. CPP prepolymer, is synthesized, thus forming a CPP mixed anhydride. The aromatic monomers are refluxed in acetic acid anhydrous, and then the unreacted diacid is removed by filtration. The solution is concentrated and allowed to crystallize. The crystals are immersed in dry ether with stirring to extract traces of acetic anhydride. Then, the 1,3-bis-(p-carboxyphenoxy)propane prepolymer is recrystallized by dissolving the prepolymer in warm dry dimethylformamide, and adding dry ether with stirring. The solution is allowed to crystallize, and the purified prepolymer is washed with dry ether and dried under vacuum over calcium chloride.

Next, the sebacic acid (SA) mixed anhydride is synthesized. SA is recrystallized three times from ethanol prior to use. To form the aliphatic mixed anhydride prepolymers, i.e. sebacic acid prepolymer, the dicarboxylic acid monomers are refluxed in acetic acid anhydride, and excess acetic anhydride is removed to dry under vacuum. The crude prepolymer is recrystallized from dry toluene. The crystals are then immersed in a 1:1 mixture of dry petroleum ether and ethyl ether to extract traces of acetic anhydride and toluene. The pure crystals are dried under vacuum over calcium chloride.

Next, the polyanhydrides are synthesized by melt-polycondensation of mixed anhydrides of diacids and acetic acid. The 1,3 bis(p-carboxyphenoxy)propane prepolymer is mixed with the sebacic acid prepolymer in a glass tube with a side arm equipped with a capillary nitrogen inlet, and the tube is immersed in a heating mantel. After the prepolymers were melted, high vacuum was applied through the side arm. The condensation product, acetic anhydride, was collected in an acetone/dry ice trap. During the polymerization a strong nitrogen sweep with vigorous agitation of the melt is performed. The crude polymer is purified by precipitation in dry petroleum ether from a dichloromethane solution. The precipitate is then extracted with anhydrous ether. When catalysts are used, 2 molar percent of the catalyst is mixed with the prepolymers prior to polymerization. Heterogeneous catalysts are removed from the polymer solution by filtration.

In order to incorporate vinyl groups into the polymer, the anhydride polymer is reacted with thionyl chloride to form acid chlorides at the termini of the polymer. The acid chlorides are then reacted with 2-hydroxyethylmethacrylate to form methacrylate end groups on the polymer. This allows the polyanhydride to photopolymerize along with PEG.

II. Sensors

A. Particles

In various aspects of the present invention, the hydrogel polymers are formulated as particles that are used to detect one or more analytes extracellularly or in certain aspects within a cell. For the more technically demanding applications such as the detection of multiple analytes in vivo or chemical weapons detection require a high density of sensing elements which themselves contain a large concentration of a given biorecognition molecule. In addition, these sensing elements should be fabricated easily at spatially distinct and addressable regions on a discrete portion of a surface. For the detection of organophosphate chemical weapons, the enzyme phosphotriesterase may be used to produce the pH change. Organophosphatase(s) are preferred enzymes to detect chemicals associated with chemical weapons. Paraxaon, sarin, tabun and samon are preferred analytes, associated with chemical weapons, to be detected.

In various aspects of the present invention, the materials will be made on the order of microns for extracellular monitoring and sub-microns for intracellular monitoring. An extracellular glucose-sensing particle would give levels very similar or identical to blood glucose. Extracellular monitoring is easily done since particles larger than about 5 micrometers to even a millimeter or more which are larger than primary lysosomes are not taken up by cells.

In an alternative embodiment both intra- and extra-cellular analyte monitoring are done simultaneously by using two particle sizes. For instance, measuring intracellular glucose in diabetic patients is important since the acute problems related to diabetes are correlated to intracellular glucose levels. Too much insulin causes low glucose in both extracellular and intracellular fluid (insulin shock). Too little insulin, or insulin receptor resistance, causes low glucose intracellularly and high glucose extracellulary. Thus information can be gained simultaneously by using two particle sizes: one that is small enough for phagocytosis and one that is too large for phagocytosis. In addition, two particles of the same size but given different biorecognition molecules can be used to measure separate analytes or the same analyte in which one particle is given a biorecognition molecule to act as a reference while the other serves as the signal.

Microspheres are preferred for use in certain aspects of the present invention. One method of making the microspheres is by spraying. The microspheres are made by loading a precursor solution, such as for example (PEG/DMPA/TPT) into a 21 gauge needle. However, any type of spray orifice of about 10 to about 1000 $\mu$M is contemplated as being useful in preparation of microspheres. Air or gas may be sent through the spray orafice via a compressor. The size range or the microspheres is controlled through size of spray orifice, gas flow rate, surface tension of precursor solution, surface area of orifice, contact angle between solution and orifice, and/or size of emulsions. Other polymerization agents: any free radical, anionic or cationic polymerization initiator.

In the present example, the needle is inserted into the airhose from the compressor, to give coaxial flow over the syringe needle. The syringe is loaded on a syringe pump at about 1.5 ml/min at a distance of approximately 10 cm over a mineral oil solution. The air is turned on, the syringe is started, and the UV light is activated. The range of UV light is dependent on photoinitiator, and generally is about 254 nm, 365 nm or in the visible light spectrum. In other aspects of the invention, nanospheres are preferred for use.

B. Electrodes

In certain aspects of the present hydrogel polymers, such as for example poly(ethylene glycol) polymers, are used to form insoluble, water permeable hydrogel films on electrode surfaces. Recognition molecules or enzymes, such as glucose oxidase, can be incorporated into these films, resulting in functional enzyme electrodes. Photoinitiated free radical polymerization of redox polymer hydrogels permits the efficient entrapment of enzymes, such as oxidoreductases, and the transfer of electrons from the enzymatic oxidation/reduction through the gel to the electrode surface. Glucose enzyme electrodes are formed, for example, by dissolving lyophilized glucose oxidase or a concentrated aqueous solution of glucose oxidase into the comonomer/photoinitiator mixture followed by photopolymerization. Glucose enzyme electrodes based on these hydrogels have an excellent extended linear range and good sensitivity. Further details concerning glucose enzyme electrodes are presented in Example 2 below.

A analyte sensor that uses a multilayer buildup approach based upon attraction between oppositely charged species, may also be constructed. Thus, multilayers may be constructed based on cationic layer and anionic layer affinities. Examples of cationic layers include, but are not limited to, Os and Ru based redox polymers. Examples of anionic layers include but are not limited to layers that contain glucose oxidase or other low pI enzymes. Methods of construction include the sequential electrostatic binding between oppositely charged layers. Chemical, photochemical or enzymatic crosslinking can be used to stabilize the multilayers and crosslink each layer to other layers. Example 6 describes the construction of such a sensor using an osmium derivative (cationic) and GOX (anionic).

Self-assembled monolayers (SAMS) are also contemplated as being useful in the construction of analyte detection sensors. These patterned surfaces are formed, particularly using alkane thiols and their derivatives on gold-coated surfaces. SAMs also permit the site specific immobilization and orientation of biomolecules on a surface. SAMs may be used as an adhesion layer for multilayers.

C. Arrays

By illuminating a film of the monomer mixture (10% vinylferrocene, 85% PEG-DA (MW 500), 2.5% pentaeryth-ritol tetraacrylate, and 2.5% initiator) with mid-UV light (365 nm, 20 W/cm$^2$, 1–4 s), an insoluble polymer film is formed. It is contemplated that other percentages of components of the monomer mixtures may work, including about 5% to about 20% vinyl ferrocene, about 10% to about 95% PEG, and about 1% to about 50% GOX. The wavelength and duration of exposure to UV light may also be varied, as would be known to those of ordinary skill in the art.

The polymerized films are rugged and adherent to surfaces such as glass, gold, platinum glassy carbon, palladium and other common electrode materials that would be known to those of ordinary skill in the art. Polymerization under the same conditions occurs when an enzyme, such as glucose oxidase (1:1 glucose oxidase:vinyl ferrocene ratio by mass), is incorporated into the precursor mixture. Glucose oxidase (Type X-S, 5 units/mg) is incorporated as a lyophilized powder.

Redox polymer films are polymerized and patterned using the following process. In brief, a surface is coated with a film of glucose oxidase/polymer precursor as described herein. An aluminum shadow mask containing a pattern of dots of various sizes is placed a few millimeters above the surface and is illuminated with 20 W/cm$^2$ 365 nm UV light for 4 seconds. Portions of the coated surface that were exposed to UV light polymerized.

The present invention provides microsensor arrays for a single analyte and for multiple analytes. In a preferred aspect of the invention, single analyte sensor arrays for glucose, and multianalyte arrays capable of sensing glucose, lactate, and pyruvate are provided. Using redox polymer/enzyme precursor mixtures spin-coated on metallized silicon wafers, a quartz mask with a standard pattern of microlines and angles is used to determine pattern resolution down to the micrometer level. A Carl Zeiss MJ3 photolithography system (340 nm light, 20 mW/cm$^2$) is used for this purpose. Electron microscopy is used to image the patterned films and chronoamperometry is used to determine the ability of these films to sense analyte. Because the sensors consist of arrays, a multichannel potentiostat is necessary to make these measurements. It is contemplated that the microsensor devices may be manufactured using any technique known to those of ordinary skill in the art, such as for example, microcontact printing or inkjet printing.

In another preferred aspect of the present invention, a glucose redundant sensor array is provided. Using conventional silicon microsensor fabrication methods, an array of microelectrodes consisting of Au on Cr/SiO$_2$ or on polyimide/Si is produced. The redox polymer/glucose oxidase precursor mixture is spin-coated over the wafer, a quartz mask aligned to the array, and the film patterned. The wafer is washed, diced, wire-bonded, and each sensor tested. In the case of polyimide/Si, the polyimide coating is removed after fabrication to yield a flexible sensor. In both cases the final device is about 1 mm in width. It is contemplated that the final device will preferably have a width of about 100 microns to about 1 mm.

The invention also provides a small array capable of sensing glucose, lactate, and pyruvate. It is contemplated that any oxidoreductase enzyme, may be used in this embodiment, including but not limited to glucose oxidase, lactate oxidase and pyruvate oxidase. Again, standard silicon microsensor fabrication methods are used to produce a set of three Au microelectrodes on Cr/Si or polyimide/Si. Then, a different precursor mixture for each analyte detection gel is sequentially spin-coated and patterned using an aligned mask to photopolymerize each precursor mixture on a different electrode, followed by removal of the unpolymerized regions by washing between the use of each precursor mixture. The wafer is then diced, and each element of the array tested. Again, the final device is about 1 mm in width, small enough to be implanted in the jugular vein of a rat. The techniques utilized ensure that no "cross-talk" exists in the array, i.e. the glucose electrode responding to lactate, as may possibly occur if washing does not effectively remove the precursor mixture from unpolymerized areas, particularly those previous modified with a different redox hydrogel.

D. Location

In a preferred aspect of the present invention, the particles are retained in the interstitial fluid of the dermis or between the dermal/epidermal junction. Surgical methods to place the particles within optical reach of the skin surface (less than about 1 mm deep) are used. It is known that only a small lag-time exists between interstitial fluid of the dermis and serum in blood vessels. An alternative embodiment would include other implantation sites.

Once injected intradermally, i.e. into the epidermal-dermal junction, the microspheres will not be exposed to blood but will rather be exposed to interstitial fluid. The relationship between interstitial fluid glucose and glucose in venous or capillary blood has been the subject of considerable research. Early studies using implanted absorbent wicks indicated that the glucose concentration between interstitial fluid and blood is identical (Bruckel et al., 1989; Fischer et al., 1987; Fischer et al., 1989). However, later human studies using implanted sensors, microdialysis probes, or ultrafiltration probes indicated that interstitial glucose was between 50% and 70% of the concentration in blood (Schmidt et al., 1993). Though interstitial glucose was lower than that in blood, changes in interstitial glucose correlated well with those in blood.

Another issue in the relationship between interstitial and blood glucose is time lag. Mass transfer resistance in the movement of glucose from capillaries to the interstitial space may result in interstitial glucose concentration lagging behind that of blood glucose during periods of dynamic change. This time lag was found to vary from 7 to 10 minutes for subcutaneously implanted glucose sensors (Quinn et al., 1995b). Glucose measurements delayed by a 10 minutes lag are considered clinically relevant and may be used in either open or closed feedback loops for insulin administration.

III. Detection Mechanisms

A. Optical Methods

The present invention contemplates several mechanisms by which a detectable change in optical property of the instant polymers can be achieved, including, but not limited to, Raman scatter, absorption, scatter, polarimetry, fluorescence, phosphorescence, or any the combination of these. In a preferred embodiment, a combination includes polarimetry.

Optical changes in the instant polymers for probing a given substance of interest can be highly specific for that substance. For example, interaction with glucose but not other ubiquitous biomolecules would ideally be measured in persons with diabetes. However, the invention is useful in cases even when specificity is limited. For example, dynamic changes in diabetes include changes in hydration, pH, and osmolality in addition to changes in glucose, all of which provide useful diagnostic information.

The optical changes produced would include changes in the 350–1200 nm spectral region, ideally in the 600–1200 nm region where light penetrates well into the dermis, and more ideally for a visually-read "smart tattoo" in the 600–700 nm region (red visible light), where few natural competing chromophores exist. Any of the above approaches could be used separately or in combination to add to the robustness of detection.

1. Fluorescence

Emission of fluorescence is sensitive to quenching from binding or energy transfer between the fluorophore and its microenvironment. A fluorophore which interacts with glucose to produce a wavelength shift, lifetime shift, and/or quantum yield changes can be used.

Optical sensors, particularly fluorescence sensors, offer advantages over electrochemical sensors. These include the absence of electrical interferences (magnetic or electrical fields), no analyte consumption, the possibility of multiple measurements using optical fibers and the possibility of miniaturization. Fiber-optics can be readily adapted for chemical sensing and be fabricated as miniature devices suitable for remote sensing and safe operation in chemical environments. Perhaps more importantly, optical detection of analytes can be accomplished without the use of radioactive tracers, and can minimize the need for sample handling and manipulation. Fluorescence sensing provides the additional advantage of good sensitivity, with the specificity being obtained from either the properties of the fluorophore or its fabrication within the sensing element.

a. Fluorescence Intensity

At present, most fluorescence sensors are based on intensity measurements, that is, intensity-based sensing, in which the change of intensity in response to the analyte of interest is measured. These intensity changes can be due to changes in extinction coefficient due to probe ionization, changes in quantum yield of the probe upon analyte binding, or due to inner filtering resulting from the optical density changes of indicators.

The fluorescence intensity measurement depends on the intensity of exciting light, the extinction coefficient and concentration of the probe, the optical density at the excitation and the emission wavelengths, the optical path length, the fluorescence quantum yield of the probe, and the detector sensitivity. The fluorescence intensity can also vary due to light scattering and/or absorption characteristics of the sample.

b. Fluorescence Lifetime

An alternate fluorescent sensor measurement is fluorescent lifetime. The fluorescence lifetime of a sample is the mean duration of time the fluorophore remains in the excited state. Following pulsed excitation, the intensity decays of many fluorophores are single exponential. A variety of molecular interactions can influence the decay time. The excited fluorophore can return to the ground state by the radiative (emission) pathway with a rate $k_r$. The inverse of this rate constant is usually called the intrinsic or radiative lifetime. The radiative decay rate is generally of intramolecular origin, with only a modest dependence on the local environment. Upon binding the analyte the absorption spectrum of the probe in many cases changes (spectral shift and/or change in extinction coefficient), which can result in changes the radiative decay rate and thus affect the fluorescence decay time.

The measured fluorescence lifetime is usually shorter than the radiative lifetime because of presence of other decay rates which can be dependent on intramolecular processes and intermolecular interactions. The measured fluorescence lifetime is given by the inverse of the total rate of dynamic processes that cause deactivation from the excited state. Non-radiative processes can occur with a wide range of rate constants. Molecules with high non-radiative rate values display low quantum yields due to rapid depopulation of the excited state by this route.

There are two widely used methods to measure the fluorescence decay time. These are the pulse or time-domain method and the phase-modulation or frequency-domain method. In the pulse method, one excites the sample with a brief pulse of light, typically shorter than the fluorescence decay time, followed by measurement of the time-dependent decay of the emission. The lifetime can be calculated from the rate of decay. An alternative method is to excite the sample with an intensity modulated light source. The lifetime is then determined by the phase shift of the emission relative to the phase of the incident light. The lifetime can also be determined from the relative modulation of the emission compared to the modulation of the incident light.

Due to the absorption of the fluorescence by the acceptor the donor emission displays a phase angle shift in relation to the excitation, which is dependent on the analyte concentration around the sensor. The excitation and emission are modulated at the same circular frequency. The emission is delayed by the phase angle. The relative amplitude of the variable portion of the emission is smaller than that of the excitation. The phase angle can be used to calculate the lifetime of the fluorophore. The demodulation factor can also be used to independently calculate the lifetime. These phase values are correlated to acceptor concentrations. Values or data at several frequencies can be taken, increasing the precision and/or reliability of the measurements. Another characteristic of lifetime-based sensing is the absolute nature of the measurement and after a one-time calibration, the sensor never needs recalibration. This feature is ideal for an implanted sensor.

c. Fluorescent Resonance Energy Transfer (FRET)

Another mechanism which decreases the fluorescence intensity and decay time is fluorescence resonance energy transfer (FRET). An energy-transfer-based sensor consists of two kinds molecules. Donors can be selected for excitability with inexpensive light sources. Acceptors are selected with an analyte-dependent absorbance that spectrally overlaps the donor fluorescence when added to the sensor. Fluorescent resonance energy transfer (FRET) from the donor to the acceptor will quench the fluorescence and alter both the fluorescence intensity and lifetime. By using the phenomena of fluorescent resonance energy transfer (FRET), the donor need not be sensitive to a particular analyte, and the acceptor does not need to be fluorescent. This energy transfer takes place without the appearance of a photon, and the transfer rate depends primarily on the extent of overlap of the emission spectrum of the donor with that of the absorption spectrum of the acceptor, and the distance between the two. In order for FRET to occur individual fluorophore molecules should be within approximately 100 angstroms from each other and have spectral overlap between emission of the donor and excitation of the acceptor.

An advantage of using fluorescent resonance energy transfer (FRET) as the transduction mechanism is that this interaction can be reliably predicted to occur for any Donor-Acceptor pair displaying suitable spectral overlap. Consequently, Donor-Acceptor pairs may be selected which are suitable for sensing in tissues, which are excited with simple light sources, and which are advantageous for simplicity in design and robustness. While the signal levels will be attenuated by tissue absorption and/or scatter the intensity decays are not significantly perturbed. The time scale of photon migration in tissues is near 200 picoseconds. For such a sensor the donor need not be sensitive to the analyte, and the acceptor typically displays a change in absorption spectrum due to the analyte.

Flourescent resonant energy transfer interactions based on molecular proximity of donor and acceptor molecules is applicable to the fluorophores FITC and TRITC, respectively. Fluorescent quenching of Fluorescein Isothiocyanate (FITC) bound dextran due to Fluorescent Resonance Energy Transfer (FRET) of its donor photons to the acceptor, Tetramethylrhodamine Isothiocyanate (TRITC) bound concanavalin A (Con A), has been demonstrated in solution and enclosed in a dialysis membrane by Schultz and co-workers (Schultz and Meadows, 1993; Schultz and Sims, 1979). Con A is a jack bean lectin which binds to both glucose and dextran. In order to decrease agglutination, Con A is frequently succinylated according to the method first published by Edelman (Edelman et al., 1973).

FITC has an excitation peak centered at 488 nm and an emission peak centered at 520 nm while TRITC exhibits an excitation peak centered at 524 nm with an emission peak centered at 580 nm. These properties give the FITC-TRITC pair the required spectral overlap for fluorescent energy transfer.

Though many donor-acceptor fluorophores are applicable for use in FRET applications, FITC and TRITC are preferred due to the availability of labeling protocols for these dyes. FITC and TRITC are easily conjugated with polysaccharides and lectins. It has been shown that when TRITC-Con A is added to a solution of FITC-Dextran, the binding of the dextran to the Con A results in the required molecular proximity (54 angstroms) for FRET quenching to occur (Schultz and Meadows, 1993).

As further described in Example 4, the absence of glucose greatly reduces the fluorescence due to FITC because the energy that is typically emitted as a photon is readily absorbed by TRITC. When glucose is added to a solution containing FITC-Dextran and TRITC-Con A, competitive binding takes place between the glucose and the dextran for Con A. The glucose displaced dextran results in an increase in the observed fluorescence at 520 nm.

2. Polarimetry

Polarized light has been used for many years to determine the concentration of optically rotatory or chiral molecules, particularly in the sugar cane industry. In this embodiment the polarized light would change as a function of the change in scatter or birefringence of the polymer particles as they change size, shape or orientation with the molecule of interest. This change would be measured, for example, by monitoring specific components of the full 16 by 16 Mueller polarization matrix using a light source, input polarization optics before the sample, such as but not limited to, a quarter waveplate and linear polarizer and output polarization optics after the sample, such as but not limited to, a linear polarizer and quarter waveplate. The light beam may then be detected with a photodiode or photodiode or CCD array. In addition, to increase signal-to-noise ratio, the polarization vector can be modulated before or after the sample using a faraday rotator, pockets cell, or photo-elastic modulator (PEM).

3. Combinations of Fluorescence, Phosphorescence and/or Polarimetry

In one embodiment of the fluorescence probe, which will provide similar information to that of the fluorescent lifetime measurements, is known as fluorescence depolarization. The polarization of fluorescence relative to the excitation source polarization, is a function of both fluorescence lifetime and motion of the fluorophore. If the fluorophore does not move during its lifetime, the fluorescence is highly polarized because the down-transition is spatially oriented with the up-transition. If the probe fluorophore is quenched when bound to ConA, lifetime is lower and motion is restricted, both of which inhibit fluorescence depolarization. The ratio of the fluorescence at two polarization angles thus may be better correlated to the signal than fluorescence intensity alone. The birefringence of the tissue may pose a problem with this approach, particularly in the presence of motion artifact. In one aspect, single detectors will be split to yield a return beam onto two detectors with different polarization orientations and the fluorescence at two polarization angles will be ratioed (initially aligned and crossed linear polarizers) in order to identify whether a better correlation exists, in for example, the TRITC-Con A binding relative to fluorescence intensity alone. This aspect will be particularly particularly useful for detection in the presence of an auto-fluorescent tissue.

4. Scattering

Optical scattering is determined by the size and refractive index of particles in relation to their surrounding medium (see Mie scattering theory in H. C. van de Hulst, 1981). A semi-permeable particle that allows water exchange but excludes larger molecules would undergo size changes and refractive index changes as a function of glucose concentration, and as a function of changes in osmolality associated with diabetes. This change in particle size as a function of the analyte concentration will create a change in the return of scattered light. Using a fiber optic probe, with fibers spaced at known distances apart from each other and the radiation source, this scatter can be quantified. In an alternative embodiment the scattered light can be collected using a diffusely or scattering or mirrored semicircular collector similar to an integrating sphere to collect the scattered light.

5. Raman Scattering

The Raman scattering effect arises when a beam of monochromatic radiation passes through a sample such as glucose which contains molecules that undergo a change in the polarizability as they vibrate. The change in the polarizability manifests itself as a unique spectral signature via Stokes and anti-stokes bands and can be used similar to fluorescence and absorption. The Raman scattered light spectrum from the analyte of interest may be measured using a fiber probe with a laser source excitation fiber or fibers and collection fibers. The light collected may then be passed through a notch filter to remove the Rayleigh scattered excitation light and allow only the Raman scattered photons to be collected using a monochromator and CCD detector array or Fourier Transform interferometric spectrometer. A preferred embodiment for the Raman approach that uses the implanted particles is known as Surface Enhanced Raman Scattering. This embodiment includes metallic particles enclosed within the polymer matrix such as silver or gold that when reactive with the analyte of interest or a byproduct of the analyte (such as gluconic acid as a measure of glucose in the well known reaction of glucose with oxygen in the presence of glucose oxidase). The sensor in this embodiment would consist of glucose oxidase immobilized in a hydrogel on the surface of a thin silver on a polymer substrate film or colloidally as particles. Silver is the metal shown in a number of studies to have the greatest SERS effect. Thus when implanted, glucose from interstitial fluid will diffuse into the gel, be converted to gluconic acid by the enzyme which is then measured noninvasively using the Raman system described above.

6. Absorption

The absorption spectrum and/or cross-section (absorption coefficient) of many chromophores changes with molecular interactions and microenvironment, and can be used similar to fluorescence changes. The absorption spectrum may be measured directly as a function of the analyte concentration but would need to be measured in the overtone and combination band wavelength range (about 0.7 to about 2.5 microns) (such as the glucose bands around about 1.6 and about 2.2 microns) in order to reduce the effect of strong water absorption bands normally found in the infrared wavelength region. The embodiment would include a broad band source for excitation (such as, for example, a Tungston Halogen bulb) either directly or with fiber optic delivery and a series of filters coupled to a detector array used for collection of the light. In an alternate embodiment a series of optical fibers could be used for light collection at different distances from the source to overcome the signal dependence on path length. Although analyte concentrations could be measured directly due to interferences from water other analyses, temperature, and other confounders, in a preferred embodiment the particles would serve to change their light absorption properties as a function of the analyte concentration. Using the absorption configuration described above the analyte detection chemicals entrapped in the particle matrix could change their "color" such as, for example, phenol red dye which reversibly changes with pH in cell culture media.

B. Electrochemical Methods

As discussed above, sensor accuracy and lifetime continue to remain serious challenges. In certain aspects of the present invention, these problems are addressed by using redundant sensors, i.e. multiple sensors that simultaneously monitor glucose. With such an array of glucose sensors, the glucose measurement is derived from the average of the signal resulting from each array element and signal processing algorithms are used to identify array elements that have failed and remove them from the calculation of glucose concentration. Redundant sensor applications require a high density of individual sensing elements to effectively form a miniaturized sensor array. Thus individual groups of biomolecules are immobilized in spatially distinct, addressable regions on a surface.

1. Electrochemical Systems

In addition to optical devices, a number of electrochemical systems have been described to noninvasively quantify blood chemicals. Implantable glucose sensors have been under investigation for nearly three decades, with mixed results. These devices are implanted either in subcutaneous tissue, where they measure glucose associated with interstitial fluid, (Wilson et al., 1992; Csoregi et al., 1994; Koudelka et al., 1991) or are implanted intravascularly (Armour et al., 1989). Though not yet commercially available, these sensors have shown the ability to monitor glucose long-term in animals and monitor glucose in humans as demonstrated by limited clinical trials.

In comparison to noninvasive and minimally invasive techniques, implanted sensors are in direct contact with undiluted, physiological relevant fluids (blood or interstitial fluid). The development of an implantable glucose monitoring technique will very likely result in increased patient compliance with intensive treatment and hopefully will also decrease the frequency of hypoglycemic episodes because of the increased awareness of blood glucose levels. One method of achieving tighter metabolic control is a closed-loop insulin delivery system, incorporating a microprocessor-controlled insulin pump and a glucose sensor.

2. Microelectrodes and Sensor Redundancy

Microelectrode arrays where each array element detects the same analyte have superior properties, such as signal to noise ratio (Weber, 1989), to a single large electrode. Because of radial mass transfer effects, the flux of analyte to microelectrodes is higher than that for a large planar electrode where semi-infinite linear diffusion dominates. If the current at the electrode is mass transfer limited, then the increased rate of mass transfer resulting from the geometry of a microelectrode will result in a higher current density (Pishko et al., 1991). Independently addressable array elements for the same analyte also have the advantage of allowing advanced signal processing techniques to be used to reduce noise and improve the accuracy of the overall sensor. This is particularly useful in medical applications such as an implantable glucose sensor where erroneous results may harm the patient. An early study using two implanted glucose electrodes monitoring simultaneously in the subcutaneous tissue of a rat combined with a signal processing algorithm demonstrated that the overall glucose measurement accuracy could be improved over that of a single sensor (Schmidtke et al., 1996).

Large numbers of redundant sensors allow signal averaging to improve accuracy and the use of fault detection algorithms to detect the failure of individual array elements. For example, the variance of a measurement based on the average of N identical sensors is:

$$\sigma = \frac{\sigma_N}{\sqrt{N}} \quad (1)$$

where $\sigma$ is the variance of the measurement, $\sigma_N$ is the variance of each individual sensor, and N is the number of sensors.

In addition, the reliability of the overall device will increase because of redundancy. If $R_m(t)$ is the average sensor reliability among a group of N sensors (i.e. the number of sensors functioning correctly at time t divide by the total number of sensors), then the reliability of an array of these sensors operating in parallel is:

$$R_s(t) = 1 - [1 - R_m(t)]^N \quad (2)$$

Thus for an array of 4 sensors each with a reliability of 0.75, the reliability of the array is $1-[1-0.75]^4$ or 0.996, a large increase as compared to a single sensor. In the most basic sense, reliability is define as the probability of a component surviving for some period of time t (Modarres, 1993).

The most common metric for reliability is the mean time to failure or MTTF where $$MTTF = \int_0^\infty R(t)dt \quad (3)$$

For many systems, component lifetimes are distributed exponentially, thus $$R(t) = e^{-\frac{t}{\lambda}} \quad (4)$$

where $\lambda$ is the component's mean lifetime. Thus for a single component $$MTTF = \frac{1}{\lambda} \quad (5)$$

and $$MTTF_S = MTTF\left(1 + \frac{1}{2} + \ldots + \frac{1}{N}\right) \quad (6)$$

for a redundant array of identical sensors. As is apparent, the MTTF of the array ($MTTF_s$) increases as the number of components increase. However, there is a diminishing return, i.e. each addition component contributes less to the MTTF. Thus an optimum number of components (or in our case sensors) exists to maximize reliability and minimize cost of the array.

3. Sensor Fabrication

Thick film technology have been used for a number of years to fabricate single biosensors for the home glucose test market, but this technology is not amenable to the fabrication of micrometer scale arrays of sensors. Thus silicon-based microfabrication techniques seem more likely to fulfill the need for microsensor arrays. Integrated sensor Microsystems (Wise and Najafi, 1991) and multichannel microprobes (Leong et al., 1990) can be fabricated using existing technology, however, techniques to reproducibly immobilize biomolecules on these surfaces remain to be developed.

SAMs are easily formed and are conformal to a surface. However, two-dimensional approaches such as SAMs may limit the number of biomolecule recognition sites on the sensor surface and thus may have low signal levels and require shielding or other measures to reduce noise. In addition these devices do not appear robust enough to be implanted. By forming a three-dimensional network containing immobilized biomolecules, the number of recognition sites and as a result sensor signal can be increased. This was recently demonstrated with fabricated DNA sequencing microchips based on oligonucleotides immobilized in arrays of polyacrylamide gel elements (Yershov et al., 1993).

IV. Analytes

The present invention provides methods for the detection of one or more of a variety of different analytes or compounds, and in certain preferred aspects of the invention, the detection of combinations of selected analytes. In a particularly preferred embodiment of the invention, glucose level or concentration is detected by the instant optical or electrochemical detection methods. For example, glucose can be detected utilizing a polymer comprising TRITC-conA and FITC-dextran, or through the use of a glucose electrode comprising an enzyme such as glucose oxidase.

The present invention also provides for the detection of other selected analytes. For example, methods for the detection and analysis of cholesterol (HDL and LDL) are provided, and involve the use of enzymes such as cholesterol oxidase and/or cholesterase used in conjunction with electrochemical detection. The present invention also provides methods for the detection of $O_2$ and NO using the Ru bipyridine and Ru-phenathroline compounds described above.

Furthermore, a variety of hormones can also be analyzed utilizing the present invention. The hormones are detected and quantitated by competitive binding assays using antibodies for hormones with FRET as the detection scheme. Antibodies, both polyclonal and monoclonal, that are specific for hormones such as estrogen, progesterone and thyroxine are well known and available to those of skill in the art, and can be incorporated into polymer networks as described herein.

Other clinically important compounds can also be detected and analyzed using the present invention. For example, lactate can be analyzed using enzymes such as lactate oxidase or lactate dehydrogenase with electrochemical detection, galactose can be analyzed using enzymes such as galactose oxidase, bilirubin can be analyzed using enzymes such as bilirubin oxidase, myoglobin can be analyzed by a competitive binding assay using antibodies for myoglobin with FRET as the detection scheme, and cytokines can be analyzed by a competitive binding assay using antibodies for cytokines with FRET as the detection scheme. For example, an antibody may be attached to one dye, and an antigen may bind to another dye to detect the presence of an antigen using FRET. One example would be anti-alfatoxin M1 rabbit IgG attached to the first dye used to detect the binding of the antigen alfatoxin M1 to the second dye. Dye pairs that are contemplated include any known to those of skill in the art that produce FRET.

V. Detection Devices

The present invention also provides a detection device or monitor to determine the presence and value of one or more substances within a patient. Specifically, the present invention includes an energy source for emitting energy to excite the bio-implant within the patient. Further, the present invention includes a detector to detect energy emitted from the bio-implant. In exemplary embodiments, the detector produces a signal representative of the emitted energy. The present invention also includes a comparator to compare the detected signal to the energy source, and a computation circuit to receive the output of the comparator, from which a value of the substance is determined.

A. Energy Source and Delivery

The present invention includes an energy source to provide energy to excite the sensor or bio-implant. Important factors in selection of an appropriate source include determination of the optimal geometry to yield the highest signal-to-noise ratio (SNR), the compensation for the effects due to tissue optics and the ability to obtain a quick scan to provide for ease of patient use and avoid motion artifacts. The source could include but is not limited both coherent (laser based) source or incoherent (bulb) technology depending on the optical application and wavelength or wavelengths required. These sources can be coupled directly into the sample or can be fiber optically coupled.

Known apparatus implement backscatter-based optical approaches, including fluorescence, in vivo using fiber optic delivery and collection. In addition to using these approaches through epidermal and dermal tissue as described above, these approaches are particularly appropriate for use in remote body locations, such as, but not limited to, the cervix, stomach, prostate, bladder, breast, lung, skin, colon, kidney, testicle, ovary, lung, liver, head and neck, pancreas, bone, spleen, lymph node, small intestine, brain, stomach, thyroid, endometrium, esophagus, bone marrow and blood. In other preferred embodiments of the present invention, bulk optics are used for delivery and collection of the light, particularly those embodiments of the present invention directed to dermal detection systems. Such bulk optics allow for optimal throughput of an incoherent source and thus increase SNR. It is difficult to focus all the energy from a light source, specifically an incoherent one, through an optical fiber which is up to about 1 mm, unless a fiber bundle is used. Providing anti-reflective coatings is also difficult with optical fibers. Thus the use of large diameter (centimeter) bulk optics with anti-reflective coatings for transmitting the light provides greater throughput and hence enhanced SNR.

In an exemplary embodiment, the energy source may be a light source, such as a fluorescent source. Alternately, a laser, xenon, light emitting diode, broad band bulb with a specific wavelength filter placed in front of it, a two photon source, radioluminescent source or upconverting phosphor particles may be used as appropriate energy sources. In particular embodiments, the energy source may be conditioned prior to being output as a source. Specifically, the energy source may be collimated, filtered, polarized, and/or otherwise conditioned.

In operation of an exemplary embodiment, the present invention may use a xenon source with a wavelength filter or a laser. The source would ideally operate at the excitation frequency (i.e. 488 nm for FITC-dextran). The xenon source is a noncoherent bulb which offers the flexibility of multiple wavelengths when used with the appropriate filter. However, although the bulb has power on the order of Watts, at the excitation wavelength has much less power (typically microwatts) and is non coherent, thereby reducing the focusing power. The laser (such as an argon, HeNe, or diode laser) typically allows for only one wavelength, but is coherent and much more powerful at the wavelength it provides (i.e. milliwatts to Watts).

The source may then be appropriately conditioned prior to emission to the patient. Specifically, the source may pass through bulk optics such as collimating type lens, a filter, a fiber optic, fiber optic bundle or a polarizer. A combination of at least two lenses are required for the case of an incoherent source to provide collimation of the light. The focal lengths are such so as to provide a collimated beam on the order of about 1–2 cm diameter. The bandpass filter is used, as described above, to provide the excitation wavelength required and typically allow throughputs of above 50%. The fiber optic or fiber optic bundle such as a silica based fiber is used for remote sensing applications such as an internal body cavity and/or to provide flexibility to get to the sensing site. The ideal fiber also has a good dynamic wavelength range to allow for transmission and reflectance of the excitation and emission light, low impurities thereby minimizing auto-fluorescence of the fiber itself, and good numerical aperture to allow for maximal coupling. The polarizer may be used to help eliminate auto-fluorescence of the tissue similar to a time resolved approach as described herein below.

In preferred embodiments, the source is collimated and wavelength filtered to produce a quasi-monochromatic beam at the appropriate excitation wavelength for FITC-dextran. In other exemplary embodiments, the excitation frequency may be between about 488 nm and emission at 520 nm. Such ranges of wavelength are more preferably between about 569 and 618 nm to avoid more of the tissue autofluorescence and to get better penetration depths. Such ranges of wavelength are desirable because it is between the 420 nm and 540 nm bands of hemoglobin, and also away from the 460 nm band of bilirubin. A more preferred wavelength range may be to excite above about 560 nm and into the near-infrared range to avoid more of the autofluorescence and to get better penetration depths. In certain embodiments, wavelengths between 600 nm and 1100 nm are preferred.

B. Detector

The invention includes a means of collecting the signal, such as light, from the monitoring site. This could be done using bulk optics such as collimating type lens, beam splitter, a fiber optic or fiber optic bundle. In certain aspects, the invention also includes a means of separating the wavelength specific fluorescent light produced by the analyte effected chemically sensitive particles. This could be done using bulk optics such as a grating or wavelength specific filters. The detector is dependent on the wavelength of the optical approach used could include but is not limited to silicon for the visible (i.e. about 400 nm to about 780 nm), indium-galium-arsenide (InGaAs) for the near-infrared (i.e. about 780 nm to about 2500 nm), extended InGaAs for the near to mid infrared region (i.e. 1200 nm to about 2500 nm), and indium antiminide, lead sulfide, or platinum selicide for the mid -infrared wavelength region (i.e. about 2.5 $\mu$m to 12 $\mu$m or greater).

As discussed above, the energy source is preferably conditioned prior to emission to the bio-sensor. After emission, the energy will pass through the dermis of the patient and be received by the bio-sensor. As discussed above, introduction of the energy source on the bio-sensor will cause an excitation, which will transmit excitation energy from the bio-sensor. Specifically, in an embodiment using a light source, reflected light will exit the bio-sensor.

After exiting the patient, the reflected light will be received by the collection optics of the present invention. In an exemplary embodiment, the collection optics may include a lens and appropriate conditioning elements, such as a polarizer, optical grating or a fiber optic or fiber optic bundle. Then, the conditioned light will be detected, and passed to a processing system, which may be used to determine the level of a particular substance within the patient.

C. Conversion of Light to an Electronic Signal

The invention includes a means of converting the light to an electronic signal. In a particular embodiment, the collection optics includes a lens and polarizer, which receive and polarize the reflected light. The embodiment further includes an optical grating or filters to further condition the incoming light. The lens allows for focusing of the light onto the detector or detector array to provide maximum intensity on the detection element(s). The polarizer helps to eliminate auto-fluorescence. The optical grating or filters are utilized to select the appropriate emission wavelength and/or wavelengths that relate to the concentration of the substance of interest. A interference based spectrometer such as, for example, an FTIR could be used to produce the multiple wavelengths.

Further, the device includes a detector, such as a series of photodetectors or photomultiplier tubes, a photodetector array, a single array, a CCD array, or the like, to detect the incoming light. A single detector such as photodetector or photomultiplier can be cooled either thermoelectrically or with liquid nitrogen to produce a very high detectivity and SNR but can only collect a single wavelength at a time requiring mechanical translation of either the filter or detector to detect multiple wavelengths. The CCD array allows for the collection of multiple wavelengths simultaneously, can be cooled, but typically does not provide the sensitivity of a photomultiplier tube. Use of a detector array allows for the real-time collection of the signal simultaneously at all wavelengths within the band of interest. The detector converts the light signal to electrical signals, which are then passed to the processing system. The electronic signals yield information regarding both light intensity and wavelength as a function of time.

D. Signal Processing

The invention includes a means of processing the electronic signal to generate the analyte concentration or concentrations. This could be done using multivariate statistics or simply using wavelength specific intensity division or subtraction.

The processing system includes circuitry to compare the incoming signals to the original source. The circuitry includes a low noise operational amplifier for increasing the signal strength coming from the detector(s) and an A/D converter to allow for conversion to digital signals that can then be processed under software or firmware control ultimately feeding the analyte concentration value to memory and to a numeric display.

Having multiple wavelengths will provide for post-processing using a partial least squares or other algorithm, if required, in order to correlate the intensity change to analyte concentration. The desired number of wavelengths required is less based on the overall SNR of the return signal in the presence of auto-fluorescent tissue. It should be understood that, for example, when FITC-dextran is displaced from TRITC-Con A by glucose, the fluorescent intensity increases because of quenching in the bound state but a change in the emission or excitation spectrum does not occur. Therefore, two to three wavelengths located at the peak and at the baseline can be identified with the CCD based system and used in certain systems. With a reduction in the number of wavelengths, a system incorporating optical filters and more sensitive single element detector such as a photo-multiplier tube can also be utilized in certain aspects of the invention.

As discussed above, fluorescence intensity per se, may be difficult to quantify because it varies with tissue optics. However, the basic mechanism by which quenching occurs is through a decrease in the fluorescence lifetime, and lifetime measurements are independent of tissue optics. Thus, in aspects of the invention where the 0.25 mm of tissue poses a significant problem, an alternative approach can be used, fluorescence depolarization. The polarization of fluorescence relative to the excitation source polarization, is a function of both fluorescence lifetime and motion of the fluorophore. If the fluorophore does not move during its lifetime, the fluorescence is highly polarized because the down-transition is spatially oriented with the up-transition. If the probe fluorophore is quenched when bound to TRITC-Con A, lifetime is lower and motion is restricted, both of which inhibit fluorescence depolarization. The birefringence of the tissue may pose a problem with this approach, particularly in the presence of motion artifact.

In studies according to the present invention, with the single detectors the inventors will ratio the fluorescence at two polarization angles (initially aligned and crossed linear polarizers) in order to identify whether a better correlation to the TRITC-Con A binding exists relative to fluorescence intensity alone particularly in the presence of other auto-fluorescent tissue.

The following examples are included to demonstrate preferred embodiments of the invention. It should be appreciated by those of skill in the art that the techniques disclosed in the examples which follow represent techniques discovered by the inventors to flnction well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Glucose Detection in vitro

A commercial SPEX Fluorolog spectrometer was used to collect fluorescence spectra from samples containing exemplary fluorescent dyes contemplated for use in the present invention in solution as well as with tagged PEG polymers with added glucose. The samples initially contained the fluorescent-labeled chemicals, FITC-dextran and TRITC- ConA (Molecular Probes, Inc.) along with varying crystalline glucose (Sigma Chemical, St. Louis, Mo.) levels in phosphate-buffered saline solution as described below. The glucose competitively binds with the quenching TRITC-ConA causing an increase in the emission peak of the FITC-dextran.

FIG. 1 depicts an exemplary experimental setup, which includes a visible light source, an excitation monochromator, sample chamber, an emission monochromator, and photomultiplier tubes. The source is a 1000 W Xenon arc lamp, which is coupled into the excitation monochromator through an 8 mm slit. A 1200 grooves/mm grating is used to disperse the light and direct radiation centered at 488 nm on the 200 mm exit slit. A beamsplitter allows monitoring of the excitation light intensity with a reference detector. The excitation radiation is directed to the sample, which is contained within a 1-cm pathlength methacrylate cuvette. Fluorescent light is collected at 90° to the excitation beam and coupled into the emission monochromator through an 8-mm slit. Another 1200 grooves/mm grating disperses the light and centers the wavelengths of interest on a 200 mm exit slit. The grating is rotated under computer control to allow scanning of the 500–600 nm range. A PMT behind the slit counts the photons incident on its face.

To observe the quenching effect of TRITC-conA when bound to FITC-dextran, several mixtures of the chemicals were investigated. First, a solution of 5 $\mu$g/ml of FITC-dextran in phosphate-buffered saline (PBS) was placed in the sample holder its fluorescence spectrum was recorded. Next, a solution containing 5 $\mu$g/ml of FITC-dextran and 667 $\mu$g/ml of TRITC-conA in PBS was generated. This mixture was added incrementally into the sample containing only FITC-dextran, allowing an increase in TRITC-conA concentration while maintaining the FITC-dextran at the original level. During this process, fluorescence spectra were recorded for samples containing different ratios of TRITC:FITC. To observe the competitive binding between FITC-dextran and glucose with TRITC-conA, glucose was dissolved in solutions containing 2.5 $\mu$g/ml of FITC-dextran and 50 $\mu$g/ml of TRITC-conA in PBS. Spectra were recorded for glucose concentrations of 0 mg/dl, 500 mg/dl, and 1000 mg/dl.

Fluorescence spectra, as measured by the flourescence intensity (i.e. photons), of samples with increasing TRITC-conA levels (0, 25 $\mu$g/ml, 50 $\mu$g/ml and 75 $\mu$g/ml) over a range of 500–600 nm was measured. As TRITC-conA levels increased, quenching of the FITC fluorescence signal occured. It was noted that after 75 mg/ml of TRITC-conA (15:1 ratio of TRITC:FITC) there was no further reduction in the FITC-dextran signal.

The quenching effect of TRITC-conA on FITC-dextran fluorescence was measured at the 520 nm wavelength of emission. The relative FITC-dextran fluorescence decreased from 1 to about 0.825 due to the increasing TRITC-conA levels when measured at a ration of 0:1, 1:5, 1:10, 1:15 and 1:20 TRITC-conA:FITC-dextran. The plot showed that quenching of fluorescence reached a plateau at about a ratio of about 1:15 for TRITC-conA:FITC-dextran.

Figure 2:
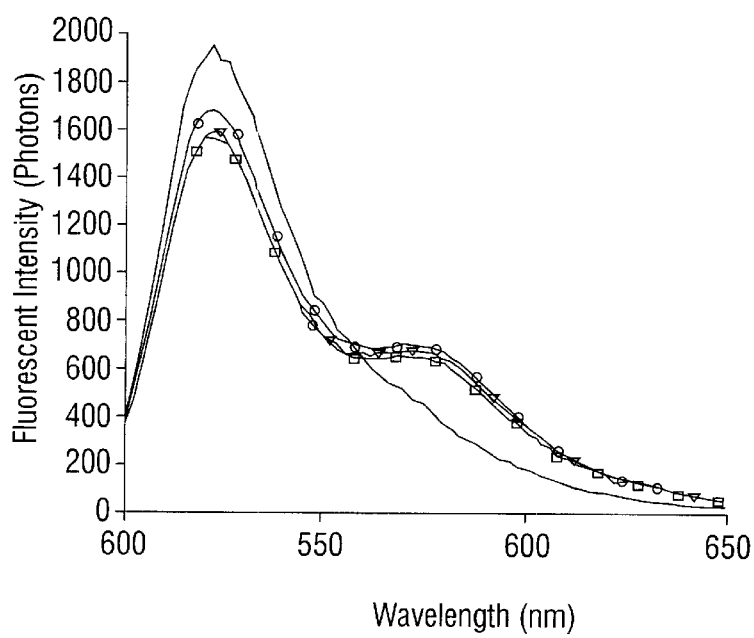
FIG. 2. Competitive binding effect of glucose with FITC-dextran at the 520 nm wavelength of emission. 2.5 µg/ml of FITC-dextran in PBS (-—-), 2.5 µg/ml of FITC-dextran quenched with 50 µg/ml of TRITC-conA in PBS (-□-), competitive binding of 500 mg/dl glucose with 2.5 µg/ml FITC-dextran for the 50 µg/ml TRITC-conA (-▽-) resulted in an increase in fluorescence at 520 nm, an additional increase in fluorescence at 520 nm due to competition of 2.5 µg/ml FITC-dextran with 1000 mg/dl glucose (-○-) for the 50 µg/ml TRITC-conA was seen.

FIG. 2 shows the results of the second study described above. The competitive binding of the glucose is shown to reverse the approximately 20% decrease in the FITC fluorescence due to the TRITC-conA quenching. As the glucose concentration is increased from 0 mg/dl to 500 mg/dl and finally 1000 mg/dl, the fluorescence at 520 nm increases back toward its initial value prior to the addition of TRITC-conA.

Additionally, a polymer containing the fluorescent compounds was synthesized to verify the applicability of the polymer as a fluorescence-labeled glucose monitoring material. Polymer spheres approximately 4 mm in diameter were doped with 200 $\mu$g/ml of FITC-dextran and 200 $\mu$g/ml TRITC-conA and placed in the sample holder. A solution of 0 mg/dl glucose in PBS was added to completely submerge the polymer spheres. After 15 min of submersion, the fluorescent spectra were recorded. The spectra of the spheres were recorded for glucose in PBS solutions of 500 mg/dl and 1000 mg/dl. Between runs the spheres were rinsed in PBS for 15 min and the samples were randomized to eliminate temporal biases.

Competitive binding effect of glucose with FITC-dextran in the polymer spheres was measured by the relative flourescence from 500 to 600 nm with 200 $\mu$g/ml of FITC-dextran in PBS (relative flourescence was about 1 at 520 nm), 200 $\mu$g/ml of FITC-dextran quenched with 200 $\mu$g/ml of TRITC-conA in 4 mm polymer spheres that are submersed in PBS (relative flourescence was about 0.1 at 520 nm), competitive binding of 500 mg/dl glucose-PBS bath with 200 $\mu$g/ml FITC-dextran for the 200 $\mu$g/ml TRITC-conA (relative flourescence was less than about 0.2 at 520 nm), and competition for the 200 $\mu$g/ml TRITC-conA between 200 $\mu$g/ml FITC-dextran and the 1000 mg/dl glucose-PBS solution which bathes the spheres (relative flourescence was about 0.4 at 520 nm). The addition of the glucose released and thus increase the FITC fluorescence at 520 nm due to the competitive binding with the TRITC-conA. In similar fashion to the solutions containing the fluorescent compounds, the fluorescence of the spheres increases as the glucose concentration of the PBS bath is increased from 0 mg/dl to 500 mg/dl and finally 1000 mg/dl.

EXAMPLE 2

Amperometric Biosensors Based on Oxidoreductases Immobilized in Photopolymerized Poly(Ethylene Glycol) Redox Polymer Hydrogels The present example describes the photoinduced free radical copolymerization of vinylferrocene and poly (ethylene glycol) diacrylate to form insoluble, water permeable hydrogel films on electrode surfaces. An exemplary recognition molecule, glucose oxidase, was incorporated into these films, resulting in a functional glucose enzyme electrode. Photopolymerization rates, enzyme function, and film electrochemistry were characterized along with the function of the enzyme electrode. A study to demonstrating patterning of these films using photolithography was performed and the resulting patterned arrays characterized by scanning electron microscopy.

The photoinitiated free radical polymerization of redox polymer hydrogels permitted the efficient entrapment of oxidoreductases and the transfer of electrons from the enzymatic oxidation/reduction through the gel to the electrode surface. These hydrogels, based on networks of poly (ethylene glycol) diacrylate and vinylferrocene, were formed by illuminating at 365 nm, 20 W/cm$^2$ a solution of the comonomers and an ultraviolet photoinitiator, 2,2'-dimethoxy-2-phenyl-acetophenone. The kinetics of photopolymerization were characterized using attenuated total reflectance/Fourier transform infrared spectroscopy (ATR/FTIR), which indicated rapid gelation of the comonomers. Electrochemistry of the redox polymer hydrogel indicated reversible oxidation/reduction with a peak anodic potential at 0.217 V (Ag/AgCl). The diffusion coefficient of charge transfer through the fully hydrated gel was measured at $1.0 \times 10^{-12}$ cm²/s at 25° C. Glucose enzyme electrodes were formed by dissolving lyophilized glucose oxidase or a concentrated aqueous solution of glucose oxidase into the comonomer/photoinitiator mixture followed by photopolymerization. Glucose enzyme electrodes based on these hydrogels had an extended linear range of 0–20 mM with a sensitivity of 0.5 $\mu$A mM$^{-1}$cm$^{-2}$. A demonstration of photolithographic patterning of the hydrogels was also performed, using a shadow mask to form mesoscale patterns of approximately 1 mm on a SiO$_2$ surface.

A. Materials and Methods

Reagents. Glucose oxidase (GOX, EC 1.1.3.4, Type X-S, 128 units/mg solid from *Aspergillus niger*) and horseradish peroxidase (HRP, EC 1.11.1.7, Type VI, 290 units/mg) were obtained from Sigma Chemical Co. (St. Louis, Mo.) and were used without further purification. 2,2'-dimethoxy-2-phenyl-acetophenone (DMPA), vinylferrocene, O-dianisidine (3,3'-dimethoxybenzidine), and poly(ethylene glycol) diacrylate (PEG-DA, MW 500) purchased from the Aldrich Chemical Co. (Milwaukee, Wis.), were used as received.

Electrodes. All electrodes used were purchased from Bioanalytical Systems (West Lafayette, Ind.). Gold electrodes had diameters of 1.6 mm each. Prior to application of the redox polymer hydrogels, the electrodes were first polished with 1 $\mu$M diamond polishing slurry on nylon polishing pads, then polished with 0.05 $\mu$m alumina on microcloth pads followed by sonication and water and methanol rinses.

Equipment. The equipment for cyclic voltammetry and constant potential studies included a CV-50 W Voltammetric Analyzer (Bioanalytical Systems), a cell stand, a Ag/AgCl reference electrode, and a platinum counter electrode. The instrument was controlled and data acquired using a Toshiba Pentium PC. Ultraviolet light induced photopolymerization was performed using a 365 nm, 20 W/cm² EFOS Ultracure 100 ss PLUS UV spot lamp. A Spectral Instruments UV-Vis spectrophotometer (Model 420) was used to acquire spectra of FAD within GOX and characterize its activity. Scanning electron microscopy (SEM) was performed using a JEOL T330A electron microscope with a magnification range of 15× to 200,000× and a resolution of 4.5 nm.

Polymer Hydrogel Precursors and Photopolymerization. Polymer hydrogel precursor solutions consisted of PEG-DA, DMPA, and vinylferrocene (e.g., 75 wt. % PEG-DA, 5 wt. % DMPA, and 20 wt. % vinylferrocene). After combining these components, 10 $\mu$l of a concentrated solution of 400 mg/ml glucose oxidase in PBS was added and gently mixed into 90 $\mu$l of the viscous precursor solution. Alternatively, lyophilized GOX powder was added; however, GOX was only partial soluble in the nonaqueous precursor solution and solid GOX "flakes" were apparent in the photopolymerized gels. One microliter of the enzyme-containing precursor solution was then placed on and spread out evenly over the surface of a gold electrode. The resulting film thickness was approximately 100 $\mu$m. The electrode was then illuminated by UV light (365 nm, 20 W/cm²) at a distance of approximately 1 cm for a period of between two to ten sec until complete polymerization had taken place. Similar procedures were used to prepare gels of different compositions.

Enzyme Assays. Enzyme assays were performed to determine the activity of GOX after exposure to increasing amounts of UV illumination. A modified version of an established protocol was used (Frederick et al., 1990). In brief, a 1 ml solution of 10 mg/ml GOX (in 0.1 M PBS) was placed in a 1 cm path length quartz cuvette and irradiated by 20 W/cm², 365 nm UV light in bursts of 60 sec. Thirty micrograms of HRP and an aliquot of concentrated glucose (sufficient to make the resulting solution 20 mM glucose) were added to 3 ml of 0.16 mg/ml O-dianisidine in 0.1 M phosphate buffered saline (PBS). These components were then mixed thoroughly, and 1 $\mu$l of the UV-illuminated GOX solution was added. The production of the colored assay product was monitored as a function of time at 400 nm and activity determined from the linear slope of the absorbance-time plot.

ATR/FTIR. Attenuated total reflectance/Fourier transform infrared spectroscopy (ATR/FTIR) of polymer hydrogel formation was performed using a Matheson Galaxy 5000 FTIR with a ZnSe ATR crystal. ATR/FTIR was used to monitor the disappearance of carbon-carbon double bonds in the wavenumber range of 1630 to 1680 cm$^{-1}$, indicative of carbon-carbon double bond conversion during the free radical polymerization of the gel. Approximately 10 $\mu$l of the polymer precursor mixture was placed upon and spread out evenly over the surface of the ATR crystal to a thickness of approximately 100 $\mu$m. A borosilicate glass plate was placed over the surface of the solution to ensure even distribution and thickness. The sample was then illuminated through the glass plate with 365 nm UV light at 20W/cm² and carbon-carbon double bond conversion monitored with time.

B. Results

Electron transfer between oxidoreductases and artificial electron acceptor/donors (also called mediators) has been studied for a number of years (Cass et al., 1984). In most oxidoreductase-catalyzed reactions, the mediator takes the place of oxygen in the native enzymatic reaction. Using glucose oxidase as an example, two electrons are transferred from glucose to the FAD redox centers of the enzyme. These electrons can then be transferred from FADH$_2$ to the mediator which is then oxidized at the electrode surface producing a current that is directly proportional to the concentration of glucose in solution (see reactions below).

$$\text{Glucose} + \text{GOX(FAD)} \rightarrow \text{Gluconolactone} + \text{GOX(FADH}_2\text{)} \qquad (7)$$

$$\text{GOX(FADH}_2\text{)} + 2M^o \rightarrow \text{GOX(FAD)} + 2M^r \qquad (8)$$

$$2M^r \rightarrow 2e^- + 2M^o \qquad (9)$$

$M^r$ and $M^o$ are the mediator in its reduced and oxidized form respectively. The mediator can be a diffusing small molecule such as ferricyanide, ferrocene and its derivative or hydroquinone. However, the highest current densities and analyte sensitivities were found when the oxidoreductase was coupled to a polymer containing electron acceptor sites. Examples of such redox polymers include copolymers containing Os(bis-bipyridine)$_2$Cl (Pishko et al., 1990a; 1990b) or vinylferrocene (Tatsuma et al., 1994). Electrons from the redox center(s) of the enzyme are then transferred to the redox sites of the polymer, with electron self-exchange between polymer redox sites allowing electron propagation to occur along a polymer chain segment or between chain segments to the electrode surface.

The nature of the interaction between the redox polymer and the enzyme was found to be important for electron transfer between the two macromolecules (Pishko et al., 1990a; 1990b; Katakis et al., 1994). Interactions that were highly electrostatic in nature resulted in high current densities in sensors based on polycationic poly[vinylpyridine Os(bis-pyridine)$_2$Cl-co-vinylpyridinium ethylamine] and polyanionic glucose oxidase. Modification of either the enzyme or polymer such that both macromolecules possessed the same net charge significantly diminished electron transfer rates between the two (Katakis et al., 1994).

Water permeability, polymer chain flexibility, and substrate permeability are additional considerations in the design of a sensor based on oxidoreductase/redox polymer systems. High analyte diffusion rates through the network are necessary to minimize mass transfer limitations in the sensor current and reduce response time. In the case of hydrophilic analytes such as glucose, substrate permeability into the film is directly related to the equilibrium water content in the polymer network. The influence of solvent (i.e. water) on polymer chain flexibility is important for electron self-exchange and propagation of electrons between redox sites on a single chain and between chains. Limitations in chain mobility result in the decreased frequency of collisions between chain segments that are necessary to bring redox sites to within electron transfer distance and allow self-exchange to occur.

Based on these considerations, redox polymer networks were designed that swelled with water, forming a gel that was permeable to substrate. The backbone of the gel was poly(ethylene glycol), a polymer demonstrated in a number of studies to be biocompatible and highly permeable and flexible in water. Photopolymerized poly(ethylene glycol) diacrylate networks of differing molecular weight have been found to be highly swollen by water and to exhibit low protein adsorption (Pathak et al., 1992; 1993; Quinn et al., 1995a). To facilitate electron transfer through these hydrogels and thus make them applicable to amperometric biosensor applications, an electron acceptor/donor, vinylferrocene, was incorporated into the polymer network using an UV-initiated photopolymerization chemistry (Pathak et al., 1992; 1993; Quinn et al., 1995a). In this example, glucose oxidase served as an exemplary recognition molecule and was incorporated into the polymer network by physical entrapment.

Figure 3:
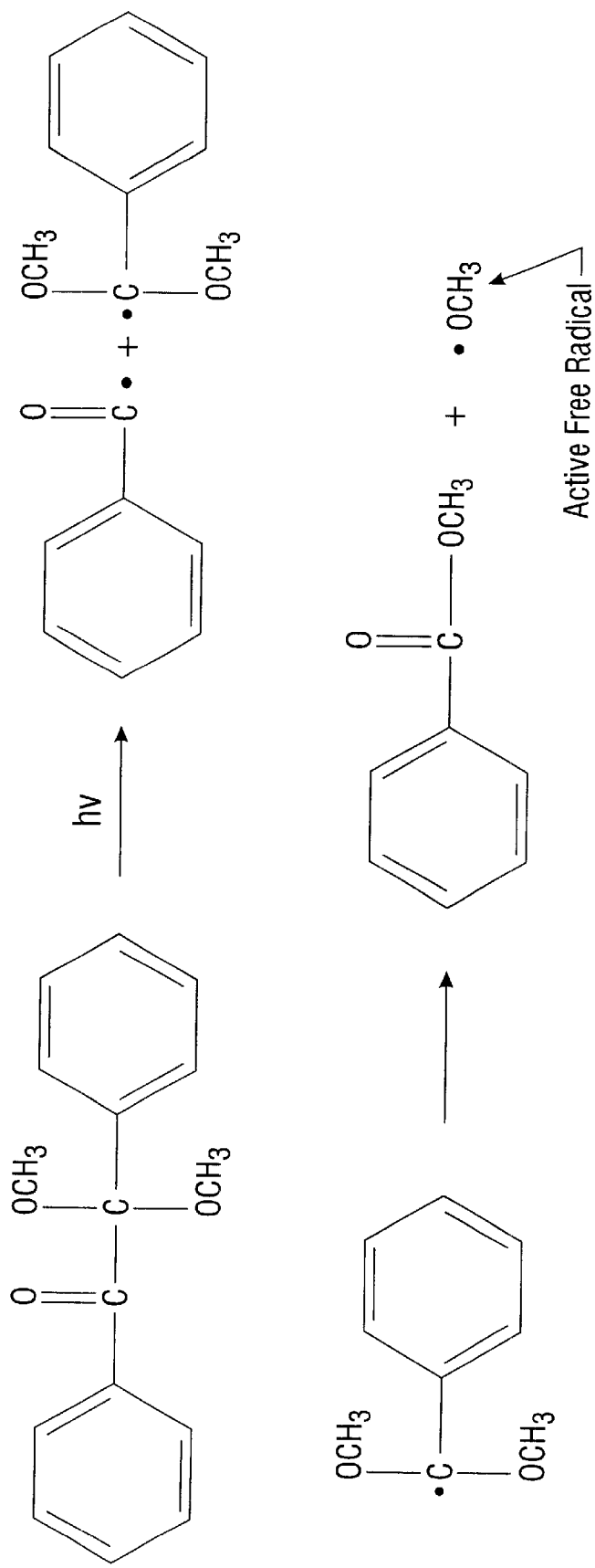
FIG. 3. Photofragmentation of 2,2'-dimethoxy-2-pheylacetophenone.

UV-Photopolymerization/FTIR Characterization. The initiation of photopolymerization via irradiation with UV light is dependent upon the formation of active free radicals. These free radicals may be generated through the use of photoinitiators, which may be classified into two main categories related to their mechanism of free radical formation: photocleavage or photofragmentation (aryl ketones), and hydrogen abstraction (benzophenone, thioxanthone) (Reiser, 1989). The photoinitiator used in this example was 2,2'-dimethoxy-2-phenyl-acetophenone (DMPA) which photofragments in the manner illustrated in FIG. 3 (adapted from Reiser, 1989, incorporated herein by reference).

Figure 4:
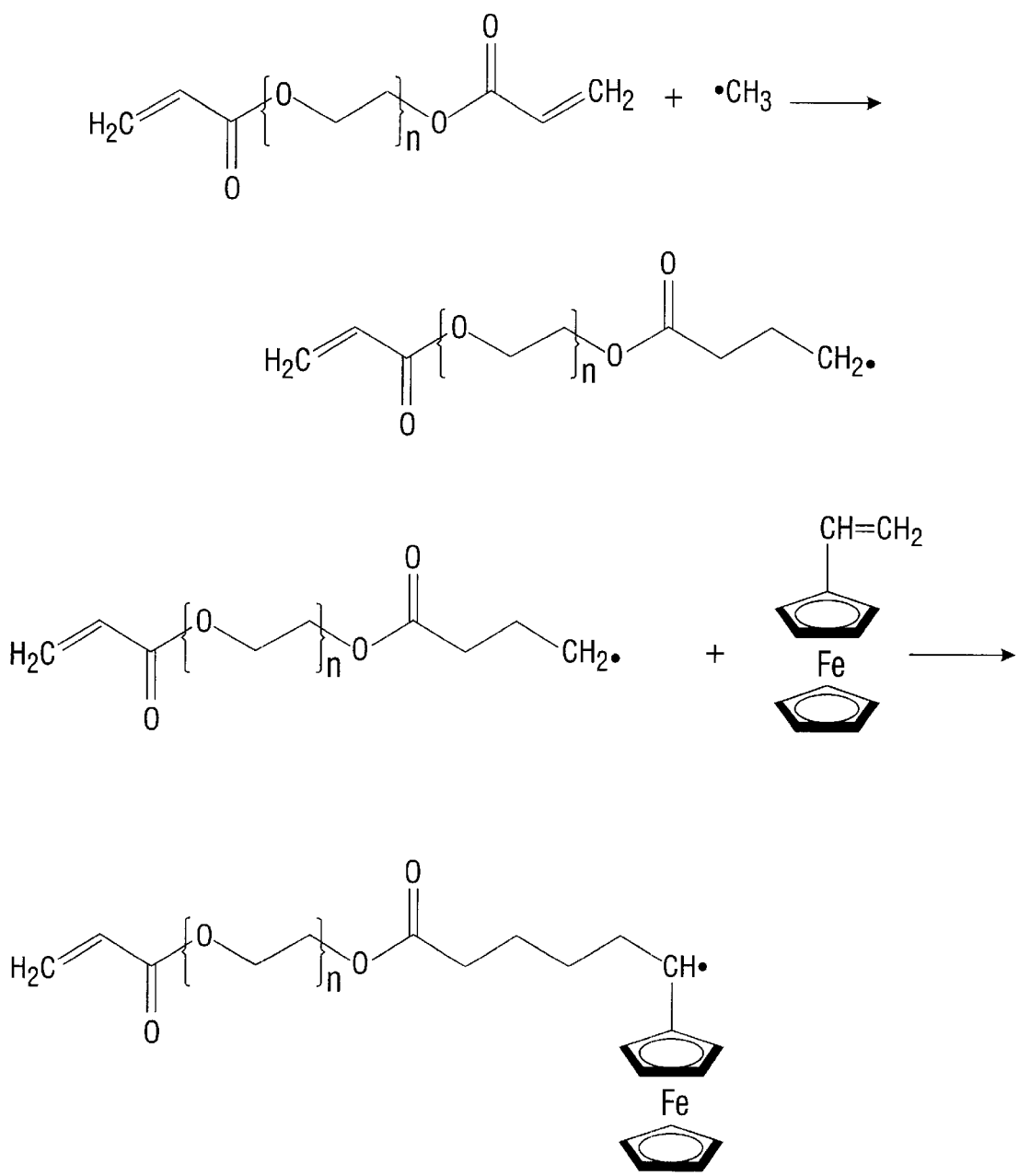
FIG. 4. As depicted the $CH_3$ radical initiates the polymerization of a copolymer network of poly(ethylene glycol) diacrylate (PEG-DA) and acrylated biomolecules by attacking the carbon-carbon double bonds present in the acrylate groups of biomolecules and the acrylate end groups of PEG-DA.
Figure 5:
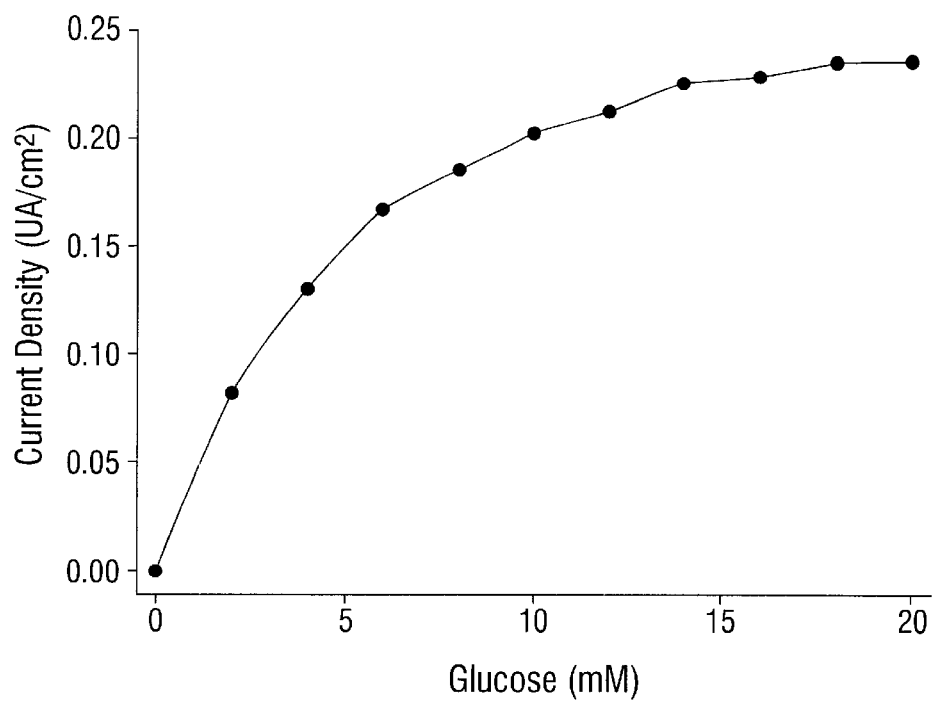
FIG. 5. Glutaraldehyde cross-linked wafers current response to substrate addition. (-•-) Glutaraldehyde X-Linked Wafer.

The $CH_3$ radical formed by photofragmentation of DMPA initiates the polymerization of a copolymer network of PEG-DA and vinylferrocene, as shown below, by oxidizing the carbon-carbon double bonds present in the vinyl groups of vinylferrocene and the acrylate end groups of PEG-DA. The $CH_3$ radical initiation of the polymerization of a copolymer network of poly(ethylene glycol) diacrylate (PEG-DA) and acrylated TRITC-ConA is shown in FIG. 4. This process results not only in linear chain formation but also in branched and crosslinked structures yielding a three-dimensional insoluble polymer network capable of entrapping biomolecules within the structure. It should also be noted that $O_2$ is a free radical scavenger and thus if present in the precursor mixture will result in chain terminations and slow the rate of polymerization.

The resulting polymer films were mechanically stable and did not dissolve in 0.1 M PBS, but the networks were highly permeable and swelled by water. Measurements of the equilibrium water content (EWC) of PEG-DA/vinylferrocene films were performed by placing dried films in 0.1 M PBS overnight and reweighing the swollen films approximately 12 h later. Swelling was determined using Equation 10:

$$EWC(\%) = \frac{Mass(swollen) - Mass(dry)}{Mass(swollen)} \times 100 \qquad (10)$$

Upon complete hydration, the EWC was equal to approximately 15% for films containing 21% vinylferrocene and 79% PEG-DA while the EWC was approximately 30% for films containing less than 5% vinylferrocene, including films containing 100% PEG-DA. Water swelling decreased with increasing concentration of the hydrophobic co-monomer vinylferrocene. It was expected that the EWC to increase upon the oxidation of ferrocene to ferrocenium thus resulting in a polycationic gel and requiring the influx of anions and accompanying water molecules into the gel to maintain charge neutrality.

Using ATR/FTIR the rate of carbon-carbon double bond conversion (i.e. the conversion of the acrylate end groups of PEG-DA and the vinyl group of vinylferrocene) was measured during the photopolymerization processes.

Figure 6:
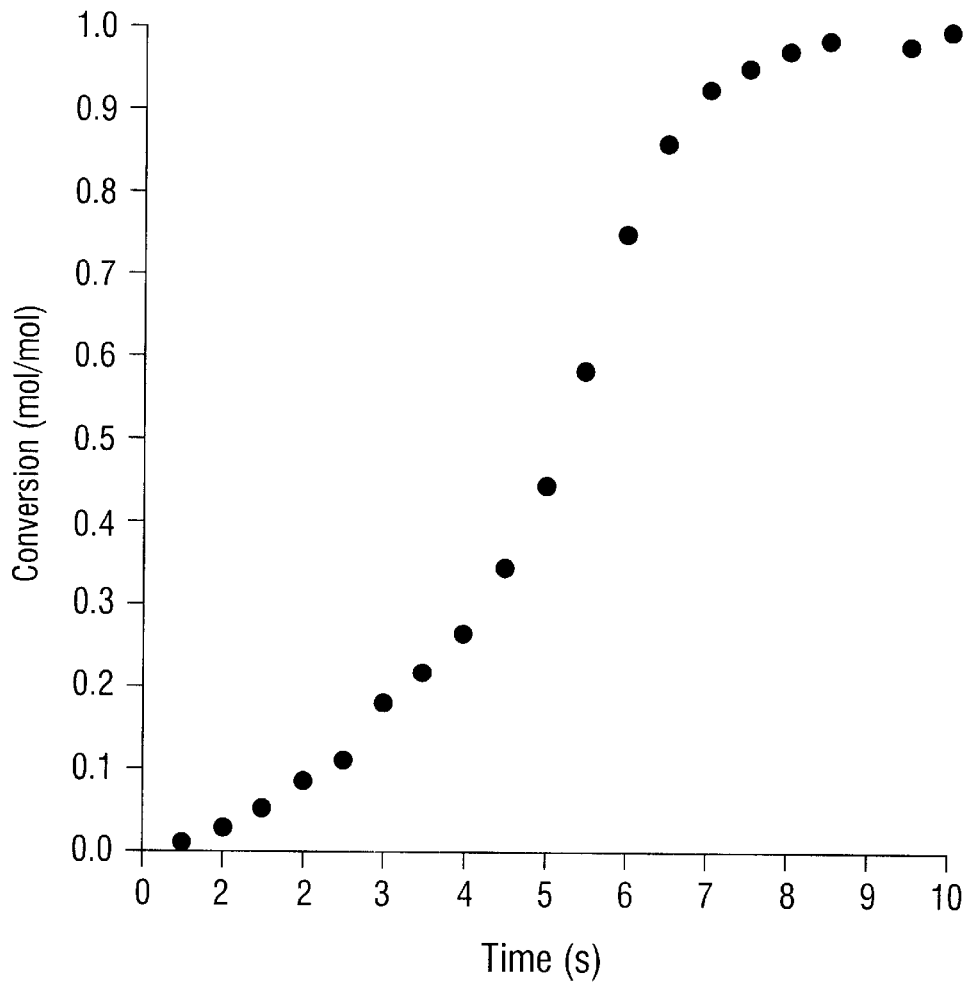
FIG. 6. Carbon-carbon double bond conversion for a PEG-DA (79% wt) and vinylferrocene (21% wt) precursor mixture illuminated with 365 nm UV light at 20 W/cm². 2,2'-dimethoxy-2-phenyl-acetophenone: 50 mg/g of precursor.

The conversion of carbon-carbon double bonds during the photopolymerization of a solution of 75% PEG-DA, 5% DMPA, and 20% vinylferrocene was determined by the increase in transmittance at 1635 cm$^{-1}$. The carbon-carbon double bond conversion for a PEG-DA (79% wt) and vinylferrocene (21% wt) precursor mixture illuminated with 365 nm UV light at 20 W/cm$^2$ for 10 sec. The 2,2'-dimethoxy-2-phenyl-acetophenone was 50 mg/g of precursor. Essentially 100% conversion was achieved within eight seconds. The conversion with time appears sigmoidal in nature (FIG. 6), a likely result of either the thickness of the films studied, the concentration of vinyl ferrocene in the precursor mixture, or the presence of $O_2$ in the hydrogel precursor mixture.

Vinylferrocene is a strong UV absorber at 365 nm with an extinction coefficient measured at 341 L mol$^{-1}$ cm$^{-1}$ (measured using PEG-DA as the solvent). The intensity of UV light reaching the ATR crystal is thus attenuated and as a result photopolymerization at the crystal/solution interface is slowed. For example, 365 nm light UV light was attenuated by approximately 66% by a 100 $\mu$m thick film containing 1.4 moles/liter of vinylferrocene (20% by weight in PEG-DA). When thick films or films with high ferrocene (due to the extinction coefficient) content were tested, most of the ultraviolet light was absorbed at the air-precursor solution interface forming a thin polymer skin layer. Precursor solution underneath the skin polymerized more slowly, depending on the penetration of UV light through the film. This effect can be minimized using techniques such as spin coating that create films with a thickness consistently below about 5 $\mu$M.

A second and perhaps more likely explanation for the slow initial rate of conversion is chain termination by $O_2$. During photopolymerization, the reaction of $O_2$ with the free radical end of a propagating chain results in the formation of a low reactivity peroxy-radical (Krongauz, 1995). In this study, both the preparation of the precursor mixture and the photopolymerization were performed in air. As a result, termination of the free radical polymerization by $O_2$ is highly probable. The rate of conversion increases, however, when $O_2$ in the film is consumed and will result in the kinetic behavior observed in FIG. 6.

Effect of UV Illumination on Glucose Oxidase Activity. Exposure to high levels of ultraviolet light can lead to the irreversible inactivation of biomolecules through the generation of free radicals and their resulting covalent reactions.

In order to determine the time course of GOX deactivation that would likely occur with exposure to high intensity UV light, enzyme assays were performed as described earlier. The assays demonstrated a decrease in absorbance, with GOX losing approximately 60% of its activity during the first minute of continuous exposure to 365 nm UV light at 20 W/cm². Glucose oxidase was dissolved 10 mg/ml in 0.1 M aerated phosphate buffered saline and illuminated through a 1 cm path length quartz cuvette. The times required to affect GOX activity as determined in these inactivation studies, however, were between 15 to 60 times greater than the amount of time required to polymerize a representative 100 μM film on an electrode surface. In the redox polymer network, GOX is somewhat protected from both UV light and free radical attack. The enzyme was incorporated into the polymer film in the presence of a strong UV absorber, vinylferrocene, and a large concentration of free radical scavengers in the form of the acrylate groups of PEG-DA and vinyl groups of vinylferrocene. These molecules should attenuate the intensity of UV light and free radicals reaching the enzyme and thus aid in preserving its activity.

The UV-Visible spectra of the FAD of GOX was also examined since the flavin adenine dinucleotide cofactor of glucose oxidase may be sensitive to UV light, as was observed with other flavins (Ott et al, 1984). UV-Vis spectra were taken of the GOX enzyme solution itself after each dose of UV irradiation. These spectra revealed that the absorption peaks at 382 and 452 nm, representative of FAD in GOX, disappeared slowly upon prolonged exposure to UV light. As expected, decreases in $FAD/FADH_2$ peak intensity coincided with decreases in enzyme activity.

Redox Hydrogel Electrochemistry. The electrochemistry and glucose response of the redox polymer/glucose oxidase network was determined using glucose oxidase/vinylferrocene/PEG-DA films photopolymerized on gold electrodes. After photopolymerization, these electrodes were placed in 0.1 M PBS degassed with nitrogen, and approximately 30 to 60 min was allowed for hydration while cyclic voltammetry from 0 to 0.5 V (Ag/AgCl) of the PEG-DA/vinylferrocene hydrogel on a 1.6 mm diameter gold disk electrode in 0.1 M phosphate buffered saline at 25° C. (Ag/AgCl reference electrode) was performed. The peak anodic potential at a scan rate of 5 mV/s was 0.217 V (Ag/AgCl).

Using a linear regression of peak anodic current versus the square root of the scan rate along with the electron transport model of Randles-Sevcik (Forster and Vos, 1991), which assumes a semiinfinite linear diffusion, $D_{ct}$, or the diffusion coefficient of charge transfer was determined (Equation 11).

$$i_p = \frac{0.4463(nF)^{1.5} A D_{ct}^{0.5} C^* v^{0.5}}{\sqrt{RT}} \quad (11)$$

The terms are defined as follows: $i_p$ is the peak anodic current, n is the number of electrons in the oxidation, F is Faraday's constant, $D_{ct}$ is the diffusion coefficient of charge transfer, C* is the concentration of ferrocene redox centers in the film, v is the scan rate, R is the universal gas constant, and T is temperature. $D_{ct}^{1/2}C^*$, calculated from linear regression of $i_p$ versus $v^{0.5}$, was $1.4 \times 10^{-9}$ moles/(cm² s^{1/2}). This value was nearly identical for that reported in vinylferrocene/acrylamide copolymers (Bu et al., 1995). A concentration of redox centers, C* of $1.4 \times 10^{-3}$ moles/cm³ in the polymerized film (based on the vinylferrocene concentration in the precursor mixture) resulted in a $D_{ct}$ value through the gel of $1.0 \times 10^{-12}$ cm²/s. This value for $D_{ct}$ was approximately 100–1000 times lower than $D_{ct}$ values measured for diffusing mediators in poly(ethylene oxide) films (Geng et al., 1989; Nishihara et al., 1991), including that for PEG-modified ferrocenes in PEG melts (Haas et al., 1995).

The films, however, were not covalently crosslinked and thus the motion of each chain is less restricted. Small molecule mediators will diffuse through these films rapidly. PEG-modified ferrocenes in PEG melts are likely gaussian and ideal and thus move through the melt by reptation (de Gennes, 1979). As for the covalently crosslinked gels reported herein, diffusion of the mediator and chain reptation are not possible, thus charge may propagate through the collisions of polymer chain segments containing ferrocene redox couples. The drift velocity of a chain segment increases as the degree of polymerization decreases, i.e. as the number of monomers in a chain segment increases (de Gennes, 1979). Thus charge transfer rates through the film will increase as crosslinking density decreases or as the chain length of the PEG-DA macromer increases. Both considerations will result in greater chain mobility within the hydrated gel.

Figure 7:
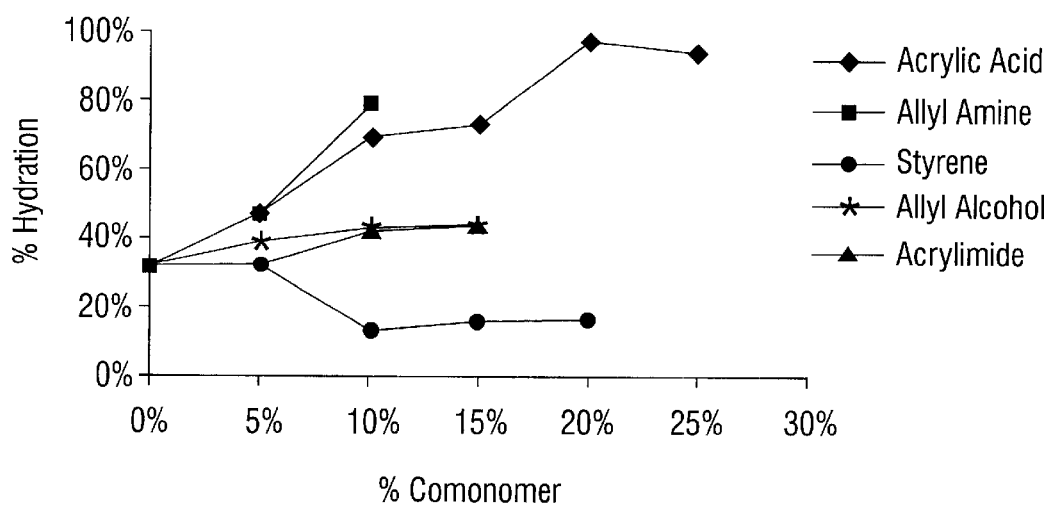
FIG. 7. Percent Hydration of PEG Copolymer Hydrogel. Acrylic acid (-♦-), allyl amine (-■-), styrene (-●-), allyl alcohol (-x-), and acrylamide (▲).

Enzyme Electrode Performance. To determine the electrode response to glucose, aliquots of 2M glucose were added to a rapidly stirred and degassed solution (ie. anaerobic conditions, 25° C.) of 0.1 M PBS while maintaining the electrode at a constant potential ($E_{app}$=300 mV vs. Ag/AgCl), with glucose concentration increasing from 0 to 20 mM in 2 mM increments. The electrode was 75% PEG-DA, 24% vinylferrocene, 1% glucose oxidase (GOX), on 1.6 mm diameter Au disk electrode. The electrode current increased as glucose concentration was increased from 0 mM to 20 mM, demonstrating that the enzyme has retained its activity within the gel. At 4 mM glucose the current density was approximately 2.5 μA/cm², which compares favorably with ferrocene-based glucose electrodes made by conventional means (Tatsuma et al., 1994; Hale et al., 1990). The response to glucose was linear with an $R^2$ value greater than 0.98. Glucose electrodes made in this manner showed only minor loss in GOX activity and were highly responsive to glucose. Similar procedures were used to prepare gels of different compositions. Through the incorporation of monomers such as acrylic acid, allyl amide, allyl alcohol, and styrene into the gel, the degree of water penetration into the gel was controlled (FIG. 7), and thus the permeability of water-soluble analytes into the interior of the hydrogel.

The current response in the absence of oxygen indicated electron transfer between glucose oxidase and ferrocene molecules bound to the gel, in addition to charge propagation through the gel to the electrode surface. Response times to step changes in glucose concentration were also determined to step changes in glucose concentration while operating the electrode at constant potential (300 mV vs. Ag/AgCl). The time to reach 95% of maximum current for a change from 4 to 6 mM glucose was approximately five minutes. This relatively slow time was likely due to mass transfer limitations presented by the polymer film itself, a result of the low molecular weight of the PEG-DA macromer and the high degree of crosslinking in the gel.

Figure 8:
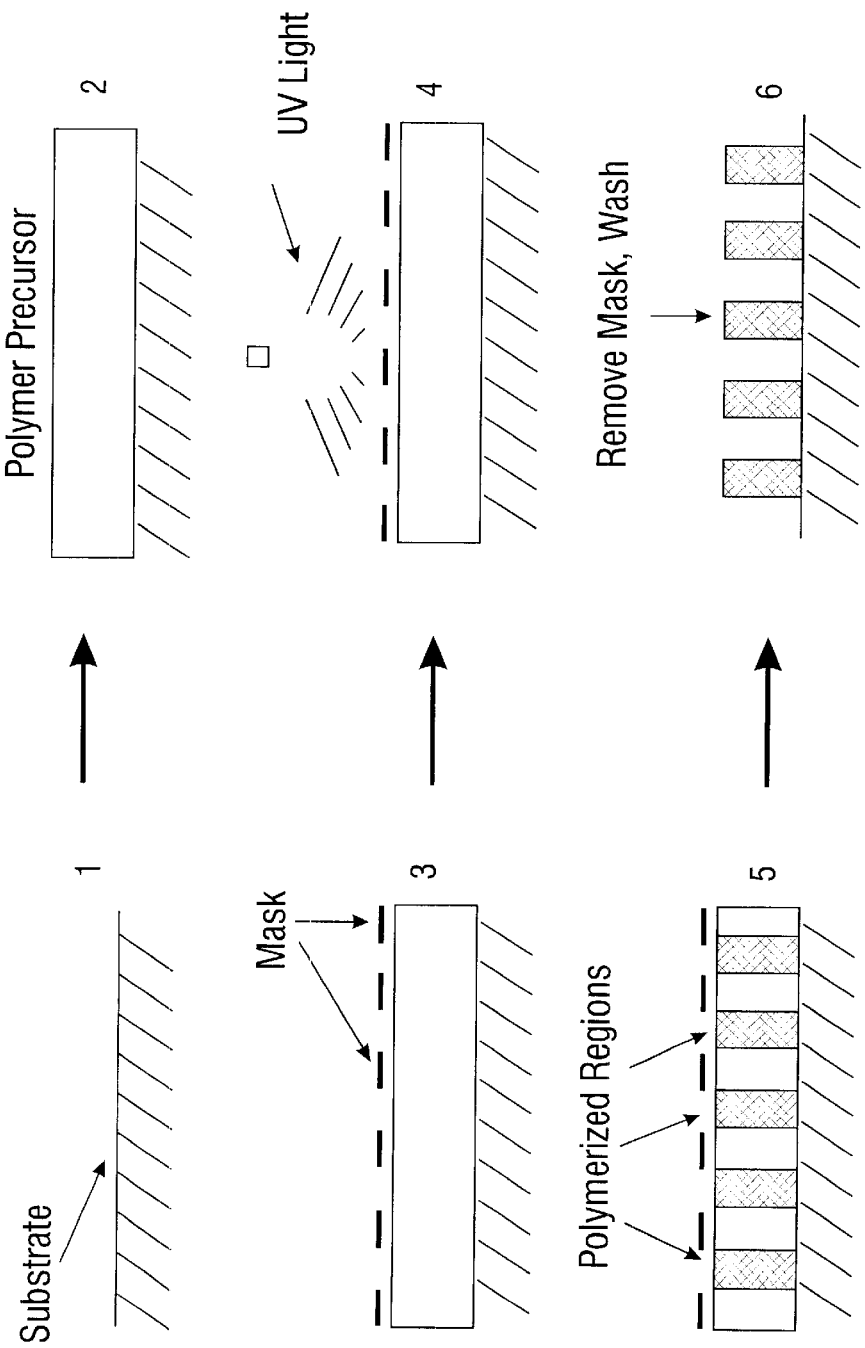
FIG. 8. Schematic of the fabrication of patterned redox polymer hydrogels. A thin film (approximately 100 µm) of the redox hydrogel precursor solution was coated onto a clean planar substrate. An aluminum shadow mask was then placed over the film at a distance of 5 mm and exposed to 365 nm UV light, 20 W/cm². The UV source was approximately 2 cm above the mask. The areas of the film exposed to UV light polymerized. The mask was then removed and the pattern developed by washing the substrate with copious amounts of water.

Hydrogel Patterning. With the eventual goal of forming recognition molecule-containing hydrogel arrays, the inventors investigated the patterning of PEG-DA/GOX/vinylferrocene films using UV photolithography, the most common patterning technique used for semiconductor microfabrication. Solutions of 75% PEG-DA, 5% DMPA, and 20% vinylferrocene by weight, were placed in a thin layer, approximately 100 μm, over a glass substrate. An aluminum shadow mask was held approximately 5 mm above the coated substrate. The 20 W/cm² UV light source was held approximately 2 cm above the shadow mask, and the mask was illuminated for 10 sec. The mask was then removed, and the surface washed with copious amounts of distilled water, removing the unpolymerized regions. This overall process is illustrated in FIG. 8. A SEM micrograph of a representative three by three polymer array was made where each individual array element was approximately one mm in diameter.

Irregularities can readily be observed in many of the members of these polymer arrays. There are several sources for these defects. First, the substrate was shadow masked rather than masked using a quartz mask. Light passes through the shadow mask in air until it reaches the polymer surface where reflections and diffraction of light can occur and result in distortions in the individual array members. A quartz mask, which consists of a patterned metal film on a quartz substrate that is placed directly on the surface of the polymer film, minimizes reflections and diffractions by decreasing the difference in index of refraction changes as light reaches the film. Thus some size, shape and thickness irregularities may be eliminated by using a quartz mask as is commonly done in semiconductor processing. Small irregularities towards the centers of the individual hydrogel elements are also apparent and most likely are caused by the trapping of air during polymerization. Degassing the polymer precursor prior to polymerization may easily eliminate this problem. Other electron micrographs indicate slight "wrinkles" in the gel, which can be attributed to the strong mechanical stresses that take place due to polymerization. These mechanical stresses are often seen in photopolymer films and may be attributed to the uneven mass transfer of monomer between polymerized and unpolymerized regions, resulting in local swelling and distortions in the film (Krongauz, 1995). By increasing the PEG-DA chain length, it is contemplated that the resulting films will possess more conformational freedom, resulting in less strain on entrapped biomolecules, further minimizing any loss in activity. This increase in conformational flexibility may also serve to decrease some of the mechanical contractions.

Thus, ezyme-containing redox polymer hydrogels can be rapidly fabricated using UV-initiated free radical photopolymerization. Using glucose oxidase as a model recognition molecule, amperometric biosensors for glucose were produced by entrapping glucose oxidase in a hydrogel formed from vinylferrocene and poly(ethylene glycol) diacrylate. Glucose oxidase retained its activity under the high intensity UV exposure conditions used to form the films and was able to transfer electrons to ferrocenes bound to the gel structure. Glucose enzyme electrodes with an extended linear range were produced. These gels were patterned, and may be used in biosensor arrays.

EXAMPLE 3

Bench-Top Fluorescent Probe for use in Noninvasive Glucose Monitoring

Figures 9A, 9B:
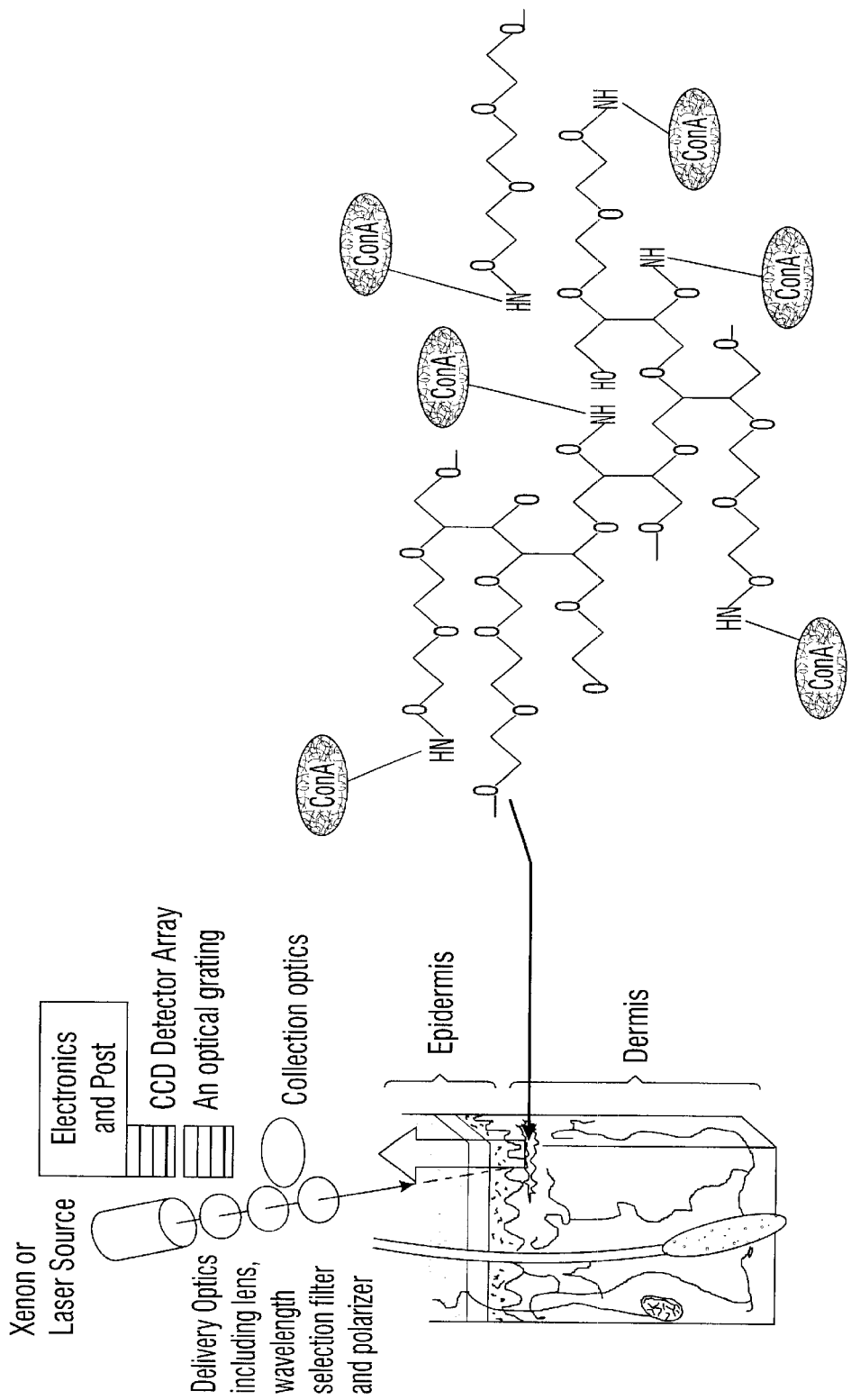
FIG. 9A and FIG. 9B. Exemplary bench-top fluorescent system and hydrogel particles.

In this example, a bench-top fluorescent unit, as depicted in FIG. 9A, was built and tested. The bench-top system is designed to produce a measurable change in fluorescence intensity of the chemically sensitive polymer particles (FIG. 9B) as a function of interaction with glucose. In this embodiment, the excitation is at 488 nm and emission is at 520 nm, which is optimal because it is between the 420 nm and 540 nm bands of hemoglobin, and also away from the 460 nm band of bilirubin. The key factors in the design include the determination of the optimal geometry to yield the highest signal-to-noise ratio (SNR), the compensation for the effects due to tissue optics, and the ability to obtain a quick scan to provide for ease of patient use and avoidance of motion artifacts.

In other embodiments, backscatter based optical approaches, including fluorescence, in vivo using fiber optic delivery and collection, are contemplated for use, particularly for remote body locations such as the cervix, stomach, and prostate. However, as this example concerns a dermal surface based approach, bulk optics are used for delivery and collection of the light. This allows for optimal throughput of the incoherent source, and thus increases SNR. The input light from a xenon source is collimated and wavelength filtered (488 nm) to produce a quasi-monochromatic beam at the appropriate excitation wavelength for FITC-dextran. The reflected light is initially focused onto the slit of a monochrometer and collected by a CCD array. This allows for the real-time collection of the signal simultaneously at all wavelengths within the band of interest. Having multiple wavelengths provides for post-processing using a partial least squares or other algorithm, if required, in order to correlate the intensity change to glucose or analyte concentration.

In other designs contemplated for use in certain aspects of the invention, the number of wavelengths required is not based as much on the overall SNR of the return signal in the presence of auto-fluorescent tissue. When FITC-dextran is displaced from TRITC-Con A by the glucose, the fluorescent intensity increases because of quenching in the bound state but a change in the emission or excitation spectrum does not occur. Therefore, two to three wavelengths located at the peak and at the baseline identified with the CCD based system can be used. With a reduction in the number of wavelengths, a system incorporating optical filters and more sensitive single element detector such as a photo-multiplier tube can be used.

As mentioned herein, fluorescence intensity, per se, can be hard to quantify because it varies with tissue optics. However, the basic mechanism by which quenching occurs is through a decrease in the fluorescence lifetime, and lifetime measurements are independent of tissue optics. Thus, an instrument for measuring fluorescence lifetime can also be used. Additionally, fluorescence depolarization, which provides similar information to that of the fluorescent lifetime measurements, can be used. The polarization of fluorescence relative to the excitation source polarization is a function of both fluorescence lifetime and motion of the fluorophore. If the fluorophore does not move during its lifetime, the fluorescence is highly polarized because the down-transition is spatially oriented with the up-transition. If the probe fluorophore is quenched when bound to TRITC-Con A, the lifetime is lower and motion is restricted, both of which inhibit fluorescence depolarization. In order to overcome potential problems due to the birefringence of the tissue, particularly in the presence of motion artifact, using a single detector the ratio of the fluorescence at two polarization angles (initially aligned and crossed linear polarizers) is measured, in order to identify whether a better correlation to the TRITC-Con A binding exists relative to fluorescence intensity alone, particularly in the presence of other auto-fluorescent tissue.

Instruments are built as specified above with and without the polarizers in place. The instrument is tested on progressively complex media. The first series of studies are done on a 100 micrometer methacrylate cuvette filled with FITC-dextran and TRITC-ConA (15:1 ratio of TRITC:FITC) in PBS solution and doped with varying physiologic glucose concentrations from 0–600 mg/dl. Pig skin was wrapped around the test cell and a similar glucose and fluorophore study performed. The optical properties of pig skin mimics that of human skin, but the full pig skin is not wrapped around the test cell, because pig dermis is about 3 mm thick and also has a muscular fascia at the bottom. A dermatome is therefore used to cut off a 0.15 mm thickness layer that includes the epidermis. That depth is easily accessible to wavelengths around 500 nm. An additional in vitro test of the system is to utilize the skin-wrapped test cell filled with the fluorescence-doped polymer beads described below.

EXAMPLE 4

A Fluorescent Glucose Assay Using Poly-L-Lysine and Calcium Alginate Microencapsulated TRITC-Succinyl-Concanavalin A and FITC-Dextran A polymer-based fluorescent sensor using FITC-Dextran and TRITC-Succinyl-Con A encapsulated in calcium alginate gel spheres surface modified with a sodium alginate and poly-L-lysine coating to stabilize the gel was prepared. Additionally, in vitro studies of the polymer spheres in a solution of $dH_2O$ and glucose were conducted, as described below.

Materials. G-25 Medium Sephadex was purchased from Pharmacia Biotech AB. Alginic acid, tetramethylrhodamine, fluorescein isothiocyanate dextran (MW 70,000), poly-L-lysine hydrochloride (MW 30000–70000), and succinyl-concanavalin A were obtained from Sigma. All other chemicals were purchased from Sigma and were of analytical grade.

Conjugation of TRITC-succinyl-Con A. TRITC was conjugated onto succinyl-Con A ("CONJUGATION WITH AMINE-REACTIVE PROBES", 1996). Briefly, 100 μL of 5 mg TRITC dissolved in 0.5 mL of DMSO was added to a solution of 10 mg succinyl-Con A dissolved in 1 mL of 0.1 M sodium bicarbonate. The reaction was incubated for 1 h at room temperature and pH 9.0 with continuous stirring. The conjugate was separated from unreacted TRITC dye using a gel filtration column (10×300 mm) packed with G-25 Medium Sephadex and equilibrated with 0.1 M phosphate buffered saline (PBS). Fractions were collected in 3 mL increments. Relative concentrations of TRITC-Succinyl-Con A in the excluded fractions were determined using a Bio-Rad protein assay calibrated against bovine serum albumin (BSA). The final solutions were lyophilized and stored at 0° C. until used.

Preparation of alginate/poly-L-lysine microencapsulated TRITC-succinyl-Con A and FITC-Dextran. Alginate and poly-L-lysine (PLL) coated microcapsules were prepared similar to the procedures used to microencapsulate transplanted Islets of Langerhans ("CONJUGATION WITH AMINE-REACTIVE PROBES", 1996). 10 μg of FITC-Dextran and 200 μg of TRITC-succinyl-Con A (calculated relative to BSA assay) were dissolved in 1 mL of 1% (w/v) sodium alginate solution. The solution was gently agitated for an hour. Calcium alginate spheres were created by extruding the solution from a 21-gauge syringe into a 10 mM $Ca^{2+}$ solution. After curing in the solution for ten minutes, the spheres were agitated for one hour in a 1 mg/mL poly-L-lysine solution. The PLL-coated spheres were transferred to a 1% (w/v) sodium alginate solution, and agitated for one hour. Excess alginate was strained off, and the final spheres were incubated in a 4 mM $Ca^{2+}$ solution.

The procedure successfully encapsulated the TRITC-succinyl-Con A and FITC-Dextran. The spheres were stable when soaked in physiological levels of $Ca^{2+}$ overnight. The alginate-PLL encapsulation procedure was effective at preventing Con A and Dextran leaching. No dye leaching was visible to the naked eye. The spheres had a 1.5 mm TRITC colored center, surrounded by 1–2 mm of transparent alginate-PLL coating. Only a relatively small amount of TRITC fluorescence was detected when scanning the sphere soaking solution. It is suspected that the minute amount of TRITC detected was unbound dye, which was not separated by the gel filtration column following dye conjugation. No FITC fluorescence peak was detected in the solution. FITC-Dextran was purchased conjugated, so it was expected that there was no unbound dye.

A second possibility is that the molecular weight cut off of the spheres is approximately 70 kD. The permeability of alginate-PLL coated spheres is a function of the molecular weight of the PLL, weight percentage of the alginate solution used for coating, and thickness of the coating (Goosen et al., 1985). It is feasible that the PLL (MW 30,000–70,000) coating is impermeable to compounds such as the FITC-Dextran (MW 70,000) used, while exhibiting slight permeability to compounds like succinyl-Con A (MW 54,000; Edelman et al., 1973). This would explain both the absence of FITC fluorescence, and the presence of TRITC fluorescence.

Solutions that had bathed the spheres for up to 42 h were analyzed. A significant decrease in leached dyes compared to spheres prepared without an alginate-PLL coating was verified via fluorescent scanning of the solutions. When compared to fluorescent spectra of the 10 mM $Ca^{2+}$ solution the initial calcium alginate spheres were made in the TRITC peak decreased by 70%.

Fluorescence measurements of spheres. Fluorescent spectra for the alginate-PLL coated microcapsules were recorded using a fluorescence spectrometer (QM-1, Photon Technology International). The spectrometer system uses an excitation source from a 250 W Xenon arc lamp, which is coupled into the excitation monochromator through a 250 μm slit. A 1200 grooves/mm grating is used to disperse the light and direct radiation centered at 488 nm on the 250 μm exit slit. A beamsplitter allows monitoring of the excitation light intensity with a reference detector. The excitation radiation is directed to the sample, which is contained within a 1-cm pathlength methacrylate cuvette. Fluorescent light is collected at 90° to the excitation beam and coupled into the emission monochromator through a 250 μm slit. Another 1200 grooves/mm grating disperses the light and centers the wavelengths of interest on another 250 μm exit slit. The grating is rotated under control to allow scanning from 514–660 nm. A PMT (R928, Products For Research, Inc.) behind the slit counts the photons incident on its face. A 500 nm long-pass filter (Edmund Scientific) is introduced after the sample chamber to reduce the detection of scattered light from the emission source.

Equal volumes of 0.1 M PBS solutions containing 0, 200, 400, 600, and 800 mg/dL glucose were added to the cuvette containing the spheres and changes in the fluorescence emission at 520 nm from the disassociation of the FITC-Dextran/TRITC-succinyl-Con A bond were recorded. Five emission scans were recorded for each glucose concentration and then averaged.

Figure 10:
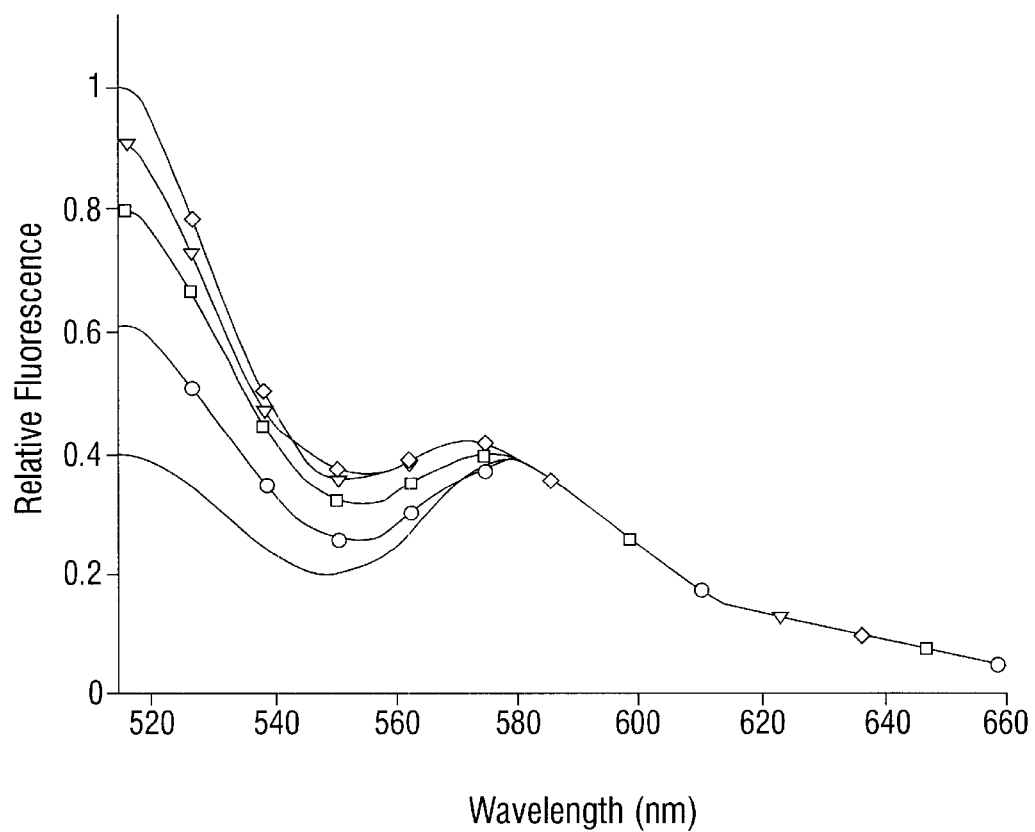
FIG. 10. Fluorescent spectra of calcium-alginate, poly-L-lysine coated spheres with 200 µg/mL TRITC-succinyl-Con A and 10 µg/mL FITC-Dextran in (—): PBS with no glucose. b) Circles (○): PBS with 200 mg/dL glucose. c) Squares (□): PBS with 400 mg/dL glucose. d) Triangles (▽): PBS with 600 mg/dl glucose. e) Asterisks (*): PBS with 800 mg/dL glucose.

FIG. 10 shows the results of the fluorescence study. As expected, when the glucose concentration in the bath solution was increased, FRET quenching of the FITC fluorescence signal decreased, resulting in an increase of the 518 nm emission peak. Spectra were collected for 0 mg/dL glucose (solid line) to 800 mg/dL (asterisks) and viewed with FELIX™. A seven point smoothing routine and a $2^{nd}$ order polynomial fit was performed on the raw data with a Savitsky-Golay function in MATLAB™. After smoothing, the spectra were normalized at the FITC peak (518 nm) using the maximum value of the 800 mg/dL sample. All subsequent spectra can be seen as a percentage of this peak.

A comparison of the FITC emission (518 mn) to the TRITC emission (580 nm) for 0, 200, 400, 600, 800 mg/dL glucose was conducted. A least squares regression was performed and demonstrated the linear nature of the glucose response.

The results presented herein indicate that a fluorescent glucose assay based on TRITC-succinyl-Con A and FITC-Dextran can be transitioned from aqueous based systems to polymer hydrogel microspheres. FITC peak intensity changes when exposed to varying concentrations of glucose was as predicted. The fluorescence change with increasing glucose concentration, ranging from 0 to 800 mg/mL, was linear from 0 to 600 mg/mL, with a reduced response at 800 mg/mL. It is believed that the decrease in slope revealed when the glucose concentration changed from 600 mg/mL to 800 mg/mL is either a result of all of the initially bound FITC-Dextran having already been displaced by glucose, or due to emission self-absorption by FITC-Dextran (Schultz and Sims, 1979). This effect can be modified by adjusting the ratio of FITC-Dextran to TRITC-succinyl-Con A. Additionally, the polymer-based spheres may be produced with micrometer and nanometer dimensions, resulting in improved mass transfer.

Alginate spheres containing physically entrapped TRITC-succinyl-Con A and FITC-dextran were initially fabricated using $Ca^{2+}$ cross-linked alginate; the gel was stabilized with an additional poly-L-lysine outer layer. Microcapsules have been demonstrated to be highly permeable to water and low molecular weight compounds (Tanaka et al., 1984). Fluorescence intensity of FITC emission from these spheres was shown to be glucose responsive, with a linear fluorescent increase as glucose concentrations increased to 600 mg/dL, but the dextran displacement due to competitive glucose binding was not reversible within a reasonable timescale. In addition, the microcapsules experienced leakage of TRITC-succinyl-Con A and FITC-dextran (the extent of which was dependent upon the molecular weight of the poly-L-lysine used), and they lacked structural rigidity once the interior alginate had diffused out of the microcapsule.

EXAMPLE 5

A Flourescence-Based Glucose Biosensor Using Concanavalin A and Dextran Encapsulated in a Poly(Ethylene Glycol) Hydrogel Poly(ethylene glycol) or PEG has numerous properties beneficial for use in vivo and may be an improvement over the alginate/poly-L-lysine system. A highly water soluble hydrogel is formed upon cross-linking this polymer and thus PEG gels may be used to encapsulate high molecular weight biomolecules.

This example describes a simple and structurally stable system based on a poly(ethylene glycol) (PEG) hydrogel incorporating chemically immobilized pendant TRITC-Con A and physically immobilized FITC-dextran. A fluorescence biosensor is described that uses photopolymerized poly (ethylene glycol) (PEG) hydrogel incorporating fluorescein isothiocyanate dextran (FITC-dextran) and tetramethylrhodamine isothiocyanate concanavalin A (TRITC-Con A) chemically conjugated into the hydrogel network using an α-acryloyl, ω-N-hydroxysuccinimidyl ester of PEG-propionic acid. Microspheres whose fluorescence intensity is responsive to glucose were fabricated and optimized for the maximum sensitivity to glucose and further characterized to determine the response time of the fluorescent signal to changes in glucose concentration.

Reagents. Fluorescein isothiocyanate (FITC) dextran (MW 2,000 kDa, labeling ratio 0.009 mole dye/mole sugar), tetramethylrhodamine isothiocyanate (TRITC) concanavalin A (labeling ratio ~1.0 mole dye/mole lectin), D-mannose, glucose, glycine, and divinyl sulfone (DVS) were obtained from Sigma Chemical Co. (St. Louis, Mo.). Poly(ethylene glycol) diacrylate with a molecular weight of 575 (PEG-DA), trimethylolpropane triacrylate (TPT), and 2,2 dimethoxy-2-phenyl-acetophenone (DMPA) were obtained from the Aldrich Chemical Co. (Milwaukee, Wis.). Heavy paraffin oil and n-heptane were purchased from Fisher Scientific, Inc. (Pittsburgh, Pa.). The α-acryloyl, ω-N-hydroxysuccinimidyl ester of poly(ethylene glycol)-propionic acid, MW 3400 (PEG NHS-3,400) was purchased from Shearwater Polymers, Inc. (Huntsville, Ala.). Coomassie Blue G-250 protein assay reagent was purchased from Pierce (Rockford, Ill.). All reagents were used as received. One-tenth molar phosphate buffered saline (PBS) consisted of 11 mM potassium phosphate monobasic, 3 mM sodium phosphate dibasic heptahydrate, and 0.15 M NaCl in 18 MΩ·cm deionized water (E-pure, Barnstead).

Preparation of TRITC-succinyl ConA. TRITC-succinyl ConA is synthesized using an established protocol (Molecular Probes, 1996), and acrylated by reacting n-hydroxysuccimide-PEG-acrylate with the protein for 30 minutes followed by dialysis to remove unreacted PEG and lyophilization. Succinylation of ConA prevents ConA aggregation.

Preparation of FITC-dextran. FITC-dextran is purchased commercially (Sigma, St. Louis, Mo.; Molecular Probes, Inc., Eugene, Oreg.) and acrylated by reaction with acryloyl chloride in benzene, followed by precipitation in diethyl ether.

Preparation of Mannosylated FITC-dextran. Mannosylated FITC-dextran was prepared similar to a procedure published (Ballerstadt and Schultz, 1997). FITC-dextran (35 mg) was dissolved in 2 mL of deionized water, to which 2 mL of 0.1 M bicarbonate buffer (pH 10.5) and 30 μL of DVS was added. The mixture was stirred at room temperature for 1 h. 100 mg of D-mannose was then added and allowed to react for 1 h. The reaction was terminated by addition of 2 mL of 5% (w/v) glycine. Concentration of the final dextran solution was determined from a fluorescent standard curve using known concentrations of FITC-dextran 2,000 kDa.

Preparation of PEG Hydrogel Precursor Solution with TRITC-Con A and FITC-dextran. PEG spheres with a 100:1 mass ratio of TRITC-Con A to FITC-dextran were constructed as follows: TRITC-Con A and FITC-dextran were dissolved immediately prior to use in 0.1M PBS solutions at a concentration of 1 mg/mL. TRITC-Con A was incubated in PBS solution with PEG NHS-3,400. The NHS esters react with lysine residues on the surface of Con A, resulting in an acrylate-modified Con A. Five hundred microliters of TRITC-Con A solution and 5 mg of PEG NHS-3,400 were added to 1 mL of PEG-DA, and then vortexed for 30 min. The PEG-diacrylate (MW 575) and acrylate-modified TRITC-Concanavalin A hydrogel polymerization scheme shown in FIG. 4.

Five microliters of FITC-dextran, 100 μL of TPT, and 10 mg of DMPA were added and vortexed for approximately 30 min. In order to investigate the effect on the sensor with varying mass ratios, polymer precursor solutions were mixed with 200–1000 μg of TRITC-Con A, which generated hydrogels with TRITC-Con A/FITC-dextran mass ratios encapsulated within the hydrogels ranged between 40:1 to 200:1. Additional ratios of the binding pair were examined by replacing FITC-dextran with mannosylated FITC-dextran, or altering the total amount of FITC-dextran added.

Limits on the TRITC-Con A/FITC-dextran ratio were selected by using a fixed concentration of FITC-dextran 2,000 kDa (5 μg/ml PEG) to fabricate and fluorescently evaluate PEG hydrogels containing TRITC-Con A/FITC-dextran. The low end of the ratios considered was selected as that resulting in the smallest TRITC-Con A emission peak which could be visually detected beside the FITC emission peak. The high end of the range was dictated by precursor solution phase separation between the TRITC-Con A /0.1 M PBS solution and TPT. Increasing amounts of the TRITC-Con A aqueous solution resulted in a more turbid PEG precursor solution when TPT was added. This high turbidity resulted in an increase in measured scatter at the FITC peak. In order to reduce signal noise, the 500 nm bandpass filter was added before the sample chamber when fluorescence spectra was used to characterize the initial fluorescence TRITC/FITC ratios and percent change in fluorescence for different TRITC-Con A/FITC-dextran mass ratio hydrogels. High concentrations of TRITC-Con A also resulted in loss of some sugar-binding lectin due to irreversible agglutination.

Preparation of PEG Hydrogel Spheres. From these precursor mixtures, microspheres may be produced by one of two exemplary methods, depending on the size of sphere desired. Large spheres (0.25 mm to 3 mm) may be produced by forcing the precursor solution through a syringe to form drops in a column of light mineral oil. As the drops descend down the column, they are polymerized by illumination with 365 nm UV light at an intensity of 20 W/cm$^2$. The spheres are then collected at the bottom of the column, washed with heptane to remove the mineral oil, and lyophilized. Small spheres (5–200 μm) may be formed by emulsifying the precursor solution in light mineral oil using a homogenizer while under UV illumination. These microspheres are then collected by centrifugation, washed with heptane, and lyophilized.

PEG hydrogels containing TRITC-Con A, FITC-dextran, TPT, and DMPA were cross-linked by UV-generated free radicals. Each PEG precursor solution was extruded through a 21 gauge syringe into a bath of heavy mineral oil illuminated with 20 W/cm$^2$ at 365 nm by an ultraviolet spot lamp (EFOS Ultracure 100SS Plus). When illuminated at 365 nm, CH$_3$ radicals generated by DMPA initiate free radical polymerization of a copolymer network of PEG-DA, TPT, and acrylated Con A by attacking the carbon-carbon double bonds present in the acrylated groups of the biomolecule and the PEG end groups. A schematic of the polymerization mechanism is shown in FIG. 4. FITC-dextran is physically immobilized inside the cross-linked network. The experimental setup was configured to minimize biomolecule exposure time to the UV radiation, less than ten sec, more than sufficient for gelation of the network. Final acrylate conversion in a similar gel system, estimated by ATR/FTIR, was approximately 43% (Mellott and Pishko, 1999). The spheres were separated, rinsed in 30 mL of n-heptane, rinsed with 30 mL of 0.1 M PBS, and then hydrated overnight in 100 mL of 0.1M PBS. A scanning electron micrograph of the surface of a PEG-DA polymer microsphere was made.

The translation of glucose binding to ConA into a measurable change in fluorescence intensity is directly related to the affinity to ConA of glucose versus that of FITC-dextran within the polymer microenvironment. While this affinity is well understood for ConA in an aqueous environment, there are a number of factors that may change ConA affinity within a polymer environment. If partial or significant ConA inactivation occurs as a result of covalent immobilization, photopolymerization or other processing steps, the processing steps can be modified. For example, the wavelength of photopolymerization can be shifted to the visible region (420 nm) and methyl a-mannose added to protect carbohydrate binding sites.

FITC-dextran is physically immobilized inside the cross-linked network. The setup was configured to minimize biomolecule exposure time to the UV radiation, less than ten sec, more than sufficient for gelation of the network. Final acrylate conversion in a similar gel system, estimated by ATR/FTIR, was approximately 43%. The spheres were separated, rinsed in 30 mL of n-heptane, rinsed with 30 mL of 0.1 M PBS, and then hydrated overnight in 100 mL of 0.1M PBS.

Newly created hydrogels were stable against fracture and leaching when incubated in 0.1M PBS overnight. Attempts to make spheres from a more concentrated solution of TRITC-Con A/PBS (greater than 1 mg/mL) resulted in fracture of the hydrogel due to excessive swelling in PBS. The hydrogels had an equilibrium water content of 24.8%. Sphere volumes changed by 41.8%. The hydrated spheres, having a large water content and decreased PEG density, are highly permeable to small substrates.

Biomolecule encapsulation in PEG resulted in successful retention of both TRITC-Con A and the FITC-dextran, as indicated by observation with a fluorescence microscope, Bradford total protein microassay, and fluorescence evaluation of the glucose solutions used to hydrate the spheres. Unlike previous work with alginate, the PEG hydrogels were polymerized with TRITC-Con A chemically bound into the polymer network. This is an improvement over the use of alginate microcapsules, in which TRITC-succinyl-Con A was entrapped physically in the gel, and slow loss of TRITC-succinyl-Con A and FITC-dextran due to diffusion was experienced.

The spheres were approximately 2 mm in diameter, and visibly homogeneous. Magnification under a fluorescent microscope (Zeiss Axiovert-135) revealed small regions of polymer and dye heterogeneity. PEG hydrogel spheres created with TPT crosslinker resulted in a more turbid precursor solution and cross-linked hydrogel due to increased phase separation in hydrogels containing TPT. Examination of the PEG hydrogels on a fluorescence microscope with FITC and TRITC filters showed an extremely sharp separation between the fluorescence spheres and the bath solution. Fluorescence measurements of the 0.1 M PBS bath revealed weak fluorescent peaks at both 520 and 580. The fluorescent peaks were two orders of magnitude lower in photon counts than the hydrogel sphere fluorescence. A Bradford total protein microassay (Bradford, 1976) sensitive to one microgram per milliliter did not detect any concanavalin A in the bath. These results indicate that FITC-dextran and TRITC-Con A were successfully immobilized in the spheres, with only unbound or weakly-bound fluorophores, and smaller molecular weight components of the FITC-dextran and TRITC-Con A (possibly individual protomers) leaching from the hydrogel.

Fluorescence Measurements of Hydrogels. Fluorescent spectra of the PEG hydrogels were recorded using a fluorescence spectrometer (QM-1, Photon Technology International). The spectrometer system used an excitation source from a 250 W Xenon arc lamp, which was coupled into the excitation monochromator through a 250 μm slit. A 1200 grooves/mm grating was used to disperse the light and direct radiation centered at 488 nm on the 250 μm exit slit. A beamsplitter allowed monitoring of the excitation light intensity with a reference detector. The excitation radiation was directed to the sample, which was contained within a 1-cm pathlength methacrylate cuvette. Fluorescent light was collected at 90° to the excitation beam and coupled into the emission monochromator through a 250 μm slit. Another 1200 grooves/mm grating dispersed the light and centered the wavelengths of interest on another 250 μm exit slit. The grating was rotated by software to scan from 500–600 nm. A photomultiplier tube (R928, Products For Research, Inc.) behind the slit was used to count the photons incident on its face. A 500 nm long-pass filtered (Edmund Scientific) was introduced after the sample chamber to reduce the detection of excitation light scattered by the sample. When comparing hydrogels with different TRITC-Con A/FITC-dextran ratios, a 500 nm band-pass filter was placed before the sample chamber, to decrease scattered excitation radiation about the FITC fluorescence peak.

Evaluation of the hydrogels over a range of TRITC-Con A/FITC-dextran ratios was conducted by collecting spectra and calculating the change in hydrogel fluorescence in 0, 200, 400, 600 and 800 mg/dL glucose solutions. In the absence of glucose, Con A and dextran bind together. The fluorescence due to FITC is greatly reduced because the energy that is typically emitted as photons, is readily absorbed by TRITC. When glucose is added to a solution containing FITC-dextran and TRITC-Con A, competitive binding for the polysaccharide binding sites on Con A occurs between glucose and dextran. For a given glucose concentration, approximately 60 spheres in 40 mL of glucose solution were slowly stirred on a shaker plate for 20 min, transferred to a cuvette filled with 1.5 mL of glucose solution, and excited at 488 nm. During data collection, the emission monochromator was scanned from 500 nm to 660 nm in 2 nm increments with a one sec integration time. Three averages were taken for each data set. A seven point smoothing routine was performed on the raw data with a Savitsky-Golay function using a $2^{nd}$ order polynomial fit. The data was normalized at the TRITC-Con A peak to elucidate the change in the FITC emission resulting from the decreased FRET with glucose addition. Five emission scans were recorded for each glucose concentration and then averaged. Calculation of the percent change in relative fluorescence (RF) at 514 nm was used to compare different TRITC-Con A/FITC-dextran ratios, using the following relation:

$$\% \text{ Change} = (RF_{800\ mg/dL\ glucose} - RF_{0\ mg/dL\ glucose})/(RF_{0\ mg/dL\ glucose}) \quad (10)$$

The glucose displaced FITC-dextran results in an increase in the observed FITC fluorescence peak at 520 nm. Similar behavior was expected in the PEG hydrogel, provided the lectin was not denatured during incorporation and sufficient flexibility remained for the macromolecules to associate and dissociate with glucose.

The initial normalized TRITC-Con A/FITC-dextran fluorescent intensity for PEG hydrogels with mass ratios between 40:1 and 200:1. Prior to normalization, fluorescent intensity was ~50,000 photons/sec. The FITC-dextran (5 μg/mL) peak was centered at 514 nm and TRITC-Con A at 572 nm. When excited at 488 nm, FRET between FITC and TRITC in close proximity due to dextran/Con A binding results in TRITC fluorescence. The lower FITC-dextran/TRITC-Con A ratios (between 40:1 and 100:1) showed a linear decrease in the initial relative intensity with increasing FITC-dextran/TRITC-Con A ratio, due to the increasing TRITC-Con A fluorescence intensity. The decrease in intensity ceased at a TRITC-Con A/FITC-dextran ratio of 100. At this ratio all FITC-dextran fluorescence was quenched by TRITC-Con A, and an increase in TRITC-Con A had little effect. The slight upward trend seen as the ratio is increased from 120:1 to 200:1 was likely due to weak TRITC absorption at 488 nm. This result was similar to that reported (Ballerstadt and Schultz, 1997) for an aqueous glucose assay with high viscosity alginic acid dissolved into the solution.

Figure 13:
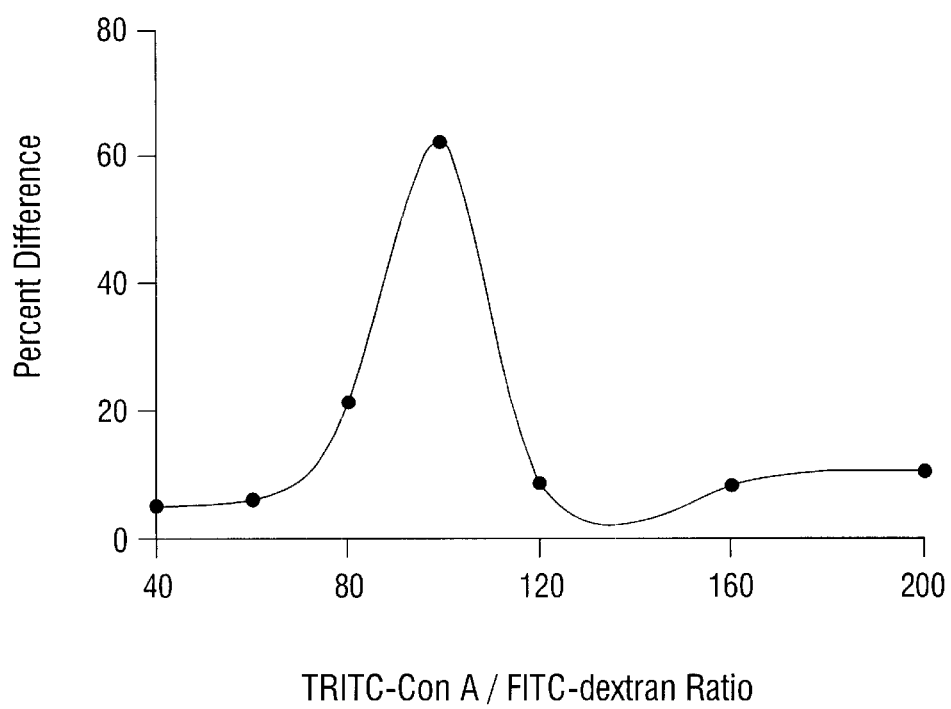
FIG. 13. Relative fluorescent intensity percent difference for an 800 mg/dL glucose increase for PEG hydrogels incorporating TRITC-Con A and FITC-dextran with mass ratios between 40:1 and 200:1.

FIG. 13 describes the fluorescent responsiveness of the PEG hydrogels when exposed to solutions containing glucose. FRET quenching of the FITC fluorescence decreased with increasing glucose, resulting in an increase of the 514 nm emission peak.

It was expected that PEG modification of Con A by a N-hydroxysuccinimidyl (NHS) ester of PEG and subsequent encapsulation into a PEG hydrogel would have no detrimental effect (e.g., denaturing, loss of sugar-binding capability) on TRITC-Con A. Similarly immobilized glucose oxidase in PEG hydrogels using a UV-initiated free radical polymerization scheme demonstrated only limited loss of biomolecule activity when exposure time to the UV light. There was also a possibility that PEG, being a chelating agent, could demetallicize the lectin by calcium chelation, resulting in a loss of sugar affinity. However, the fluorescent results indicate that Con A attached to PEG and incorporation into a UV initiated, free radical polymerized PEG hydrogel did not significantly reduce the lectin's sugar binding capacity due to either UV exposure, calcium chelation, or chemical modification.

Percent fluorescence change was calculated according to equation 1, based upon the initial relative fluorescent intensity of each TRITC-Con A/FITC-dextran ratio hydrogel, and the relative fluorescence intensity of the hydrogels in an 800 mg/dL glucose solution. Fluorescence change was observed to be greatest between TRITC-Con A/FITC-dextran ratios of 40:1 to 20:1. Above and below this range the fluorescence change with glucose was less than 10%, while the average within the range was above 20%, with a peak value of 63%. Higher ratios, which have a large amount of TRITC-Con A relative to FITC-dextran, experience only marginal FITC-dextran displacement from glucose addition due to the abundance of TRITC-Con A binding sites. Lower ratios are biased by having a larger background fluorescence of unquenched FITC-dextran. For example, the initial relative intensity of a PEG hydrogel with a 40:1 lectin/sugar mass ratio is 2.1, while for a PEG hydrogel with a mass ratio of 100:1 it is only 0.812.

Figure 14:
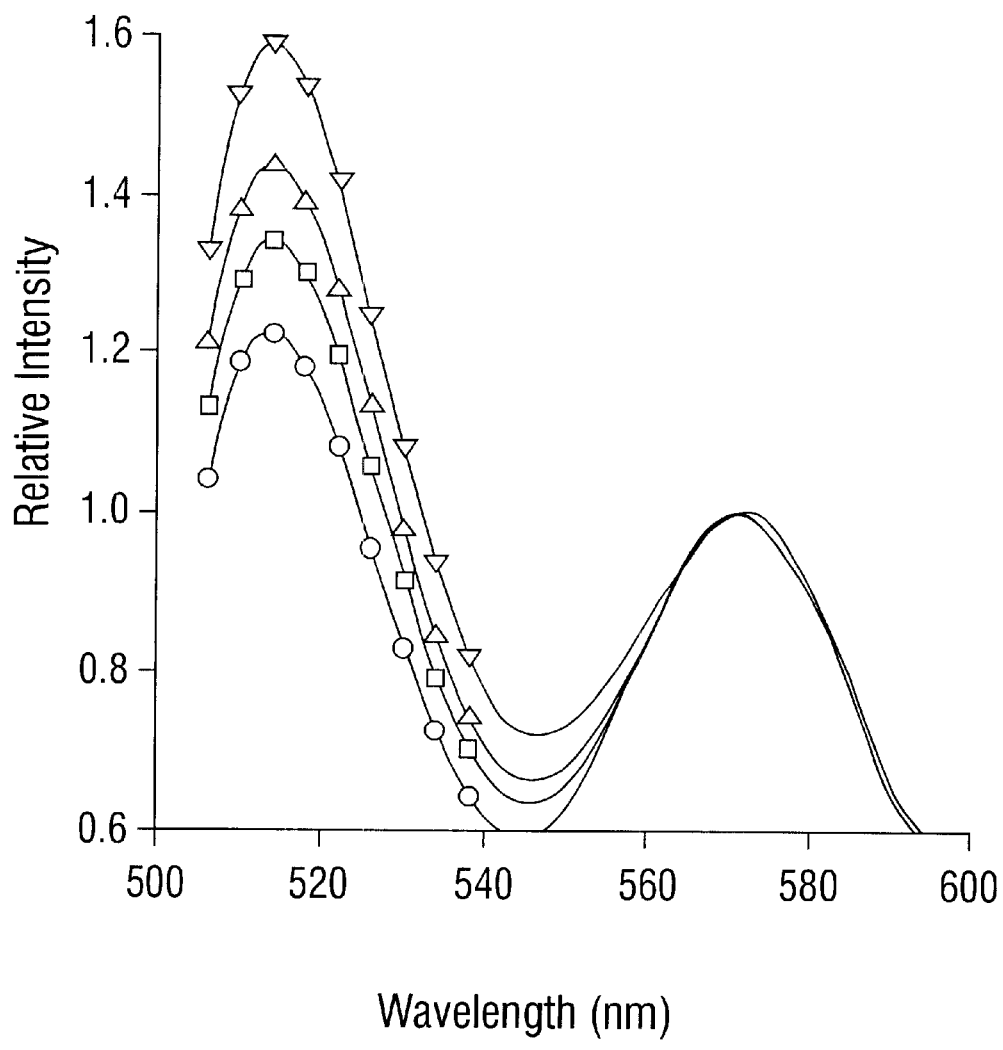
FIG. 14. Competitive binding effect of glucose with FITC-dextran in PEG hydrogels (MW 575) containing 500 µg TRITC-ConA/5 µ FITC-dextran 2,000 kDa for increasing glucose concentrations (•0, ■200 , ▲400, ▼1000 mg/dL of glucose).
Figure 17A:
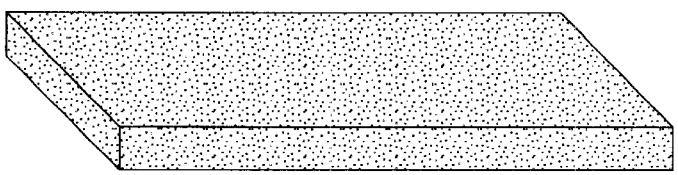
FIGS. 17A–E. Different hydrogel bodies.
Figure 17B:
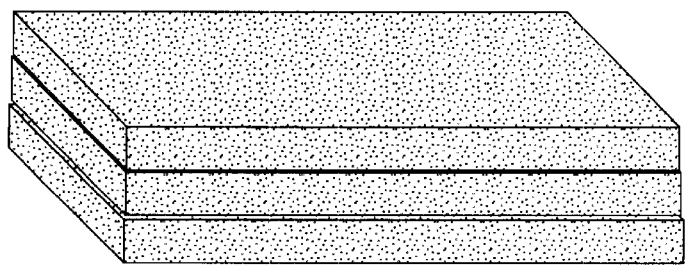
Figure 17C:
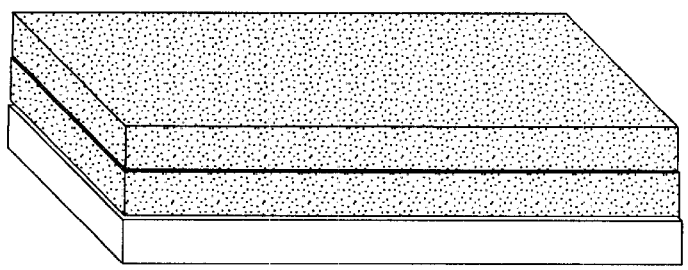
Figure 17D:
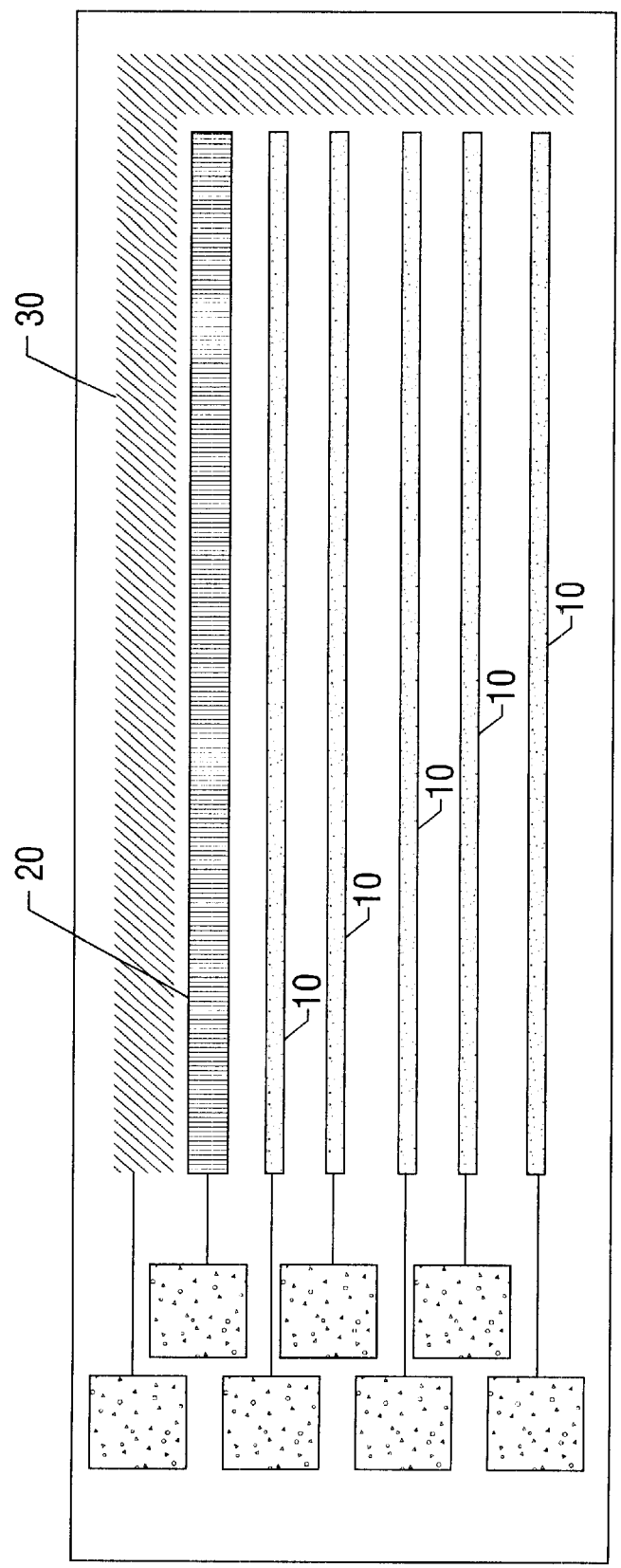
Figure 17E:
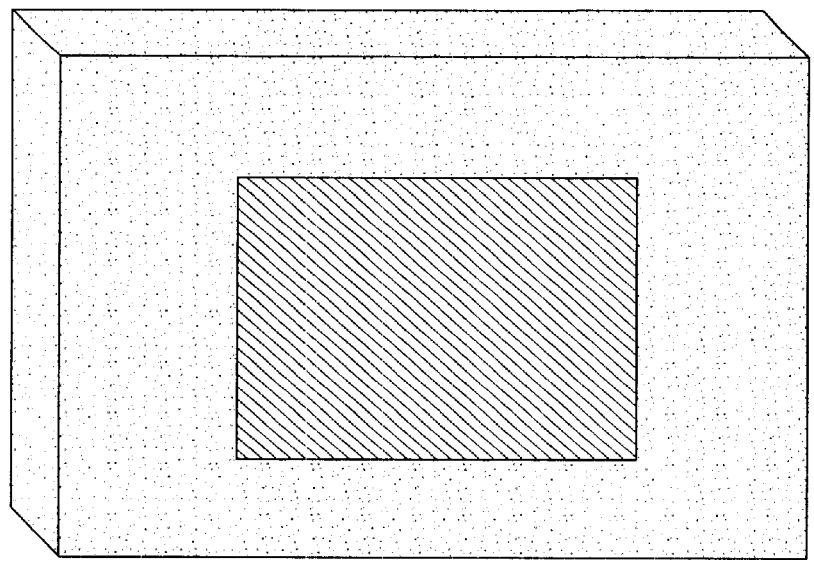

A lectin/sugar ratio of 100:1 was selected for further evaluation, as it appeared to be the TRITC-Con A/FITC-dextran optimum point and had the highest sensitivity to glucose. Scatter about the FITC-dextran peak was not a large source of noise, so the 500 nm bandpass filter was not used as in FIG. 13. Without the filter, more photons illuminate the sample, resulting in greater FITC fluorescence and an increased FITC-dextran/TRITC-Con A relative fluorescent intensity ratio as compared with similar ligand ratio hydrogels shown in FIG. 13. FIG. 14 shows results of fluorescence evaluation of PEG spheres with a TRITC-Con A/FITC-dextran ratio of 100 and a base concentration of 5 μg/mL FITC-dextran 2,000 kDa. FITC fluorescence at 514 nm increased as glucose concentration increased, indicating that competitive displacement of dextran from Con A by glucose within the hydrogel did occur.

The optimum fluorescent change between 0–800 mg/dL was obtained with a TRITC-Con A/FITC-dextran mass ratio of 500:5 μg/ml of PEG. Fluorescent response was linear up to 600 mg/dL. At higher concentrations the response saturated due to the majority of the FITC-dextran having been displaced and concentration quenching by free FITC-dextran. Dynamic fluorescent change upon glucose addition was approximately 10 min for a glucose concentration step change from 0 to 200 mg/dL.

Once the TRITC-Con A/FITC-dextran ratio was optimized for maximum fluorescence change, two sets of hydrogel spheres were created with the optimum ratio, but with a different concentration of macromolecules and an altered dextran ligand. To examine the effect of the polysaccharide binding affinity, spheres were created using 5.0 μg/ml of mannosylated-FITC-dextran at a 100:1 lectin/sugar mass ratio. To examine the influence of overall concentrations of the binding pair within the gel, spheres were created with a reduced concentration of FITC-dextran (2.5 μg/mL), for a 100:1 lectin/sugar mass ratio. These spheres were then evaluated as described earlier.

Post Fluorescence Experimental Evaluation of Glucose Solutions. FITC fluorescence is pH-sensitive, and the dye has been used in the past for pH determination (Haugland, 1996). pH measurements of the test solutions were conducted using a commercial meter (Cole Parmer, Chicago, Ill.) to ensure the observed spectra changes were not due to a pH variation. pH measurements were randomly made on the glucose solutions. No significant change in the solution pH (7.2) was detected.

A Bradford total protein assay was also conducted on several of the glucose solutions using a UV-visible spectrometer (Model 420, Spectral Instruments) to detect leaching TRIT-Con A (Bradford, 1976). Test solutions were fluorescently examined to detect the presence of TRITC-Con A or FITC-dextran leaching from the hydrogel.

It is contemplated that additional experiments may be conducted to determine the stability of microsphere sensitivity to glucose in vitro by incubating microspheres at 37° C. in pH 7.4 phosphate buffered saline containing protein. Over the course of many days (up to 60), the surrounding solution may be assayed to determine if free TRITC or free FITC is released. The concentration of ConA released may then be determined by ELISA as well as Bradford assays.

A comparison of the steady-state fluorescence response for a group of PEG spheres for the FITC-dextran emission (spectra normalized at 572 nm) with that of the TRITC emission for varying glucose concentrations (0 to 1000 mg/dL) was made. A least squares regression was performed on this data to demonstrate the linear nature of the glucose response. Similar to published results for aqueous solutions, (Ballerstadt and Schultz, 1997) the spheres exhibit a linear region for low glucose concentrations, followed by a reduction in the glucose sensitivity with higher glucose concentrations. A least squares fit for the normalized change in fluorescence of PEG hydrogels spheres (MW 575) with a 100:1 TRITC-Con A/FITC-dextran mass ratio had a slope of $5.34 \times 10^{-4}$ relative fluorescence intensity to glucose concentration over a glucose range of 0–600 mg/dL. The decreasing glucose sensitivity above 600 mg/dL is due to the TRITC-Con A/FITC-dextran system becoming saturated with glucose. This results in the majority of the FITC-dextran being displaced by glucose, and self absorption by free FITC-dextran.

The relative fluorescence change due to increasing glucose concentration (0 to 2000 mg/dL) for PEG hydrogels with a 100:1 TRITC-Con A/FITC-dextran mass ratio constructed with 5 μg/mL mannosylated-FITC-dextran (MFITC) in place of FITC-dextran was conducted. Increasing the Con A sugar affinity by altering the amount of mannose conjugated onto FITC-dextran would result in a longer linear glucose concentration range and faster sensor response time due to a stronger affinity for Con A than glucose (Damme et al., 1998). Similar results had been reported in an aqueous solution of Con A and mannose-modified dextran (Ballerstadt and Schultz, 1997). Hydrogel spheres containing mannosylated FITC-dextran had a slightly lower initial TRITC-Con A/FITC-dextran ratio as compared to the 100:1 ratio spheres constructed with unmodified FITC-dextran (0.76 versus 0.81), due to the increased binding affinity enhancing the TRITC fluorescence through FRET. The linear glucose concentration range was nearly twice that of the PEG hydrogels with unmodified FITC-dextran, extending beyond 1000 mg/dL.

It was expected that not only the ratio of Con A to dextran would affect sensitivity, but also that the absolute concentration of the binding pair within the gel would also have a significant influence. PEG hydrogels with a 100:1 TRITC-ConA/FITC-dextran mass ratio constructed with a base concentration of 2.5 μg/mL FITC-dextran had an initial relative intensity of 0.63. The initial relative intensity for these spheres was lower than the MFITC-containing hydrogels and the 500:5 μg TRITC-Con A/FITC-dextran hydrogels, due to the decrease in the total amount of unbound, unquenched FITC-dextran. While there was no noticeable difference from the 5.0 μg/mL FITC-dextran-based spheres in the linear range of the assay, the percent increase in fluorescence was greatly reduced, from 63% to 16%, a result of the decrease in fluorescent FITC-dextran concentration.

Fluorescence Response Time to Increases in Glucose Concentration. The dynamic response of different ratio hydrogels to changes in glucose concentration was very similar. The dynamic fluorescence response of a PEG hydrogel with a 100:1 lectin/sugar mass ratio (normalized at 572 nm) for a change in glucose concentration from 0 to 200 mg/dL was conducted from 0 to 800 sec. The response time for a step change in glucose concentration from 0 to 200 mg/dL was typically 10–12 min. Response times of approximately 10 min in aqueous media, due to mass transfer limitations of glucose across a dialysis membrane have been reported (Meadows and Schultz, 1998).

In contrast, hydrogels constructed with mannose-modified FITC-dextran exhibited a significantly longer response time. Typical response time of the spheres to a change in glucose concentration was four times that of spheres constructed from unmodified FITC-dextran. Each glucose step of 200 mg/dL required approximately 40 min before the fluorescence intensity remained constant. This increase is likely due to the increased affinity of the MFITC-dextran for TRITC-Con A, resulting in slower displacement by glucose.

A key concern when immobilizing Con A and dextran inside of hydrogels has been how reduced biomolecule mobility might impact biosensor performance. The polymer network needs to provide dextran and Con A with the flexibility to rapidly associate and dissociate, while allowing glucose to diffuse into and out of the hydrogel. The PEG hydrogels are highly swollen with solution, resulting in excellent glucose transport. However, the polymer hydrogels confine the mobility of Con A and dextran, resulting in decreased macromolecule diffusion and flexibility within the polymer network. Increase of fluorescence with glucose concentrations indicates that the polymer network was not tight enough to prevent association. However, biosensor response times less than 10–12 min are desirable. It is contemplated that using PEG precursors with larger molecular weight PEG chains could provide more molecular flexibility, thereby increasing analyte diffusion and assay response time.

Reversible, or downward, response for the spheres exposed to a 0 mg/dL solution after soaking in an 800 (or greater) mg/dL solution revealed that the fluorescence response was reversible. After twenty min of stirring in solution, spheres initially soaked in 800 mg/dL had reached a fluorescence intensity level equivalent to 1.5–3 mg/dL of glucose. Overnight, the sphere fluorescence decreased to fluorescence levels of 0–0.5 mg/dL.

The solutions used to bathe the spheres while collecting reversibility data were evaluated to determine whether the decrease was the result of leaching dextran and Con A. Fluorescent and total protein microassay results for both the twenty min and overnight baths were unable to detect any quantifiable level of leached lectin. Glucose concentration cycling on PEG hydrogels with a 100:1 mass ratio (5 $\mu$g/ml FITC-dextran) demonstrated no loss of glucose sensitivity over a 24 h period.

The fluorescent emission response to changing glucose concentrations measured using a polymer encapsulated Con A and dextran system was similar to those measured in aqueous systems. A fluorescent glucose assay based on TRITC-Con A and FITC-dextran can be transitioned from aqueous based systems to PEG hydrogel spheres. When exposed to varying concentrations of glucose, FITC peak intensity changes were observed in the hydrogel that were indicative of glucose-sensitive FRET. PEG spheres have several advantages over the alginate/PLL system: PEG spheres were structurally more rigid, had TRITC-Con A chemically immobilized into the polymer network, and experienced a greater signal to noise ratio. Both materials have excellent water permeability, can be tailored to produce small, syringe-injectable particles, and are biocompatible. These polymer-based spheres may be produced with micrometer dimensions, resulting in both improved mass transfer and the use in transdermal injection for subsequent non-invasive glucose sensing. A 'smart tattoo' of small PEG microspheres, continuously in contact with interstitial fluid at the epidermal-dermal junction, may have better specificity than previously mentioned noninvasive optical approaches, and yet, after implantation, could be noninvasively interrogated by a fluorescent probe to quantify glucose levels.

A microparticle-based fluorescent glucose assay system suitable for subcutaneous implantation, in a fashion similar to a tattoo may be made. The FRET-based glucose biosensor could be optimized in several ways: the concentrations of TRITC-Con A, FITC-dextran, and glucose can be adjusted; the affinity of FITC-dextran for TRITC-Con A can be altered; the dye/conjugate ratio of either macromolecules can be adjusted; and dyes that have either larger Stoke shifts or different characteristic FRET separation distances can be selected.

EXAMPLE 6

Glucose Sensor Based Upon Self-Assembled Monolayers Deposited in Multilayers A glucose sensor that uses a multilayer buildup approach based upon attraction between oppositely charged species, namely an osmium derivative (cationic) and GOX (anionic) was constructed. The size of the individual monolayers, as determined via ellipsometry, along with the number of redox sites within a given monolayer was determined. Modification techniques other than varying the number of layers are described, specifically as enzymatic response of the basic multilayer design is compared to that of multilayers that were chemically or photochemically crosslinked. Finally, an initial demonstration of patterning was performed through the utilization of microcontact printing of mercaptoundecanoic acid (MUA) and blocking agents such as C16-Thiol.

Reagents. Glucose oxidase (GOX, EC 1.1.3.4, Type X-S, 128 units/mg solid from *Aspergillus niger*), was obtained from Sigma Chemical Co. (St. Louis, Mo.). 2,2'-dimethoxy-2-phenyl-acetophenone (DMPA), ammonium hexachloroosmate(IV) and 2,2'-dipyridyl (bpy) were obtained from the Aldrich Chemical Co. (Milwaukee, Wis.). Dextrose, methanol, ethylene glycol and acetonitrile were obtained from Fisher Scientific Co. (Pittsburgh, Pa.). An $\alpha$-Acryloyl, $\omega$-N-hydroxysuccinimidyl ester of Poly (ethylene glycol)-propionic acid (MW 3,400) (PEG-NHS) was purchased from Shearwater Polymers (Huntsville, Ala.). All reagents were used as received.

Polymer Synthesis. All osmium based poly-cationic charge mediators were synthesized according to a three step procedure (Kober et al., 1988). In brief, two equivalents bipyridine (177.8 mg) were mixed with one equivalent ammonium hexachloroosmate(IV) (250 mg) in 50 mL ethylene glycol. This mixture was heated to reflux for 45 min and then precipitated with supersaturated sodium dithionite, followed by washes with water and ether, resulting in 67 mg of $Os(bpy)_2Cl_2$ (Kober et al., 1988).

$Os(bpy)_2(Cl)_2$ precursor was then utilized for the synthesis of two specific osmium based derivatives. The first of these, $Os(bpy)_2(PVP)$-co-allylamine, was synthesized as follows. 1.0 g of 4-vinylpyridine, 1.0 g allylamine, 0.2 g AIBN and 200 $\mu$L HCl were mixed in 50 mL acetonitrile. This solution was refluxed for 2 h, and then the acetonitrile was removed by rotary evaporation. The resulting polymer was dissolved in 1 mL of methanol and precipitated in 50 mL of ethyl ether. Ethyl ether was then decanted, and the (PVP)-co-allylamine was melted and collected as a liquid. 100 mg of $Os(bpy)_2Cl_2$ was then added to 100 mg of the (PVP)-co-allylamine in 50 mL ethylene glycol and refluxed under $N_2$ for 1.5 h. Ethylene glycol was removed, and the product dissolved in a minimal amount of methanol followed by precipitation in 70 mL ether. The ether was then decanted off and $Os(bpy)_2(PVP)$-co-allylamine was dried and collected.

The second osmium derivative, $Os(bpy)_2(PVP)$-acrylate, was prepared as follows. 0.6 g $Os(bpy)_2Cl_2$ was mixed with 0.33 g poly(4-vinylpyridine) (mw 40 k) in 18 mL of ethylene glycol. This was refluxed under $N_2$ for about 3 h. Upon cooling to room temperature, the polymer was collected by dripping the mixture into rapidly stirred ethyl acetate (400 mL). A sticky polymer resulted, and was dissolved in a minimum amount of methanol. This methanol solution was then added dropwise to 800 mL of rapidly stirred ether, then filtered and dried (Ye et al., 1993). 1 g of the resultant polymer was then mixed with 0.5 of bromoacrylate in 50 mL of DMF. This was refluxed under $N_2$ at 60° C. for about 2 h. The resultant solution was cooled to room temperature, poured into rapidly stirred acetone, filtered, washed with acetone and stored in a desiccator (Gregg and Heller, 1990).

Multilayer Fabrication. The process utilized for the generation of the multilayer films is depicted in FIG. 15.

Initially, gold wafers are cleaned under ozone and then were immersed in 0.001 M MUA in ethanol for about 20 min to functionalize their surface. The wafers were removed and dried under $N_2$. The wafer would then be alternately placed first in a polycationic 10 mg/mL solution of an osmium complex and a polyanionic 10 mg/mL solution of GOX, both in 0.1 M PBS, for about 20 min. In between immersions, the wafers were rinsed with 0.1 M PBS and dried under flowing $N_2$.

Figure 12:
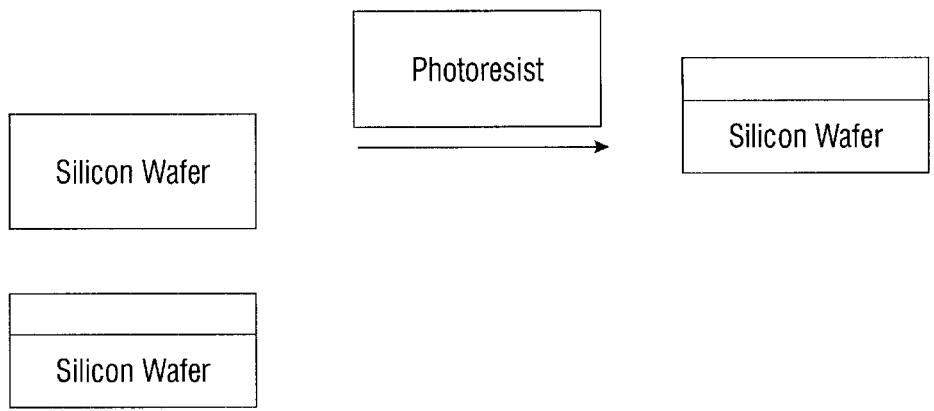
FIG. 12. Schematic for the fabrication of a PDMS master stamp that was utilized to deposit the initial layer of MUA for multilayer growth in spatially distinct regions.

Multilayer Patterning. The fabrication of a PDMS master stamp that was utilized to deposit the initial layer of MUA for multilayer growth in spatially distinct regions is depicted in FIG. 12.

Multilayer Crosslinking. In certain studies, the cationic and anionic layers were chemically or photo-chemically crosslinked. using either gluteraldehyde vapors or photo-chemical initiation in a DMPA solution. Chemical crosslinking was accomplished using glutaraldehyde where a multilayer wafer consisting of GOX and $Os(bpy)_2(PVP)$-co-allylamine was placed in a petri dish containing approximately 50 μL of glutaraldehyde. The wafer was left alone to be crosslinked via the glutaraldehyde vapors for about 2 h. For photochemical crosslinking, a multilayer wafer was immersed in 10 mg/mL solution of DMPA in 0.1 M PBS.

Electrochemical Characterization. Conducting wire was soldered onto all multilayer wafers. These wafers were then immobilized in a plexiglass electrochemical test cell. The test cell was composed of two circular pieces which entrapped a gold substrate in between using o-rings. The substrate was connected to the electrochemical apparatus, with a certain portion of the wafer exposed to 1.0 mL of 0.1 M PBS. $N_2$ was bubbled into this solution, which also contained a counter and reference electrode. Either of two studies were then conducted; cyclic voltammetry or chronoamperometry. For cyclic voltammetry, the applied potential was cycled linearly from 0 to 500 mV. Varying scan rates were utilized for determination of charge diffusion coefficients. Aliquots of glucose were also added to increase the concentration from 0 to 10 mM in either 1 or 2 mM increments. The increases in peak current was then monitored as a correlation for the analyte glucose concentration. Chronoamperometry was typically performed where the electrode was preconditioned to and operated at a constant applied potential of 300 mV. When the current flattened out, aliquots of substrate were added, and step changes in current monitored with time.

Equipment. The equipment for electrochemical analysis included a CV-50W Voltammetric Analyzer (Bioanalytical Systems), a C2 Cell Stand, an Ag/AgCl reference electrode and a platinum counter electrode. All of the electrochemical apparatus was controlled using a Toshiba Pentium PC. Photocrosslinking initiated with UV light was perfromed using a 365 nm, 20 mW/cm² lamp. Ellipsometry was performed using a Gaertner L2W26D ellipsometer with a 70° angle of incidence.

Ellipsometry Measurements. All thickness and refractive indices were calculated using Gaertner software. All measurements were made using a He/Ne (633.8 nm) laser. The model utilized assumed a film refractive index of 1.46. Measurements were taken in between each of the steps depicted in FIG. 15 and discussed in the fabrication section.

Results and Discussion

Multilayer Formation. One of the factors of a well ordered and defined biosensor deals with the ability to address any size and orientation issues involved at the molecular level. With this in mind, ellipsometric data was obtained, in the manner defined earlier, after each adsorption of subsequent layers. Table 1 represents the increase in size of each layer during the alternate cationic/anionic attachments.

TABLE 1

Increase in Thickness as Measured by Eilipsometry Upon Attachment of Each Subsequent Layer

|  | Wafer #1 | Wafer #2 |
|---|---|---|
| MAU | 12.2 Å | 12 Å |
| Osmium | 26.8 Å | 24.2 Å |
| GOX | 30 Å | 34.7 Å |
| Osmium | 42.8 Å | 46.2 Å |
| GOX | 51.6 Å | 50.5 Å |

The agreement between the examples shown here and other samples has been quite high. Specifically, The MUA layers are expected to and have been approximately 12 Å. The Osmium thickness should be and is about 12 Å to about 14 Å.

The average size of the cationic multilayer $(Os(bpy)_2(PVP)$-co-allylamine) was larger, about 12.8 Å, than the average anionic multilayer (GOX), about 6.7 Å. Despite a large molecular weight of 186,000, GOX has a very globular form that restricts its maximum length. The Osmium complexes, on the other hand, are typically straight chains that are capable of longer extentions. Nevertheless, the average size increases were quite consistent when attaching a total of only five layers, and the sizes of the monolayers on average compare favorably with reported values for non-biosensor applications (Hammond and Whitesides, 1995; Clark et al., 1997).

Osmium Sites Per Layer. Aside from characterization of the size of individual monolayers, it is also important, especially for biosensor purposes, to characterize the number of active osmium redox sites present in each layer. This number was determined based upon the cyclic voltammogram of a wafer with only a single layer containing any redox species ($MUA/Os(bpy)_2(PVP)$-co-allylamine/GOX). The area of under the peak was measured from the voltammogram, and it was determined that there was typically 5.78 mol/cm³ of the osmium complex present per multilayer. It is contemplated that a range of about four to about ten mol/cm³ osmium complex per multilayer, with the preferred value approaching about ten mol/cm³ would be particularly useful in the present invention.

Figure 11:
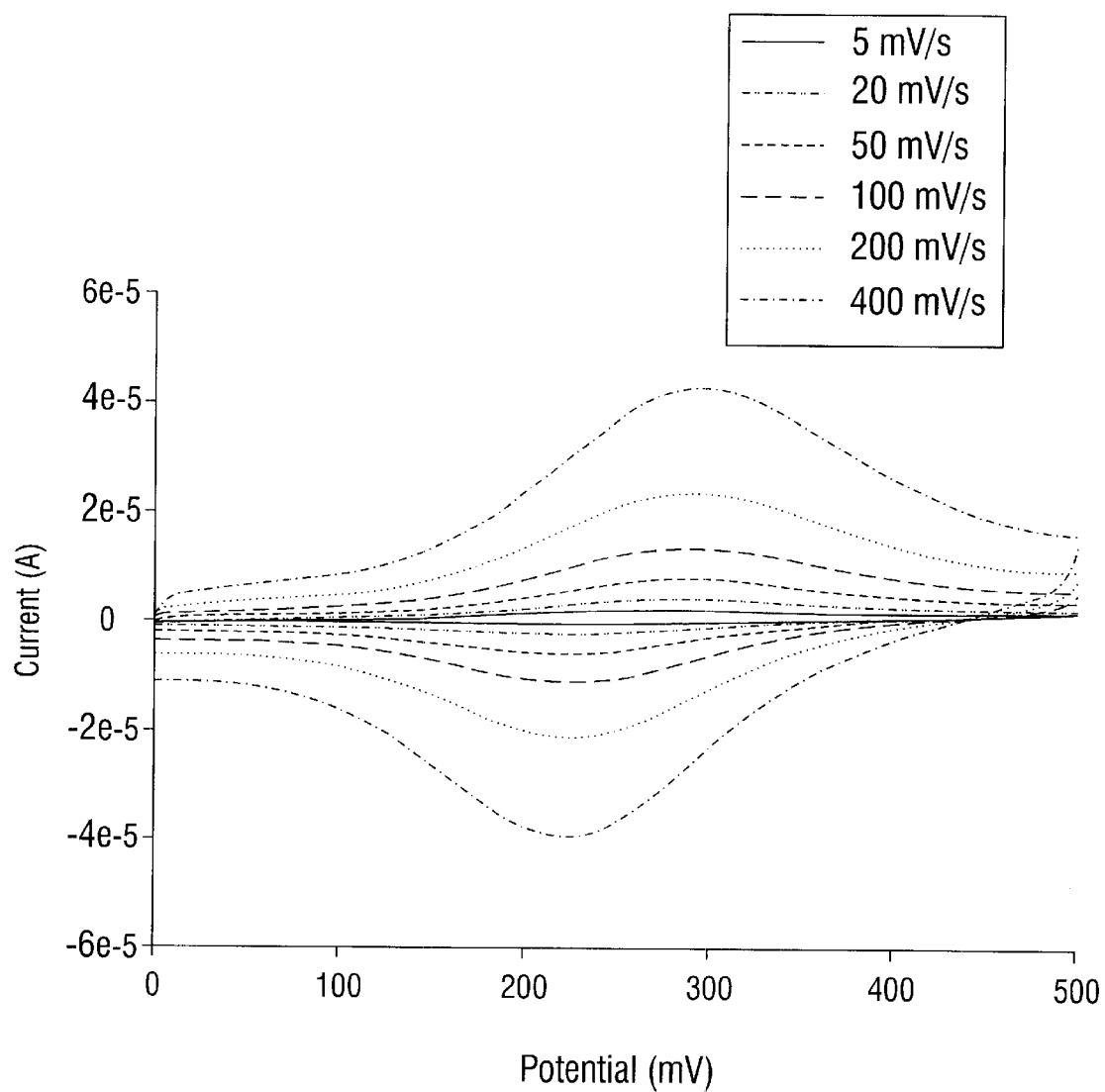
FIG. 11. Cyclic voltammograms as a function of increasing scan rate for a multilayer film consisting of 2 layers each of GOX and osmium. Voltages used included (—) 5 mV/s, (-) 20 mV/sec, (—.), 50 mV/sec (- -) 100 mV/sec, (....) 200 nV/sec, and 400 mV/sec (—.-).

Electrochemical Wafer Characterization. Cyclic voltammograms as a function of increasing scan rate are depicted in FIG. 11. At a scan rate of 10 mV/s, the formal potential was 248 mV with a difference in peak potential of 55 mV. This data was used to perform a linear regression of the peak current against the square root of scan rate using the Randles-Sevcik equation (11) (Forster and Heller, 1990). This equation requires the assumption of semiinfinite linear diffusion in order to determine $D_{CT}$, or the diffusion coefficient of charge transfer.

$$i_p = [0.4463(nF)^{1.5} A\, D_{CT}^{0.5} C^* v^{0.5}]/(RT)^{0.5} \qquad (11)$$

Here, $i_p$ is the peak anodic current, n represents the number of electrons involved in the oxidation, F is Faraday's Constant, A the electrode surface area, C* the concentration of redox (osmium) centers in the layer, v the scan rate, R is the universal gas constant and T is the temperature. Assuming a C* value of 5.78 mol/cm³, $D_{CT}$ was determined to be on the order of $10^{-10}$ cm²/s. This value compares with ~$10^{-2}$ cm²/s $D_{CT}$.

Substrate Response. The response of the enzyme electrode addition of substrate aliquots was characterized using both chronoamperometry and cyclic voltammetry. Typical current response values derived from chronoamperometric studies are depicted in FIG. 11.

Layer Crosslinking. Certain multilayers were chemically or photo-chemically crosslinked. It was expected that crosslinking within a given layer may increase charge transfer rates for the cationic osmium based charge mediator and that crosslinking between enzyme and mediator layers may increase current response values. There was an increase in current density in the range of glucose up to 10 mM upon crosslinking with glutaraldehyde (Tatsuma et al., 1994). It was found that these crosslinked films were able to retain nearly 100% of their activity for at least three weeks.

Patterning. Spatially distinct and individually addressable biosensor array members were made with patterns of the multilayers, generated by microcontact printing technology (Xia and Whitesides, 1998).

EXAMPLE 7

Implantation of Polymer Microspheres in a Rat Animal Model

In this example, the device described above in Example 5 is implanted in vivo in rats to study the effects of time lag and long term response. The polymers are injected and allowed to heal according to a pending animal use protocol as described below. Transdermal glucose measurements using this animal model are used to determine the ability of the microspheres to sense glucose in vivo.

Non-diabetic male hairless rats of approximately 300 g are used. Hairless rats are chosen because their skin properties are similar to those of humans. The rats are anesthetized with metafane by inhalation. The sterile microspheres suspended in isotonic saline are injected intradermally in either the right or left flank of the animal. The animals are then returned to their cage. After fasting overnight, the animals are anesthetized by metafane inhalation, and the site of microsphere implantation positioned directly below optical fibers for both excitation and emission. Fluorescence intensity measurements and venous blood samples are acquired at 10 minute intervals over a 3 h period. Blood samples of approximately 40 µl are collected via cannulation of the tail vein. Blood glucose concentration is increased in these studies by administering an IV bolus of 5% dextrose to the animal. At the end of the study, the animals are returned to their cage and are not used for at least 7 days. After 30 days, the animals are sacrificed by carbon dioxide asphyxiation and the microspheres and surrounding tissue removed intact. This method of euthanasia is consistent with the recommendation of the Panel on Euthanasia of the American Veterinary Medical Association.

In a portion of the animals, the microspheres are separated from the surrounding tissue and assayed for ConA activity in vitro as described above. The remainder of the microsphere-tissue samples are fixed immediately in 10% neutral buffered formalin for 48 h. The samples are then processed for histology by serial dehydration, paraffin embedding, sectioning, and staining. Mass transfer within the microspheres can be increased by increasing PEG chain length, and thereby increasing conformational flexibility within the gel. Hematoxylin and eosin staining are used to determine the morphology of tissue surrounding the implants and the extent of fibrosis, a chronic inflammatory response. Pendent PEG chains can be added to the microspheres to suppress the fibrotic response and create a "stealth" particle similar to those contemplated for drug delivery aspects of the present invention.

Similar studies are performed in diabetic animals. In these studies glucose is varied from hypoglycemia (50 mg/dl) to hyperglycemia (400 mg/dl) levels. Insulin, administered by subcutaneous injection, is used to lower glucose levels. At the end of the study, the animals are returned to their cage and are not used for another study for at least 7 days. During this period, diabetic animals are administered insulin (twice daily) to prevent extended periods of hyperglycemia.

After 30 to 120 days, the animals are sacrificed by carbon dioxide asphyxiation. The microspheres and surrounding tissue are removed intact. In this population, the animals are subject to the glucose response studies only once every 20 days to minimize stress to the animals and tissue damage as the result of repeated cannulation. Upon explantation, some of the microspheres are separated from the surrounding tissue and assayed for microsphere activity in vitro as described above to determine whether ConA within the sphere has been reversibly or irreversibly modified during the implantation period. The remainder of the microsphere-tissue samples are fixed immediately in 10% neutral buffered formalin for 48 hours.

The biocompatibility of the microspheres and the degree of host tissue responses such as fibrosis are assessed by conventional histopathologic methods. A small number of non-diabetic animals (5) are allowed to survive for a maximum of 120 days to assess the long-term host response to the implanted microspheres. The samples are processed for histology by serial dehydration, paraffin embedding, sectioning, and staining. Hematoxylin and eosin staining are used to determine the morphology of tissue surrounding the implants and the extent of fibrosis.

EXAMPLE 8

Fluorescent pH-Sensitive Hydrogels

Glucose oxidase catalyzes glucose and generates acidic byproducts. The acid produced results in a lowered pH in the local environment, the reduction of which is proportional to glucose concentration. SNAFL-1, a highly sensitive pH-indicating dye developed by Molecular Probes, along with glucose oxidase, was used to measure low concentrations of glucose.

SNAFL-1 and glucose oxidase were dissolved in 0.1 M PBS to provide a buffered system similar to that encounted in vivo. A concentrated glucose aliquot was added to the solution, and the change in SNAFL fluorescence emission at 540 and 625 resulting from an excitation at 510 nm was recorded over time. A large fluorescence change (about 30,000 photons/s/(400 mg/dL glucose) resulted from the addition of 400, 800, and 1200 mg/dL of glucose.

SNAFL-1 is preferred for immobilize in PEG hydrogels due to the existence of both carboxy and succinimidyl ester variants. The dye can be immobilized into PEG hydrogels multiple ways, including activation of the carboxy end-groups on SNAFL (seminaphthofluorescein) via EDAC ((1-ethyl-3-(3-dimethylaminopropyl) carbodiimide) and then reacting with amine-containing moieties such as poly(allyl amine) or terminal lysine and argine residues on glucose oxidase, and directly reacting the succinimidyl ester version of SNAFL with similar amine-containing moieties. These flurophore-modified compounds can then be chemically or physically immobilized into the PEG hydrogels as described herein for other dyes. SNAFL-1 conjugation onto the enzyme has the additional advantage of placing the fluorophore in close proximity to the acid production site on the enzyme.

Use of fluorescence to track the pH change resulting from the interaction of glucose and glucose oxidase is a significant improvement of prior systems, as it eliminates much of the moving components of the sensing system. The Con A-dextran system may require sufficient mobility of the Con A and dextran for association/disassociation due to glucose.

However, hydrogels are not dependent upon PEG as an immobilize matrix or SNAFL as the fluorescent indicator. Similar hydrogels, for example polyHEMA or acrylamide, and other pH-sensitive fluorophores, such as HPTS (1-hydroxy-pyridine-3',8'-trisulfonate) could be utilized to manufacture implantable, biocompatible hydrogels for non-invasive interrogation.

EXAMPLE 9

Chemical Detectors

SNAFL-1 was used to detect paraxaon, a model pesticide used for testing chemical warfare sensors. An organophosphate hydrolase enzyme, which breaks down organophosphates (the active components in chemical nerve agents) to among other by products a proton, was mixed in a low buffered solution with SNAFL-1. The released proton results in an acidic shift of the aqueous solution. By monitoring the emission ratio at 540 and 625 nm from a 510 nm excitation, paraxaon quantities as low as 100 nM could be optically assayed. Furthermore, the enzyme was successfully immobilized inside a PEG hydrogel, where it could be used for fluorescent pH-based sensing of organophosphates.

EXAMPLE 10

Hollow Core Alginate Spheres

Immobilize of proteins such as Con A can result in the reduction of Con A sugar-binding activity due to conformational changes of the protein within the hydrogel. This conformational change and loss of sugar-binding activity results in a less sensitive hydrogel. In order to limit conformational changes in the protein, alginate capsules with a liquid center were developed.

Low viscosity sodium alginate, which has a lower molecular weight than the higher viscosity alginates, was used to prepare the inner core of alginate capsules by crosslinking with calcium cations. The spheres were then transferred to a high MW poly-L-lysine (PLL) solution. The spheres were then soaked in an additional solution of sodium alginate, resulting in an electrostatic complex between the alginate and PLL. The inner core of alginate was then dissolved by soaking the spheres in a solution containing a calcium chelating agent, such as sodium citrate. This results in the reduction of the ionic bonds holding together the inner alginate core. Diffusion of the free alginate chains out of the inner core results in microcapsules with a liquid core.

Excessively high molecular weight dextrans cart be incorporated into the liquid core by dissolving them in the alginate precursor solution. Con A and lower molecular weight dextrans would dissolve out of the core similar to the initial alginate. Instead of including them in the initial precursor solution, they can be added by taking the end product and soaking them in a concentrated solution of Con A/dextran. After the biomolecules have diffused into the microcapsules, they are then transferred to a solution of low MW PLL (MW 4000–7500). The complex formed between the polyelectrolytes results in a membrane with a low molecular weight cutoff sufficient to prevent diffusion of Con A/dextran out of the capsules.

EXAMPLE 11

STAR PEGs

STAR PEGs (Shearwater Polymers, Huntsville, Ala.) are PEGs consist of multiple PEG arms extending from a core molecule. By functionalizing the PEG end groups, Con A and dextran could be immobilized directly to the end of several flexible PEG chains. Limited cross-linking between the STAR PEGs could then be utilized to manufacture PEG hydrogels with Con A/dextran immobilized on highly flexible strands at the exterior of the hydrogel.

EXAMPLE 12

Solution Polymerization Recipe for PEG

In a one embodiment, solution polymerized PEG microspheres will be manufactured by chemical production of free radicals using the following recipe: an initial organic phase consisting of sorbitan trioleate, toluene, and chloroform will be stirred under nitrogen for 30 minutes. TEMED, a chemical accelerator, will be added, and stirred for an additional 10 minutes. A premixed solution of ethylene glycol dimethacrylate, TPT and ammonium persulfate in PBS will be added, and reacted under nitrogen for approximately 30 minutes.

All of the compositions, methods and apparatus disclosed and claimed herein can be made and executed without undue experimentation in light of the present disclosure. While the compositions and methods of this invention have been described in terms of preferred embodiments, it will be apparent to those of skill in the art that variations may be applied to the compositions, methods and apparatus, and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abruna, Denisevich, Umana, Meyer, Murray, *J. Am. Chem. Soc.*, 103:1–5, 1981.

Armour et al., "Long-term intravascular glucose sensors with telemetry," *Artificial Organs*, 13:171, 1989.

Ballerstadt and Schultz, *Analytica Chimica Acta*, 345:203–212, 1997.

Berger, Itzkan, Feld, "Near-Infrared Raman spectroscopy of human whole blood and serum", *Proceedings of the SPIE*, V2982:87–90, 1997.

Berger, Wang, Feld, *Applied Optics*, 35:209–212, 1996.

Bradford, *Anal. Biochem.*, 72:248–254, 1976.

Bretz and Abruna, "Adsorption-desorption processes of redox-active osmium thiol monolayers," *J. Electroanalyt. Chem.*, 408:199–211, 1996.

Britland, Perez-Amaud, Clark, McGinn, Connolly, Moores, *Biotechnol. Prog.*, 8:155–160, 1992.

Bruckel et al., "In vivo measurement of subcutaneous glucose concentrations with an enzymatic glucose sensor and a wick method," *Klin. Wochenschr.*, 67:491–495, 1989.

Bruulsema, *Optics Letters*, 22:190–192, 1997.

Bu, Mikkelsen, English, *Anal. Chem.*, 67:4071–4076, 1995.

Cameron and Coté, "Noninvasive glucose sensing utilizing a digital closed-loop polarimetric approach," *IEEE Trans. Biomed. Eng*, 44(12):1221–27, 1997.

Cameron and Coté, *IEEE Trans. Biomed. Eng*, 44:1221–1227, 1997.

Cass, Davis, Francis, Hill, Aston, Higgins, Plotkin, *Anal. Chem.*, 56:667–71, 1984.

Chee, Yang, Hubbell, Berno, Huang, Stem, Winkler, Lockhart, Morris, Fodor, *Science*, 274:610–614, 1996.

Chen, Fluorescent protein-Dye Conjugaets II. Gamma Globulin Conjugated with Various Dyes. *Archives of Biochemistry and Biophysics*, 133:263–276, 1969.

Chowdhury and Hubbell, "Adhesion prevention with ancrod released via a tissue-adherent hydrogel," *J. Surg. Res.*, 61:58–64, 1996.

Clark and Hammond, "Engineering the microfabrication of layer-by-layer thin films," *Adv. Mater.*, 10:1515–1519, 1998.

Clark, Montague, Hammond, "Ionic effects of sodium chloride on the templated deposition of polyelectrolytes using layer-by-layer ionic assembly," *Macromolecules*, 30:7237–7244, 1997.

Conix, "Poly[1,3-bis(p-carboxyphenoxy)-propane anhydride]," *Macromolecular Syntheses* 2:95–99, 1966.

Coté, G. L., "Noninvasive Optical Glucose Sensing-An Overview", *J. Clin. Eng*, 22(4):253–259, 1997.

Coté, Fox, Northrop, "Noninvasive optical polarimetric glucose sensing using a true phase measurement technique," *IEEE Trans. Biomed. Eng.*, 39(7):752–756, 1992.

Coté, Fox, Northrop, *IEEE Trans. Biomed. Eng.*, 39:752–756, 1992.

Coté, *J. Clin. Eng*, 22:253–259, 1997.

Cotran, Kumar, Robbins, In: *Robbins Pathologic Basis of Disease*, 4th ed., Philadelphia, Saunders, pp. 994–1005, 1989.

Csoregi, Quinn, Schmidtke, Lindquist, Pishko, Ye, Katakis, Heller, "Design, characterization, and one-point in vivo calibration of a subcutaneously implanted glucose electrode," *Anal. Chem.*, 66:3131–3138, 1994.

Damme, Peumans, Pusztai, Bardocz, In: *Handbook of Plant Lectins: Properties and Biomedical Applications*, Wiley and Sons, West Sussex, 1998.

Day, "SEC Accuses Futrex Incorporated of Fraud," *Washington Post*, September 24 issue, Washington, D.C., 1996

De Belder and Granath, "Preparation and properties of fluorescein-labeled dextrans," *Carb. Res.*, 30:375–378, 1973.

de Gennes, *Scaling Concepts in Polymer Physics;* Cornell University Press: Ithaca, 1979.

Degani and Heller, "Electrical Communication between Redox Centers of Glucose Oxidase and Electrodes via Electrostatically and Covalently Bound Redox Polymers," *J. Am. Chem. Soc.*, 111:2357–8, 1989.

Delgado, Francis, Fisher, *Crit. Rev. Ther. Drug Carrier Sys.*, 9:249–304, 1992.

Denisevich, Abruna, Leidner, Meyer, Murray, *Inorg. Chem.*, 21:2153–2161, 1982.

Desai and Hubbell, "A solution technique to incorporate polyethylene oxide and other water soluble polymers into surfaces of biomaterials," *Biomater.*, 12:144–53, 1991a.

Desai and Hubbell, "Biological responses to polyethylene oxide modified polyethylene terephthalate surfaces," *J. Biomed. Mater. Res.*, 25:829–843, 1991b.

Diabetes Control and Complications Trial Research Group, "The Effect of Intensive Treatment of Diabetes on the Development and Progression of Long-Term Complications in Insulin-Dependent Diabetes Mellitus," *New Engl. J. Med.*, 329:977–986, 1993.

Diabetes Control and Complications Trial Research Group, *N. Engl. J. Med.*, 329:977–986, 1993.

Domb and Langer, "Polyanhydrides. I. Preparation of high molecular weight polyanhydrides," *Journal of Polymer Science: Part A: Polymer Chemistry* 25:3373–3386, 1987.

Dontha, Nowall, Kuhr, "Generation of biotin/avidin/enzyme nanostructures with maskless photolithography," *Anal. Chem.*, 69:2619–2625, 1997.

Dontha, Nowall, Kuhr, *Anal. Chem.*, 69:2619–2625, 1997.

Drumheller and Hubbell, "Densely crosslinked polymer metworks of poly(ethylene glycol) in trimethylolpropane triacrylate for cell resistant surfaces," *J. Biomed. Mater. Res.*, 29:207–215, 1995.

Edelman and Wang, *J. Biol. Chem.* 253:3016–3022, 1978.

Edelman, Gunther, Wang, Yahara, Cunningham, "Concanavalin A derivatives with altered biological activities," *Proc. Nat. Acad. Sci. USA*, 70(4):1012–1016, 1973.

Fischer et al., "Assesment of subcutaneous glucose concentration: validation of the wick technique as a reference for implanted electrochemical sensors in normal and diabetic dogs," *Diabetol.*, 30:940–945, 1987.

Fischer et al., "Wick technique: reference method for implanted glucose sensors," *Art. Org.*, 13:453–457, 1989.

Forster and Vos, "Charge transport properties of poly(N-vinylimidazole) containing $[Os(N)_6]^{2+/3+}$ moieties," *J. Inorg. Organomet. Polym.*, 1:67–86, 1991.

Forster and Vos, *J. Inorg. Organomet. Polym.*, 1:67–86, 1991.

Frederick, Tung, Emerick, Masiarz, Chamberlain, Vasavada, Rosenberg, Chakraborty, Schopter, Massey, *J. Biol. Chem.*, 265:3793–3802, 1990.

Geng, Longmire, Reed, Parcher, Barbour, Murray, *Chemistry of Materials*, 1:58–63, 1989.

Glabe, Harty, Rosen, *Analytical Biochem.*, 130:287–294, 1983.

Goetz, Jr., Coté, March, Erckens, Motamedi, "Application of a multivariate technique to Raman spectra for quantification of body chemicals," *IEEE Trans. Biomed. Eng*, 42(7):728–31.

Goldstein, Hollerman, Merrick, *Biochimica Biophysica Acta*, 97:68–76, 1965.

Goosen, O'Shea, Gharapetian, Chou, Sun, "Optimization of microencapsulation parameters: Semipermeable microcapsules as a bioartificial pancreas," *Biotechnol. Bioeng.*, 28:146–150, 1985.

Gough, "The composition and optical rotatory dispersion of bovine aqueous humor," *Diabetes Care*, 5(3):266–270, 1982.

Gregg and Heller, "Cross-linked redox gels containing glucose oxidase for amperometric biosensor applications," *Anal. Chem.*, 62:258–262, 1990.

Gregg and Heller, "Redox Polymer Films Containing Enzymes. 1. A Redox-Conducting Epoxy Cement: Synthesis, Characterization, and Electrocatalytic Oxidation of Hydroquinone," *J. Phys. Chem.*, 95:5970–5975, 1991a.

Gregg and Heller, *J. Phys. Chem.*, 95:5976–5980, 1991b.

Gregoriou, Hapanowicz, Clark, Hammond, "Infrared studies on novel optically responsive materials: orientation characteristics of sulfonated polystyrene/poly (diallyldimethylammonium chloride) ionic polymer multilayers on patterned self-assembled monolayers," *Applied Spectroscopy*, 51:470–476, 1997.

Gunther, Wang, Yahara, Cunningham, Edelman, "Concanavalin A Derivatives with Altered Biological Activities," *Proc. Nat. Acad. Sci. USA,* 70:1012–1016, 1973.

Haas, Velazquez, Porat, Murray, *J. Phys. Chem.,* 99:15279–15284, 1995.

Hale, Boguslavsky, Inagaki, Karan, Lee, Skotheim, Okamoto, "Amperometric glucose biosensors based on redox polymer-mediated electron transfer," *Anal. Chem.,* 63:677–682, 1991.

Hale, Boguslavsky, Inagaki, Karan, Lee, Skotheim, Okamoto, *Anal. Chem.,* 63:677–682, 1991.

Hale, Boguslavsky, Inagaki, Lee, Skotheim, Karan, Okamoto, *Mol. Cryst. Liq. Cryst.,* 190:251–258, 1990.

Hammond and Whitesides, "Formation of polymer microstructures by selective deposition of polyion multilayers using patterned self-assembled monolayers as a template," *Macromolecules,* 28:7569–7571, 1995.

Hanssen, "Diabetic control and microvascular complications: the near-normoglycaemic experience," *Diabetol.,* 29:677–784, 1986.

Hassen, Doyal, Peppas, "Dynamic behavior of glucose responsive methyacrylic acid-G-ethylene glycol hydrogels," *Macromolecule,* 30:6166–6173, 1997.

Haugland, In: *Handbook of Fluorescent Probes and Research Chemicals,* 6th ed., 1996.

H. C. van de Hulst, Light scattering by small particles, Dover Publications, New York, 1957, 1981.

Healey, Foran, Walt, *Science,* 269:1078–1080, 1995.

Henning and Cunningham, In: *Commercial Biosensors: Applications to Clinical, Bioprocess, and Environmental Samples;* Ramsay, G. (Ed.); John Wiley & Sons, Richmond, Va., Vol. 148, pp 3–46, 1998.

Hill-West et al., "Inhibition of thrombosis and intimal thickening by in situ photopolymerization of thin hydrogel barriers," *Proc. Natl. Acad Sci. USA,* 91:5967–5971, 1994.

Hodak, Etchenique, Calvo, Singhal, Bartlett, "Layer-by-layer self-assembly of glucose oxidase with a poly(allylamine)ferrocene redox mediator," *Langmuir,* 13:2708–2716, 1997.

Hou, Fang, Chen, "An amperometric enzyme electrode for glucose using immobilized glucose oxidase in a ferrocene attached poly(4-vinylpyridine) multilayer film," *Analytical Letters,* 30:1631–1641, 1997.

Hou, Yang, Fang, Chen, "Amperometric glucose enzyme electrode by immobilizing glucose oxidase in multilayers on self-assembled monolayers surface," *Talanta,* 47:561–567, 1998.

Jagemann, *Zeitschrift fur Physikalische Chemie,* 191:179–190, 1995.

Katakis, Ye, Heller, *J. Am. Chem. Soc.,* 116:3617–3618, 1994.

Kerner, Lindquist, Pishko, Heller, "Amperometric glucose sensor containing glucose oxidase cross-linked in redox gels," In: *In Vivo Chemical Sensors: Recent Developments;* Turner, A. P. F., Alcock, S. J., Eds., 1993.

King, Coté, McNichols, Goetz, Jr., "Multispectral polarimetric glucose detection using a single pockels cell," *Opt. Eng.,* 33(8):2746–2753.

Kober et al., "Synthetic Routes to New Polypyridyl Complexes of Osmium (II)," *Inorg. Chem.,* 27:4587–4598, 1988.

Kober, Caspar, Sullivan, Meyer, "Synthetic routes to new polypyridyl complexes of osmium(II)," *Inorg. Chem.,* 27:4587–4598, 1988.

Kohl and Cope, "Influence of glucose concentration on light scattering in tissue-simulating phantoms, *Optics Letters,* 19(24):2170–72, 1994.

Kohler and Milstein, "Continuous cultures of fused cells secretaring antibody of predefined specificity," *Nature,* 256:495–497, 1975.

Koudelka et al., "In vivo behavior of hypodermically implanted microfabricated glucose sensors," *Biosensors & Bioelectronics,* 6:31–36, 1991.

Krongauz, In: *Processes in Photoreactive Polymers;* Krongauz, V. V., Trifunac, A. D., Eds.; Chapman and Hall, 1995.

Lakowicz and Maliwal, "Optical sensing of glucose using phase-modulation fluorimetry," *Analytica Chimica Acta,* 271:155–164, 1993.

Lakowicz and Maliwal, *Analytica Chimica Acta,* 271:155–164, 1993.

Lambert, *LEOS Newsletter,* 12:19–22, 1998.

Leong et al., "Multichannel microelectrode probes machined in silicon," *Biosensors & Bioelectronics,* 5:303–310, 1990.

Linke, Kerner, Kiwit, Pishko, Heller, "Amperometric biosensor for in vivo glucose sensing based on glucose oxidase immobilized a redox hydrogel," *Biosensors and Bioelectronics,* 9:151–158, 1994.

Madou and Tierney, "Required technology breakthroughs to assume widely accepted biosensors," *Appl. Biochem. Biotech.,* 41:109–128, 1993.

Maier, Walker, Fantini, Franceschini, Gratton, "Possible correlation between blood glucose concentration and the reduced scattering coefficient of tissues in the near infrared," *Optics Letters,* 19(24):2062–64.

Mansouri and Schultz, "A miniature optical glucose sensor based affinity binding," *Biotech.,* 2:885–90, 1984.

Mansouri and Schultz, *Biotech.,* 885–890, 1984.

Marbach, Koschinsky, Gries, Heise, "Noninvasive blood glucose assay by near-IR diffuse reflectance spectros. of the human inner lip," *Appl. Spectrosc.,* 47:875–881, 1993.

March, Rabinovitch, Adams, "Noninvasive glucose monitoring of the aqueous humor of the eye: part I animal studies and the scleral lens," *Diabetes Care,* 5(3):259–265.

Mattiasson and Ling, *J. Immunol. Meth.,* 38:217–223, 1980.

McLean, Stayton, Sligar, "Engineering protein orientation at surfaces to control macromolecular recognition events," *Anal. Chem.,* 65:2676–2678, 1993.

McShane, Coté, Spiegelman, "Variable selection in multivariate calibration of a spectroscopic glucose sensor", *Appl. Spectroscopy,* 1997.

Meadows and Schultz, *Analytica Chimica Acta,* 280:21–30, 1993.

Meadows and Schultz, *Talanta,* 35:145–150, 1988.

Meadows, Ph.D. Dissertation, University of Michigan, Ann Arbor, 1988.

Meadows, Shafer, Schultz, "Determining the extent of labeling for tetramethylrhodamine protein conjugates," *Immunol. Meth.,* 143:263–272, 1991.

Meadows, Shafer, Schultz, *J. Immunol. Meth.,* 143:263–272, 1991.

Modarres, "Reliability and Risk Analysis," New York: Marcel Dekker, Inc, 1993.

Molecular Probes, "Conjugation with Amine-Reactive Probes", MP 0143, December, 1996.

Mooney, Hunt, McIntosh, Liberko, Walba, Rogers, *Proc. Natl. Acad. Sci. USA,* 93:12287–12291, 1996.

Nakayama, Zheng, Nishimura, Matsuda, *ASAIO J.,* 41:M418–M421, 1995.

National Institute of Diabetes and Digestive and Kidney Diseases, "The diabetes control and complications trial," June 1993.

National Institute of Diabetes and Kidney Diseases, "Diabetes Overview," NIH, Pub. No. 94–3235, 1994.

Nishihara, Dalton, Murray, *Anal. Chem.*, 63:2955–2960, 1991.

Ohara, Rajagopalan, Heller, *Anal. Chem.*, 65:3512–3517, 1993.

Ott, Traber, Kramer, In: *Flavins and Flavoproteins;* Bray, R., Engel, P., Mayhew, S., Eds.; Walter de Gruyter and Co.: Berlin, 1984.

Pathak, Sawhney, Hubbell, "In situ photopolymerization and gelation of water soluble monomers: a new approach for local administration of peptide drugs," *Polymer Preprints*, 33:65–66, 1992.

Pathak, Sawhney, Hubbell, "Rapid Photopolymerization of Immunoprotective Gels in Contact with Cells and Tissue," *J. Am. Chem. Soc.*, 114:8311–8312, 1993.

Pathak, Sawhney, Hubbell, *J. Am. Chem. Soc.*, 114:8311–8312, 1992.

Pishko, Katakis, Lindquist, Heller, Degani, *Mol. Cryst. Liq. Cryst.*, 190:221, 1990a.

Pishko, Katakis, Lindquist, Ye, Gregg, Heller, *Angewandte Chemie Intl. Ed.*, 29:82, 1990b.

Pishko, Michael, Heller, "Amperometric glucose microelectrodes prepared through immobilization of glucose oxidase in redox hydrogels," *Anal. Chem.*, 63:2268–2272, 1991.

Pishko, Michael, Heller, "Amperometric glucose microelectrodes prepared through immobilization of glucose oxidase in redox hydrogels," *Anal. Chem.*, 63:2268–2272, 1991.

Pishko, M. V., "Macromolecular Wiring of Oxidoreductases and Potential Interesting Applications" *Trends in Polymer Science,* 3(10):342, 1995.

Sirkar, K. and M. V. Pishko, Amperometric Biosensors Based on Oxidoreductases Immobilized in Photopolymerized Poly(ethylene glycol) Redox Polymer Hydrogels. *Anal. Chem.*, 70(14):2888–2894, 1998.

Quinn et al., "Kinetics of Glucose Delivery to Subcutaneous Tissue in Rats: A Study Utilizing Amperometric Biosensors," *Am. J Physiol.*, 269(32):E155, 1995b.

Quinn et al., "Photo-crosslinked copolymers of 2-hydroxyethyl methacrylate, poly(ethylene glycol) tetraacrylate and ethylene dimethacrylate for improving biocompatibility of biosensors," *Biomater.*, 16(5): 389–396, 1995a.

Quinn, Pishko, Schmidtke, Ishikawa, Wagner, Raskin, Hubbell, Heller, *Am. J. Physiol.*, 269:E155, 1995.

Reiser, In: *Photoreactive Polymers. The Science and Technology of Resists;* John Wiley and Sons: New York, 1989.

Robinson, Eaton, Haaland, Koepp, Thomas, Stallard, Robinson, "Noninvasive glucose monitoring in diabetic patients: a preliminary evaluation," *Clin. Chem.*, 38(9): 1618–1622, 1992.

Rouhi, "Biosensors Send Mixed Signals," *Chem. Eng. News* 75:41–45, 1997.

Rouhi, In: *Chem. Eng. News,* pp 41–45, 1997.

Russell, Pishko, Gefrides, Coté, *Proceedings of the 20th Annual International Conference of the IEEE Engineering in Medicine and Biology Society, Oct.* 29 to Nov. 1, 1998.

Sabatini, "Biocontrol's diabetes monitor still faces hurdles," *Pittsburg Post-Gazette November* 13*th issue, via Knight-Ridder/Tribune Business News via Individual Inc.,* Burlington, M 01803, 1996.

Sambrook, Fritsch, Maniatis, In: *Molecular Cloning: A Laboratory Manual,* Vol. 1, Cold Spring Harbor Laboratory Press, Cold Spring Harbor, N.Y., Ch. 7,7.19–17.29, 1989.

Sawhney et al., "Bioerodible hydrogels based on photopolymerized poly(ethylene glycol)-co-poly(alpha-hydroxy acid) diacrylate monomers," *Macromolecules,* 26:581–587, 1993.

Sawhney et al., "Optimization of photopolymerized bioerodible hydrogel properties for adhesion prevention," *J. Biomed. Mater. Res.,* 28:831–838, 1994.

Sawhney, Pathak, von Rensburg, Dunn, Hubbell, *J. Biomed. Mater. Res.,* 28:831–838, 1994.

Schmidt, Sluiter, Schoonen, "Glucose concentration in subcutaneous extracellular space," *Diabetes Care,* 16(5): 695–700, 1993.

Schmidtke, Pishko, Quinn, Heller, "Statistics for critical clinical decision making based on readings of pairs of implantable sensors," *Anal. Chem.,* 68:2845–2849, 1996.

Schultz and Meadows, "Design, manufacture and characterization of an optical fiber glucose affinity sensor based on an homogeneous fluorescence energy transfer assay system", *Analytica Chimica Acta,* 280:21–30, 1993.

Schultz and Sims, "Affinity sensors for individual metabolites," Biotechnol. *Bioeng. Symp.*, 9:65–71, 1979.

Schultz and Sims, *Biotech. Bioeng Symp.,* 9:65–71, 1979.

Schultz, Mansouri, Goldstein, "Affinity sensor: a new technique for developing implantable sensors for glucose and other metabolites," *Diabetes Care,* 5(3):245–53, 1982.

Seifert and Phillips, "Porous alginate-Poly(ethylene glycol) entrapment system for the cultivation of mammalian cells," *Biotechnol. Prog.,* 13:569–576, 1997.

Sirkar and Pishko, "Amperometric biosensors based on oxidoreductases immobilized in photopolymerized poly (ethylene glcol) diacrylate hydrogels," *Anal. Chem.,* 70:2888–2894, 1998.

Sirkar and Pishko, *Anal. Chem.* 70:2888–2894, 1998.

Small, Arnold, Marquardt, "Strategies for coupling digital filtering with partial least-squares regression: application to the determination of glucose in plasma by fourier transform near-infrared spectroscopy," *Anal. Chem.,* 65:3279–3289, 1993.

Speicher, "Can portable blood glucose monitoring improve outcomes of diabetic patients?," *Am. J. Clin. Path.,* 95(2): 112–116, 1991.

Stryer, *Ann. Rev. Biochem.,* 47:819–846, 1978.

Sukhorukov, Schmitt, Decher, "Reversible swelling of polyanion/polycation multilayer films in solutions of different ionic strength," *Ber. Bunsenges. Phys. Chem.,* 6:948–953, 1996.

Sundberg, Barrett, Pirrung, Lu, Kiangsoontra, Holmes, *J. Am. Chem. Soc.,* 117:12050–12057, 1995.

Tanaka, Matsumura, Veliky, *Biotechnol. Bioeng.,* 26:53–58, 1984.

Tatsuma, Saito, Oyama, "Enzyme Electrodes mediated by a Thermoshrinking Redox Polymer," *Anal. Chem.,* 66:1002–1006, 1994.

Tatsuma, Saito, Oyama, "Enzyme electrodes mediated by a thermoshrinking redox polymer," *Anal. Chem.,* 66:1002–1006, 1994.

Taylor et al., "'Wiring' of glucose oxidase within a hydrogel made with polyvinyl imidazole complexed with [(Os-4, 4'-dimethoxy-2,2'-bipyridine)Cl]+/2+," *J. Electroanal. Chem.,* 395:147–153, 1995.

Tolosa, Malak, Raob, Lakowicz, *Sensors Actuators B. Chemical,* 45:93–99, 1997.

Weber, "Signal-to-noise ratio in microelectrode-array-based electrochemical detectors," *Anal. Chem.,* 61:295–302, 1989.

West and Hubbell, *Reactive Polymers,* 25:139–147, 1995.

Whitesides, Mathias, Seto, "Molecular self-assembly and nanochemistry: A chemical strategy for the synthesis of nanostructures," *Science,* 254:1312–1319, 1991.

Wilson and Reach, "Can continuous glucose monitoring be used for the treatment of diabetes?," *Anal. Chem.* 64:381A–386A, 1992.

Wilson et al., "Progress toward the development of an implantable sensor for glucose," *Clin. Chem.,* 38:1613–1617, 1992.

Wise and Najafi, "Microfabrication techniques for integrated sensors and Microsystems," *Science,* 254:1335–1342, 1991.

Wysocki, "Impact of blood glucose monitoring on diabetic control: obstacles and interventions," *J. Behav. Med.,* 12(2):183–205, 1989.

Xia and Whitesides, "Soft lithography," *Angewandte Chemie International Edition,* 37:550–575, 1998.

Xu and Bard, "Immobilization and hybridization of DNA on an aluminum(II) alkanebisphosphonate thin film with electrogenerated chemiluminescent detection," *J. Am. Chem. Soc.,* 117:2627, 1995.

Ye, Hammerle, Olsthoorn, Schuhmann, Schmidt, Duine, Heller, "High current density "wired" quinoprotein glucose dehydrogenase electrode," *Anal. Chem.,* 65:238–241, 1993.

Yershov, Barsky, Belgovskiy, Kirillov, Kreindlin, Ivanov, Parinov, Guschin, Drobishev, Dubiley, Mirzabekov, "DNA analysis and diagnostics on oligonucleotide microchips," *Proc. Natl. Acad. Sci. USA,* 93:4913–4918, 1996.

What is claimed is:

1. A method for the detection of an analyte in an animal, wherein the analyte is glucose, comprising the steps of:

(a) implanting by injecting within the epidermis or dermis of the animal a composition comprising a hydrogel and an analyte detection compound, wherein said hydrogel comprises a cross-linked poly(ethylene glycol), poly(ethylene glycol)-co-anhydride, poly(ethylene glycol)-co-lactide, poly(ethylene glycol)-co-glycolide, poly(ethylene glycol)-co-orthoester, poly-isopropylacrylamide, polyHEMA, polyacrylamide, calcium alginate, or a combination thereof; and wherein said detection compound is selected from the group consisting of the competitive binding pair FITC-Dextran and TRITC-ConA, or FITC-Dextran and TRITC-succinyl-ConA, (b) measuring the analyte levels.

2. The method of claim 1, wherein said composition is injected in the epidermis of said animal.

3. The method of claim 1, wherein said composition is injected in the dermis of said animal.

4. The method of claim 1, wherein said composition is injected between about 0.05 mm and about 5 mm below the surface of the epidermis of said animal.

5. The method of claim 1, wherein said animal is a human.

6. The method of claim 1, wherein the composition has an average particle size up to about 10 microns in diameter.

7. The method of claim 1, wherein said composition produces an optical change upon contact with glucose.

8. The method of claim 7, wherein said composition produces a fluorescence change upon contact with glucose.

9. The method of claim 8, wherein said composition comprises at least a first fluorophore conjugate.

10. The method of claim 9, further comprising a second fluorophore conjugate, wherein said second fluorophore conjugate can accept photons from said first fluorophore conjugate and quench it.

11. The method of claim 10, said first fluorophore conjugate is FITC-dextran and said second fluorophore conjugate is TRITC-concanavalin A.

* * * * *